US011859219B1

(12) United States Patent
Niu et al.

(10) Patent No.: US 11,859,219 B1
(45) Date of Patent: Jan. 2, 2024

(54) METHODS OF ALTERING A TARGET NUCLEOTIDE SEQUENCE WITH AN RNA-GUIDED NUCLEASE AND A SINGLE GUIDE RNA

(71) Applicant: Flagship Pioneering Innovations V, Inc., Cambridge, MA (US)

(72) Inventors: Yajie Niu, Lexington, MA (US); Kristine Yu, Cambridge, MA (US); Frank Anthony Skraly, Watertown, MA (US); Randall William Shultz, Acton, MA (US); John P. Casey, Jr., Boston, MA (US); Brian Prescott Fiske, Cambridge, MA (US)

(73) Assignee: Flagship Pioneering Innovations V, Inc., Cambridge, MA (US)

( * ) Notice: Subject to any disclaimer, the term of this patent is extended or adjusted under 35 U.S.C. 154(b) by 62 days.

(21) Appl. No.: 15/858,581

(22) Filed: Dec. 29, 2017

Related U.S. Application Data

(60) Provisional application No. 62/440,676, filed on Dec. 30, 2016.

(51) Int. Cl.
*C12N 9/22* (2006.01)
*C12N 15/82* (2006.01)
*A01H 4/00* (2006.01)

(52) U.S. Cl.
CPC ........... *C12N 9/22* (2013.01); *C12N 15/8202* (2013.01); *A01H 4/008* (2013.01); *C12N 2310/20* (2017.05)

(58) Field of Classification Search
CPC ... C12N 9/22; C12N 12/8202; C12N 15/8202
See application file for complete search history.

(56) References Cited

U.S. PATENT DOCUMENTS

| | | | | |
|---|---|---|---|---|
| 8,771,945 | B1 | 7/2014 | Zhang | |
| 8,865,406 | B2 | 10/2014 | Zhang et al. | |
| 9,790,490 | B2 | 10/2017 | Zhang et al. | |
| 2013/0198893 | A1 | 8/2013 | Zhao et al. | |
| 2013/0326645 | A1 | 12/2013 | Cost et al. | |
| 2014/0068797 | A1 | 3/2014 | Doudna et al. | |
| 2014/0090113 | A1 | 3/2014 | Cogan et al. | |
| 2015/0059010 | A1 | 2/2015 | Cigan et al. | |
| 2015/0067922 | A1* | 3/2015 | Yang | C12N 15/8289 435/468 |
| 2015/0082478 | A1 | 3/2015 | Cigan et al. | |
| 2015/0167000 | A1 | 6/2015 | Voytas et al. | |
| 2016/0208272 | A1 | 7/2016 | Cigan et al. | |
| 2016/0264981 | A1* | 9/2016 | Yang | C12N 15/111 |
| 2016/0304892 | A1 | 10/2016 | Beetham et al. | |
| 2017/0037432 | A1* | 2/2017 | Donohoue | C12N 15/111 |
| 2017/0058271 | A1* | 3/2017 | Joung | C12Y 301/00 |
| 2017/0183677 | A1 | 6/2017 | Gao et al. | |
| 2017/0233756 | A1 | 8/2017 | Begemann et al. | |
| 2018/0016589 | A1 | 1/2018 | Gao et al. | |

FOREIGN PATENT DOCUMENTS

| | | |
|---|---|---|
| WO | WO 2013/160230 | 10/2013 |
| WO | WO 2013/176772 | 11/2013 |
| WO | WO 2013/192278 | 12/2013 |
| WO | WO 2014/065596 | 5/2014 |
| WO | WO 2014/089290 | 6/2014 |
| WO | WO 2015/026885 | 2/2015 |
| WO | WO 2015/038796 | 3/2015 |
| WO | WO 2015/131101 | 9/2015 |
| WO | WO 2016/105185 | 6/2016 |
| WO | WO 2017/061806 | 4/2017 |
| WO | WO 2018/085693 | 5/2018 |
| WO | WO 2018/140899 | 8/2018 |

OTHER PUBLICATIONS

Malnoy et al (DNA-Free Genetically Edited Grapevine and Apple Protoplast Using CRISPR/Cas9 Ribonucleoproteins. Frontiers in Plant Science. 1-9, 2016).*
Burris et al (Development of a rapid, low-cost protoplast transfection system for switchgrass (*Panicum virgatum* L.) Plant Cell Rep 35:693-704, 2016).*
Kumar et al (The CRISPR-Cas system for plant genome editing: advances and opportunities. Journal of Experimental Botany, vol. 66, No. 1 pp. 47-57, 2015).*
Malzahn et al (Application of CRISPR-Cas12a temperature sensitivity for improved genome editing in rice, maize, and *Arabidopsis*. BMC Biology. 17: 1-14, 2019) (Year: 2019).*
Raitskin et al (Comparison of efficiency and specificity of CRISPR-associated (Cas) nucleases in plants: An expanded toolkit for precision genome engineering 2019) (Year: 2019).*
Li et al (Multiplex and homologous recombination-mediated genome editing in *Arabidopsis* and *Nicotiana benthamiana* using guide RNA and Cas9. Nature Biotechnology 31:688-691, 2013), (Year: 2013).*
Burris et al (Development of a rapid, low-cost protoplast transfection system for switchgrass (*Panicum virgatum* L.) Plant Cell Rep 35:693-704, published online in 2015). (Year: 2015).*
Kumar et al (The CRISPR-Cas system for plant genome editing: advances and opportunities. Journal of Experimental Botany, vol. 66, No. 1 pp. 47-57, 2015). (Year: 2015).*
Schiml et al (Repair of adjacent single-strand breaks is often accompanied by the formation of tandem sequence duplications in plant genomes. PNAS 113, 7266-7271, Jun. 2016). (Year: 2016).*
Supplement of Li et al (Nature Biotechnology 31:688-691, 2013), (Year: 2013).*

(Continued)

*Primary Examiner* — Charles Logsdon
*Assistant Examiner* — Wayne Zhong
(74) *Attorney, Agent, or Firm* — Klarquist Sparkman, LLP

(57) ABSTRACT

Disclosed herein are compositions and methods for effecting alterations at a defined location in the genome of a plant cell or plant protoplast. Further disclosed are methods using an RNA-guided nuclease to alter a target nucleotide sequence in a cell or protoplast of a plant; embodiments of such methods include treatments with chemical or physical reagents or treatment of the cell or protoplast with a specific thermal regime, such as a heat treatment.

19 Claims, 12 Drawing Sheets

Specification includes a Sequence Listing.

(56) References Cited

OTHER PUBLICATIONS

Woo et al. (DNA-free genome editing in plants with preassembled CRISPR-Cas9 ribonucleoproteins. Nature Biotechnology, 33: 1162-1165, 2015) (Year: 2015).*

Burris et al. (Development of a rapid, low-cost protoplast transfection system for switchgrass (*Panicum virgatum* L.) Plant Cell Rep 35:693-704, published online 2015). (Year: 2015).*

Cheng et al (Agrobacterium tumefaciens mediated transformation of marine microalgae Schizochytrium. Microbiological Research 167, 179-186, 2012). Transforming Algae (water plant) 28oC (p. 180, left col, 4th para). (Year: 2012).*

Gao et al (Protoplast Transformation of Recalcitrant Alkaliphilic *Bacillus* sp. with Methylated Plasmid DNA and a Developed Hard Agar Regeneration Medium. PLOS One 1-7, 2011), transfecting bacterium protoplasts 37° C. to 25° C. (p. 2, left col, last para). (Year: 2011).*

Brandt et al (A Streamlined Protocol for Wheat (*Triticum aestivum*) Protoplast Isolation and Transformation With CRISPR-Cas Ribonucleoprotein Complexes. Frontier in Plant Science 1-14, 2020) (Year: 2020).*

Leblanc et al., "Increased efficiency of targeted mutagenesis by CRISPR/Cas9 in plants using heat stress," *The Plant Journal*, vol. 93, pp. 377-386, 2018.

Fauser et al., "Both CRISPR/Cas-based nucleases and nickases can be used efficiently for genome engineering in *Arabidopsis thaliana,*" *Plant J.*, vol. 79, pp. 348-359, 2014.

Fossi et al., "Development of a Protoplast System for Non-Transgenic, Targeted Genome Editing in *S. tuberosum,*" *13th Annual Solanaceae Conference*, Sep. 12-16, 2016 (1 page).

Gómez and Pallás, "Can the import of mRNA into chloroplasts be mediated by a secondary structure of a small noncoding RNA?" *Plant Signaling & Behavior*, vol. 5, No. 11, pp. 1517-1519, 2010.

Kanchiswamy et al., "Non-GMO genetically edited crop plants," *Trends in Biotechnology*, vol. 33, No. 9, pp. 489-491, 2015.

Kim et al., "CRISPR/Cpf1-mediated DNA-free plant genome editing," *Nature Communications*, 8:14406, 2017 (7 pages).

Kim, "Highly specific genome editing in human cells and plants using CRISPR systems," Seoul National University, thesis, retrieved from: http://s-space.snu.ac.kr/bitstream/10371/125337/1/000000140928.pdf, on Mar. 28, 2018, Feb. 2017 (113 pages).

Komor et al., "Programmable editing of a target base in genomic DNA without double-stranded DNA cleavage," *Nature*, vol. 533, pp. 420-436, 2016.

Liang et al. "Efficient DNA-free genome editing of bread wheat using CRISPR/Cas9 ribonucleoprotein complexes," *Nature Communications*, 8:14261, 2017 (5 pages).

Liang et al., "Genome editing of bread wheat using biolistic delivery of CRISPR/Cas9 in vitro transcripts or ribonucleoproteins," *Nature Protocols*, vol. 13, No. 3, pp. 413-430, 2018.

Lowder et al., "Rapid Evolution of Manifold CRISPR Systems for Plant Genome Editing," *Frontiers in Plant Science*, 7:1683, 2016 (12 pages).

Lu et al., "Arginine-Rich Intracellular Delivery Peptides Synchronously Deliver Covalently and Noncovalently Linked Proteins into Plant Cells," *J. Agric. Food Chem.*, vol. 58, pp. 2288-2294, 2010.

Malnoy et al., "DNA-Free Genetically Edited Grapevine and Apple Protoplast Using CRISPR/Cas9 Ribonucleoproteins," *Frontiers in Plant Science*, 7:1904, 2016 (9 pages).

Mao et al., "Heritability of targeted gene modifications induced by plant-optimized CRISPR systems," *Cellular and Molecular Life Sciences*, vol. 74, pp. 1075-1093, 2017.

Martin-Ortigosa et al., "Mesoporous Silica Nanoparticle-Mediated Intracellular Cre Protein Delivery for Maize Genome Editing via loxP Site Excision," *Plant Physiology*, vol. 164, pp. 537-547, 2014.

Nekrasov et al., "Targeted mutagenesis in the model plant *Nicotiana benthamiana* using Cas9 RNA-guided endonuclease," *Nature Biotechnology*, vol. 31, No. 8, pp. 691-693, 2013.

Niu and Sheen, "Transient Expression Assays for Quantifying Signaling Output," *Plant Signaling Networks: Methods and Protocols, Methods in Molecular Biology*, vol. 876, pp. 195-206, 2012.

O'Brien and Lummis, "Nano-biolistics: a method of biolistic transfection of cells and tissues using a gene gun with novel nanometer-sized projectiles," *BMC Biotechnology*, 11:66, 2011 (6 pages).

Shan et al., "Genome editing in rice and wheat using the CRISPR/Cas system," *Nature Protocols*, vol. 9, No. 10, pp. 2395-2410, 2014.

Subburaj et al., "Site-directed mutagenesis in *Petunia* x *hybrida* protoplast system using direct delivery of purified recombinant Cas9 ribonucleoproteins," *Plant Cell Rep*, vol. 35, pp. 1535-1544, 2016.

Svitashev et al., "Genome editing in maize directed by CRISPR-Cas9 ribonucleoprotein complexes," *Nature Communications*, 7:13274, 2016 (7 pages).

Svitashev et al., "Targeted Mutagenesis, Precise Gene Editing, and Site-Specific Gene Insertion in Maize Using Cas9 and Guide RNA," *Plant Physiology*, vol. 169, pp. 931-945, 2015.

Wolter and Puchta, "Knocking out consumer concerns and regulator's rules: efficient use of CRISPR/Cas ribonucleoprotein complexes for genome editing in cereals," *Genome Biology*, 18:43, 2017 (3 pages).

Woo et al., "DNA-free genome editing in plants with preassembled CRISPR-Cas9 ribonucleoproteins," *Nature Biotechnology*, vol. 33, No. 11, pp. 1162-1165, 2015.

Yin et al., "Progress and prospects in plant genome editing," *Nature Plants*, 3:17107, 2017 (6 pages).

Zhang et al., "Cationic lipids and polymers mediated vectors for delivery of siRNA," *Journal of Controlled Release*, vol. 123, pp. 1-10, 2007.

Zhang et al., "Efficient and transgene-free genome editing in wheat through transient expression of CRISPR/Cas9 DNA or RNA," *Nature Communications*, 7:12617, 2016 (8 pages).

Zong et al., "Precise base editing in rice, wheat and maize with a Cas9-cytidine deaminase fusion," *Nature Biotechnology*, vol. 35, No. 5, pp. 438-441, 2017.

Martin-Ortigosa et al., "Proteolistics: a biolistic method for intracellular delivery of proteins," *Transgenic Res*, vol. 23, pp. 743-756, 2014.

* cited by examiner

Figure 1A

```
NCBI_gi_22123_230        ACTATGCGATTGCTTTCCTGGACCCGTGCAGCTGCGGTGGCATGGGAGGC
CONTIG_230_p1-62.1%      ACTATGCGATTGCTTTCCTGGACCCGTGCAGCTGCGGTGGCATGGGAGGC
CONTIG_229_p2-7.43%      ACTATGCGATTGCTTTCCTGGACCCGTGCAGCTGCGGTGGCATGGGAGGC
CONTIG_228_p3-3.91%      ACTATGCGATTGCTTTCCTGGACCCGTGCAGCTGCGGTGGCATGGGAGGC
CONTIG_229_p4-3.9%       ACTATGCGATTGCTTTCCTGGACCCGTGCAGCTGCGGTGGCATGGGAGGC
CONTIG_227_p5-3.63%      ACTATGCGATTGCTTTCCTGGACCCGTGCAGCTGCGGTGGCATGGGAGGC
CONTIG_226_p6-3.32%      ACTATGCGATTGCTTTCCTGGACCCGTGCAGCTGCGGTGGCATGGGAGGC
CONTIG_225_p7-2.93%      ACTATGCGATTGCTTTCCTGGACCCGTGCAGCTGCGGTGGCATGGGAGGC
CONTIG_224_p8-2.68%      ACTATGCGATTGCTTTCCTGGACCCGTGCAGCTGCGGTGGCATGGGAGGC
CONTIG_231_p9-2.57%      ACTATGCGATTGCTTTCCTGGACCCGTGCAGCTGCGGTGGCATGGGAGGC
CONTIG_231_p10-1.01%     ACTATGCGATTGCTTTCCTGGACCCGTGCAGCTGCGGTGGCATGGGAGGC
CONTIG_224_p11-0.87%     ACTATGCGATTGCTTTCCTGGACCCGTGCAGCTGCGGTGGCATGGGAGGC
CONTIG_227_p12-0.65%     ACTATGCGATTGCTTTCCTGGACCCGTGCAGCTGCGGTGGCATGGGAGGC
CONTIG_222_p13-0.55%     ACTATGCGATTGCTTTCCTGGACCCGTGCAGCTGCGGTGGCATGGGAGGC
CONTIG_226_p14-0.51%     ACTATGCGATTGCTTTCCTGGACCCGTGCAGCTGCGGTGGCATGGGAGGC
CONTIG_223_p15-0.5%      ACTATGCGATTGCTTTCCTGGACCCGTGCAGCTGCGGTGGCATGGGAGGC
CONTIG_220_p16-0.36%     ACTATGCGATTGCTTTCCTGGACCCGTGCAGCTGCGGTGGCATGGGAGGC
CONTIG_229_p17-0.33%     -ATATGCGATTGCTTTCCTGGACCCGTGCAGCTGCGGTGGCATGGGAGGC
CONTIG_228_p18-0.32%     ACTATGCGATTGCTTTCCTGGACCCGTGCAGCTGCGGTGGCATGGGAGGC
CONTIG_231_p19-0.31%     ACTATGCGATTGCTTTCCTGGACCCGTGCAGCTGCGGTGGCATGGGAGGC
CONTIG_221_p20-0.28%     ACTATGCGATTGCTTTCCTGGACCCGTGCAGCTGCGGTGGCATGGGAGGC
CONTIG_229_p21-0.27%     ACTATGCGATTGCTTTCCTGGACCCGTGCAGCTGCGGTGGCATGGGAGGC
CONTIG_221_p22-0.22%     ACTATGCGATTGCTTTCCTGGACCCGTGCAGCTGCGGTGGCATGGGAGGC
CONTIG_227_p23-0.22%     ACTATGCGATTGCTTTCCTGGACCCGTGCAGCTGCGGTGGCATGGGAGGC
CONTIG_228_p24-0.21%     ACTATGCGATTGCTTTCCTGGACCCGTGCAGCTGCGGTGGCATGGGAGGC
CONTIG_225_p25-0.21%     ACTATGCGATTGCTTTCCTGGACCCGTGCAGCTGCGGTGGCATGGGAGGC
CONTIG_237_p26-0.2%      ACTATGCGATTGCTTTCCTGGACCCGTGCAGCTGCGGTGGCATGGGAGGC
CONTIG_263_p27-0.19%     ACTATGCGATTGCTTTCCTGGACCCGTGCAGCTGCGGTGGCATGGGAGGC
CONTIG_221_p28-0.18%     ACTATGCGATTGCTTTCCTGGACCCGTGCAGCTGCGGTGGCATGGGAGGC
                          *************************************************

NCBI_gi_22123_230        CGGCAAGCCACTGTCGATCGAGGAGGTGGAGGTAGCGCCTCCGCAGGCCA
CONTIG_230_p1-62.1%      CGGCAAGCCACTGTCGATCGAGGAGGTGGAGGTAGCGCCTCCGCAGGCCA
CONTIG_229_p2-7.43%      CGGCAAGCCACTGTCGATCGAGGAGGTGGAGGTAGCGCCTCCGCAGGCCA
CONTIG_228_p3-3.91%      CGGCAAGCCACTGTCGATCGAGGAGGTGGAGGTAGCGCCTCCGCAGGCCA
CONTIG_229_p4-3.9%       CGGCAAGCCACTGTCGATCGAGGAGGTGGAGGTAGCGCCTCCGCAGGCCA
CONTIG_227_p5-3.63%      CGGCAAGCCACTGTCGATCGAGGAGGTGGAGGTAGCGCCTCCGCAGGCCA
CONTIG_226_p6-3.32%      CGGCAAGCCACTGTCGATCGAGGAGGTGGAGGTAGCGCCTCCGCAGGCCA
CONTIG_225_p7-2.93%      CGGCAAGCCACTGTCGATCGAGGAGGTGGAGGTAGCGCCTCCGCAGGCCA
CONTIG_224_p8-2.68%      CGGCAAGCCACTGTCGATCGAGGAGGTGGAGGTAGCGCCTCCGCAGGCCA
CONTIG_231_p9-2.57%      CGGCAAGCCACTGTCGATCGAGGAGGTGGAGGTAGCGCCTCCGCAGGCCA
CONTIG_231_p10-1.01%     CGGCAAGCCACTGTCGATCGAGGAGGTGGAGGTAGCGCCTCCGCAGGCCA
CONTIG_224_p11-0.87%     CGGCAAGCCACTGTCGATCGAGGAGGTGGAGGTAGCGCCTCCGCAGGCCA
CONTIG_227_p12-0.65%     CGGCAAGCCACTGTCGATCGAGGAGGTGGAGGTAGCGCCTCCGCAGGCCA
CONTIG_222_p13-0.55%     CGGCAAGCCACTGTCGATCGAGGAGGTGGAGGTAGCGCCTCCGCAGGCCA
CONTIG_226_p14-0.51%     CGGCAAGCCACTGTCGATCGAGGAGGTGGAGGTAGCGCCTCCGCAGGCCA
CONTIG_223_p15-0.5%      CGGCAAGCCACTGTCGATCGAGGAGGTGGAGGTAGCGCCTCCGCAGGCCA
CONTIG_220_p16-0.36%     CGGCAAGCCACTGTCGATCGAGGAGGTGGAGGTAGCGCCTCCGCAGGCCA
CONTIG_229_p17-0.33%     CGGCAAGCCACTGTCGATCGAGGAGGTGGAGGTAGCGCCTCCGCAGGCCA
CONTIG_228_p18-0.32%     CGGCAAGCCACTGTCGATCGAGGAGGTGGAGGTAGCGCCTCCGCAGGCCA
CONTIG_231_p19-0.31%     CGGCAAGCCACTGTCGATCGAGGAGGTGGAGGTAGCGCCTCCGCAGGCCA
CONTIG_221_p20-0.28%     CGGCAAGCCACTGTCGATCGAGGAGGTGGAGGTAGCGCCTCCGCAGGCCA
CONTIG_229_p21-0.27%     CGGCAAGCCACTGTCGATCGAGGAGGTGGAGGTAGCGCCTCCGCAGGCCA
CONTIG_221_p22-0.22%     CGGCAAGCCACTGTCGATCGAGGAGGTGGAGGTAGCGCCTCCGCAGGCCA
CONTIG_227_p23-0.22%     CGGCAAGCCACTGTCGATCGAGGAGGTGGAGGTAGCGCCTCCGCAGGCCA
CONTIG_228_p24-0.21%     CGGCAAGCCACTGTCGATCGAGGAGGTGGAGGTAGCGCCTCCGCAGGCCA
CONTIG_225_p25-0.21%     CGGCAAGCCACTGTCGATCGAGGAGGTGGAGGTAGCGCCTCCGCAGGCCA
CONTIG_237_p26-0.2%      CGGCAAGCCACTGTCGATCGAGGAGGTGGAGGTAGCGCCTCCGCAGGCCA
CONTIG_263_p27-0.19%     CGGCAAGCCACTGTCGATCGAGGAGGTGGAGGTAGCGCCTCCGCAGGCCA
CONTIG_221_p28-0.18%     CGGCAAGCCACTGTCGATCGAGGAGGTGGAGGTAGCGCCTCCGCAGGCCA
                         **************************************************
```

Figure 1B

```
NCBI_gi_22123_230        TGGAGGTGCGCGTCAAGATCCTCTTCACCTCGCTCTGCCACACCGACGT-
CONTIG_230_p1-62.1%      TGGAGGTGCGCGTCAAGATCCTCTTCACCTCGCTCTGCCACACCGACGT-
CONTIG_229_p2-7.43%      TGGAGGTGCGCGTCAAGATCCTCTTCACCTCGCTCTGCCACACCGACG--
CONTIG_228_p3-3.91%      TGGAGGTGCGCGTCAAGATCCTCTTCACCTCGCTCTGCCACACCGACG--
CONTIG_229_p4-3.9%       TGGAGGTGCGCGTCAAGATCCTCTTCACCTCGCTCTGCCACACCGACT--
CONTIG_227_p5-3.63%      TGGAGGTGCGCGTCAAGATCCTCTTCACCTCGCTCTGCCACACCGACG--
CONTIG_226_p6-3.32%      TGGAGGTGCGCGTCAAGATCCTCTTCACCTCGCTCTGCCACACCGACG--
CONTIG_225_p7-2.93%      TGGAGGTGCGCGTCAAGATCCTCTTCACCTCGCTCTGCCACACCGACG--
CONTIG_224_p8-2.68%      TGGAGGTGCGCGTCAAGATCCTCTTCACCTCGCTCTGCCACACCGACG--
CONTIG_231_p9-2.57%      TGGAGGTGCGCGTCAAGATCCTCTTCACCTCGCTCTGCCACACCGACGTT
CONTIG_231_p10-1.01%     TGGAGGTGCGCGTCAAGATCCTCTTCACCTCGCTCTGCCACACCGACGCT
CONTIG_224_p11-0.87%     TGGAGGTGCGCGTCAAGATCCTCTTCACCTCGCTCTGCCACACCGAC---
CONTIG_227_p12-0.65%     TGGAGGTGCGCGTCAAGATCCTCTTCACCTCGCTCTGCCACACCGAC---
CONTIG_222_p13-0.55%     TGGAGGTGCGCGTCAAGATCCTCTTCACCTCGCTCTGCCACACCGACG--
CONTIG_226_p14-0.51%     TGGAGGTGCGCGTCAAGATCCTCTTCACCTCGCTCTGCCACACCGAC---
CONTIG_223_p15-0.5%      TGGAGGTGCGCGTCAAGATCCTCTTCACCTCGCTCTGCCACACCGACG--
CONTIG_220_p16-0.36%     TGGAGGTGCGCGTCAAGATCCTCTTCACCTCGCTCTGCCACACCGAC---
CONTIG_229_p17-0.33%     TGGAGGTGCGCGTCAAGATCCTCTTCACCTCGCTCTGCCACACCGACGT-
CONTIG_228_p18-0.32%     TGGAGGTGCGCGTCAAGATCCTCTTCACCTCGCTCTGCCACACCGACC--
CONTIG_231_p19-0.31%     TGGAGGTGCGCGTCAAGATCCTCTTCACCTCGCTCTGCCACACCGACGAT
CONTIG_221_p20-0.28%     TGGAGGTGCGCGTCAAGATCCTCTTCACCTCGCTCTGCCACACCGAC---
CONTIG_229_p21-0.27%     TGGAGGTGCGCGTCAAGATCCTCTTCACCTCGCTCTGCCACACCGACGT-
CONTIG_221_p22-0.22%     TGGAGGTGCGCGTCAAGATCCTCTTCACCTCGCTCTGCCACACCGACG--
CONTIG_227_p23-0.22%     TGGAGGTGCGCGTCAAGATCCTCTTCACCTCGCTCTGCCACACCGACGT-
CONTIG_228_p24-0.21%     TGGAGGTGCGCGTCAAGATCCTCTTCACCTCGCTCTGCCACACCGAT---
CONTIG_225_p25-0.21%     TGGAGGTGCGCGTCAAGATCCTCTTCACCTCGCTCTGCCACACCGAC---
CONTIG_237_p26-0.2%      TGGAGGTGCGCGTCAAGATCCTCTTCACCTCGCTCTGCCACACCGACGTT
CONTIG_263_p27-0.19%     TGGAGGTGCGCGTCAAGATCCTCTTCACCTCGCTCTGCCACACCGACGGA
CONTIG_221_p28-0.18%     TGGAGGTGCGCGTCAAGATCCTCTTCACCTCGCTCTGCCACACCG-----
                         *********************************************

NCBI_gi_22123_230        -----------------CT-------ACT----TCTG----GGAGGCCAA
CONTIG_230_p1-62.1%      -----------------CT-------ACT----TCTG----GGAGGCCAA
CONTIG_229_p2-7.43%      -----------------CT-------ACT----TCTG----GGAGGCCAA
CONTIG_228_p3-3.91%      ------------------T-------ACT----TCTG----GGAGGCCAA
CONTIG_229_p4-3.9%       -----------------CT-------ACT----TCTG----GGAGGCCAA
CONTIG_227_p5-3.63%      --------------------------ACT----TCTG----GGAGGCCAA
CONTIG_226_p6-3.32%      ---------------------------CT----TCTG----GGAGGCCAA
CONTIG_225_p7-2.93%      ----------------------------T----TCTG----GGAGGCCAA
CONTIG_224_p8-2.68%      ---------------------------------TCTG----GGAGGCCAA
CONTIG_231_p9-2.57%      -----------------CT-------ACT----TCTG----GGAGGCCAA
CONTIG_231_p10-1.01%     -----------------CT-------ACT----TCTG----GGAGGCCAA
CONTIG_224_p11-0.87%     ----------------------------T----TCTG----GGAGGCCAA
CONTIG_227_p12-0.65%     ------------------T-------ACT----TCTG----GGAGGCCAA
CONTIG_222_p13-0.55%     -----------------------------------TG----GGAGGCCAA
CONTIG_226_p14-0.51%     --------------------------ACT----TCTG----GGAGGCCAA
CONTIG_223_p15-0.5%      ----------------------------------CTG----GGAGGCCAA
CONTIG_220_p16-0.36%     ------------------------------------G----GGAGGCCAA
CONTIG_229_p17-0.33%     -----------------CT-------ACT----TCTG----GGAGGCCAA
CONTIG_228_p18-0.32%     ------------------T-------ACT----TCTG----GGAGGCCAA
CONTIG_231_p19-0.31%     -----------------CT-------ACT----TCTG----GGAGGCCAA
CONTIG_221_p20-0.28%     -----------------------------------TG----GGAGGCCAA
CONTIG_229_p21-0.27%     ------------------T-------ACT----TCTG----GGAGGCCAA
CONTIG_221_p22-0.22%     ------------------------------------G----GGAGGCCAA
CONTIG_227_p23-0.22%     ---------------------------CT----TCTG----GGAGGCCAA
CONTIG_228_p24-0.21%     -----------------CT-------ACT----TCTG----GGAGGCCAA
CONTIG_225_p25-0.21%     ---------------------------CT----TCTG----GGAGGCCAA
CONTIG_237_p26-0.2%      TTTTTT-----------CT-------ACT----TCTG----GGAGGCCAA
CONTIG_263_p27-0.19%     AGAAAACCTGATGGAGTCTGCAAAAGACCTGAGACTGGGAGGGAGGCCAA
CONTIG_221_p28-0.18%     ---------------------------------TCTG----GGAGGCCAA
                                                            *    *********
```

Figure 1C

```
NCBI_gi_22123_230      GGTATCTAATCAGCCATCCCATTTGTGATCTTTGTCAGTAGATATGATAC
CONTIG_230_p1-62.1%    GGTATCTAATCAGCCATCCCATTTGTGATCTTTGTCAGTAGATATGATAC
CONTIG_229_p2-7.43%    GGTATCTAATCAGCCATCCCATTTGTGATCTTTGTCAGTAGATATGATAC
CONTIG_228_p3-3.91%    GGTATCTAATCAGCCATCCCATTTGTGATCTTTGTCAGTAGATATGATAC
CONTIG_229_p4-3.9%     GGTATCTAATCAGCCATCCCATTTGTGATCTTTGTCAGTAGATATGATAC
CONTIG_227_p5-3.63%    GGTATCTAATCAGCCATCCCATTTGTGATCTTTGTCAGTAGATATGATAC
CONTIG_226_p6-3.32%    GGTATCTAATCAGCCATCCCATTTGTGATCTTTGTCAGTAGATATGATAC
CONTIG_225_p7-2.93%    GGTATCTAATCAGCCATCCCATTTGTGATCTTTGTCAGTAGATATGATAC
CONTIG_224_p8-2.68%    GGTATCTAATCAGCCATCCCATTTGTGATCTTTGTCAGTAGATATGATAC
CONTIG_231_p9-2.57%    GGTATCTAATCAGCCATCCCATTTGTGATCTTTGTCAGTAGATATGATAC
CONTIG_231_p10-1.01%   GGTATCTAATCAGCCATCCCATTTGTGATCTTTGTCAGTAGATATGATAC
CONTIG_224_p11-0.87%   GGTATCTAATCAGCCATCCCATTTGTGATCTTTGTCAGTAGATATGATAC
CONTIG_227_p12-0.65%   GGTATCTAATCAGCCATCCCATTTGTGATCTTTGTCAGTAGATATGATAC
CONTIG_222_p13-0.55%   GGTATCTAATCAGCCATCCCATTTGTGATCTTTGTCAGTAGATATGATAC
CONTIG_226_p14-0.51%   GGTATCTAATCAGCCATCCCATTTGTGATCTTTGTCAGTAGATATGATAC
CONTIG_223_p15-0.5%    GGTATCTAATCAGCCATCCCATTTGTGATCTTTGTCAGTAGATATGATAC
CONTIG_220_p16-0.36%   GGTATCTAATCAGCCATCCCATTTGTGATCTTTGTCAGTAGATATGATAC
CONTIG_229_p17-0.33%   GGTATCTAATCAGCCATCCCATTTGTGATCTTTGTCAGTAGATATGATAC
CONTIG_228_p18-0.32%   GGTATCTAATCAGCCATCCCATTTGTGATCTTTGTCAGTAGATATGATAC
CONTIG_231_p19-0.31%   GGTATCTAATCAGCCATCCCATTTGTGATCTTTGTCAGTAGATATGATAC
CONTIG_221_p20-0.28%   GGTATCTAATCAGCCATCCCATTTGTGATCTTTGTCAGTAGATATGATAC
CONTIG_229_p21-0.27%   GGTATCTAATCAGCCATCCCATTTGTGATCTTTGTCAGTAGATATGATAC
CONTIG_221_p22-0.22%   GGTATCTAATCAGCCATCCCATTTGTGATCTTTGTCAGTAGATATGATAC
CONTIG_227_p23-0.22%   GGTATCTAATCAGCCATCCCATTTGTGATCTTTGTCAGTAGATATGATAC
CONTIG_228_p24-0.21%   GGTATCTAATCAGCCATCCCATTTGTGATCTTTGTCAGTAGATATGATAC
CONTIG_225_p25-0.21%   GGTATCTAATCAGCCATCCCATTTGTGATCTTTGTCAGTAGATATGATAC
CONTIG_237_p26-0.2%    GGTATCTAATCAGCCATCCCATTTGTGATCTTTGTCAGTAGATATGATAC
CONTIG_263_p27-0.19%   GGTATCTAATCAGCCATCCCATTTGTGATCTTTGTCAGTAGATATGATAC
CONTIG_221_p28-0.18%   GGTATCTAATCAGCCATCCCATTTGTGATCTTTGTCAGTAGATATGATAC
                       **************************************************

NCBI_gi_22123_230      AACAACTCGCGGT    (SEQ ID NO:47)
CONTIG_230_p1-62.1%    AACAACTCGCGGT    (SEQ ID NO:48)
CONTIG_229_p2-7.43%    AACAACTCGCGGT    (SEQ ID NO:49)
CONTIG_228_p3-3.91%    AACAACTCGCGGT    (SEQ ID NO:50)
CONTIG_229_p4-3.9%     AACAACTCGCGGT    (SEQ ID NO:51)
CONTIG_227_p5-3.63%    AACAACTCGCGGT    (SEQ ID NO:52)
CONTIG_226_p6-3.32%    AACAACTCGCGGT    (SEQ ID NO:53)
CONTIG_225_p7-2.93%    AACAACTCGCGGT    (SEQ ID NO:54)
CONTIG_224_p8-2.68%    AACAACTCGCGGT    (SEQ ID NO:55)
CONTIG_231_p9-2.57%    AACAACTCGCGGT    (SEQ ID NO:56)
CONTIG_231_p10-1.01%   AACAACTCGCGGT    (SEQ ID NO:57)
CONTIG_224_p11-0.87%   AACAACTCGCGGT    (SEQ ID NO:58)
CONTIG_227_p12-0.65%   AACAACTCGCGGT    (SEQ ID NO:59)
CONTIG_222_p13-0.55%   AACAACTCGCGGT    (SEQ ID NO:60)
CONTIG_226_p14-0.51%   AACAACTCGCGGT    (SEQ ID NO:61)
CONTIG_223_p15-0.5%    AACAACTCGCGGT    (SEQ ID NO:62)
CONTIG_220_p16-0.36%   AACAACTCGCGGT    (SEQ ID NO:63)
CONTIG_229_p17-0.33%   AACAACTCGCGGT    (SEQ ID NO:64)
CONTIG_228_p18-0.32%   AACAACTCGCGGT    (SEQ ID NO:65)
CONTIG_231_p19-0.31%   AACAACTCGCGGT    (SEQ ID NO:66)
CONTIG_221_p20-0.28%   AACAACTCGCGGT    (SEQ ID NO:67)
CONTIG_229_p21-0.27%   AACAACTCGCGGT    (SEQ ID NO:68)
CONTIG_221_p22-0.22%   AACAACTCGCGGT    (SEQ ID NO:69)
CONTIG_227_p23-0.22%   AACAACTCGCGGT    (SEQ ID NO:70)
CONTIG_228_p24-0.21%   AACAACTCGCGGT    (SEQ ID NO:71)
CONTIG_225_p25-0.21%   AACAACTCGCGGT    (SEQ ID NO:72)
CONTIG_237_p26-0.2%    AACAACTCGCGGT    (SEQ ID NO:73)
CONTIG_263_p27-0.19%   AACAACTCGCGGT    (SEQ ID NO:74)
CONTIG_221_p28-0.18%   AACAACTCGCGGT    (SEQ ID NO:75)
                       *************
```

Figure 2A

```
NCBI_gi_392931134_255 GAAACCTACCAGTCTCTCCTTTGAAGAAGACATGAACAAAATTAGCCACG
CONTIG_256_p1_55.02%  GAAACCTACCAGTCTCTCCTTTGAAGAAAACATGAACAAAATTAGCCACG
CONTIG_256_p2_23.68%  GAAACCTACCAGTCTCTCCTTTGAAGAAAACATGAACAAAATTAGCCACG
CONTIG_255_p3_5.63%   GAAACCTACCAGTCTCTCCTTTGAAGAAAACATGAACAAAATTAGCCACG
CONTIG_257_p4_4.3%    GAAACCTACCAGTCTCTCCTTTGAAGAAAACATGAACAAAATTAGCCACG
CONTIG_250_p5_2.36%   GAAACCTACCAGTCTCTCCTTTGAAGAAAACATGAACAAAATTAGCCACG
CONTIG_257_p6_1.43%   GAAACCTACCAGTCTCTCCTTTGAAGAAAACATGAACAAAATTAGCCACG
CONTIG_257_p7_1.03%   GAAACCTACCAGTCTCTCCTTTGAAGAAAACATGAACAAAATTAGCCACG
CONTIG_254_p8_0.73%   GAAACCTACCAGTCTCTCCTTTGAAGAAAACATGAACAAAATTAGCCACG
CONTIG_255_p9_0.64%   GAAACCTACCAGTCTCTCCTTTGAAGAAAACATGAACAAAATTAGCCACG
CONTIG_255_p10_0.61%  GAAACCTACCAGTCTCTCCTTTGAAGAAAACATGAACAAAATTAGCCACG
CONTIG_253_p11_0.52%  GAAACCTACCAGTCTCTCCTTTGAAGAAAACATGAACAAAATTAGCCACG
CONTIG_252_p12_0.45%  GAAACCTACCAGTCTCTCCTTTGAAGAAAACATGAACAAAATTAGCCACG
CONTIG_257_p13_0.39%  GAAACCTACCAGTCTCTCCTTTGAAGAAAACATGAACAAAATTAGCCACG
CONTIG_249_p14_0.33%  GAAACCTACCAGTCTCTCCTTTGAAGAAAACATGAACAAAATTAGCCACG
CONTIG_249_p15_0.31%  GAAACCTACCAGTCTCTCCTTTGAAGAAAACATGAACAAAATTAGCCACG
CONTIG_257_p16_0.29%  GAAACCTACCAGTCTCTCCTTTGAAGAAAACATGAACAAAATTAGCCACG
CONTIG_252_p17_0.25%  GAAACCTACCAGTCTCTCCTTTGAAGAAAACATGAACAAAATTAGCCACG
CONTIG_251_p18_0.2%   GAAACCTACCAGTCTCTCCTTTGAAGAAAACATGAACAAAATTAGCCACG
CONTIG_253_p19_0.17%  GAAACCTACCAGTCTCTCCTTTGAAGAAAACATGAACAAAATTAGCCACG
CONTIG_255_p20_0.16%  G-AACCTACCAGTCTCTCCTTTGAAGAAAACATGAACAAAATTAGCCACG
CONTIG_247_p21_0.15%  GAAACCTACCAGTCTCTCCTTTGAAGAAAACATGAACAAAATTAGCCACG
CONTIG_248_p22_0.15%  GAAACCTACCAGTCTCTCCTTTGAAGAAAACATGAACAAAATTAGCCACG
CONTIG_251_p23_0.15%  GAAACCTACCAGTCTCTCCTTTGAAGAAAACATGAACAAAATTAGCCACG
CONTIG_245_p24_0.14%  GAAACCTACCAGTCTCTCCTTTGAAGAAAACATGAACAAAATTAGCCACG
CONTIG_257_p25_0.14%  GAAACCTACCAGTCTCTCCTTTGAAGAAAACATGAACAAAATTAGCCACG
CONTIG_257_p26_0.13%  GAAACCTACCAGTCTCTCCTTTGAAGAAAACATGAACAAAATTAGCCACG
CONTIG_253_p27_0.11%  GAAACCTACCAGTCTCTCCTTTGAAGAAAACATGAACAAAATTAGCCACG
CONTIG_254_p28_0.1%   GAAACCTACCAGTCTCTCCTTTGAAGAAAACATGAACAAAATTAGCCACG
CONTIG_251_p29_0.1%   GAAACCTACCAGTCTCTCCTTTGAAGAAAACATGAACAAAATTAGCCACG
CONTIG_254_p30_0.09%  GAAACCTACCAGTCTCTCCTTTGAAGAAAACATGAACAAAATTAGCCACG
CONTIG_249_p31_0.09%  GAAACCTACCAGTCTCTCCTTTGAAGAAAACATGAACAAAATTAGCCACG
                      * ************************** *********************
```

Figure 2B

```
NCBI_gi_392931134_255 GCGCTCTA-TCTCGGCCTTCCG-GTAACGTTTCTTGTTCAATAT-TGTTG
CONTIG_256_p1_55.02%  GCGCTCTC-TCTCGGCCTTCCG-GTAACGTTTCTTGTTCAGTATTTGTTG
CONTIG_256_p2_23.68%  GCGCTCTC-TCTCGGCCTTCCG-GTAATGTTTCTTGTTCAGTATTTGTTG
CONTIG_255_p3_5.63%   GCGCTCTC-TCTCGGCCTTCCG--TAACGTTTCTTGTTCAGTATTTGTTG
CONTIG_257_p4_4.3%    GCGCTCTC-TCTCGGCCTTCCGGGTAACGTTTCTTGTTCAGTATTTGTTG
CONTIG_250_p5_2.36%   GCGCTCTC-TCTCGGCCTTCC-------GTTTCTTGTTCAGTATTTGTTG
CONTIG_257_p6_1.43%   GCGCTCTC-TCTCGGCCTTCCAGGTAACGTTTCTTGTTCAGTATTTGTTG
CONTIG_257_p7_1.03%   GCGCTCTC-TCTCGGCCTTCCGGGTAATGTTTCTTGTTCAGTATTTGTTG
CONTIG_254_p8_0.73%   GCGCTCTC-TCTCGGCCTTCC---TAACGTTTCTTGTTCAGTATTTGTTG
CONTIG_255_p9_0.64%   GCGCTCTC-TCTCGGCCTTCCG--TAATGTTTCTTGTTCAGTATTTGTTG
CONTIG_255_p10_0.61%  GCGCTCTC-TCTCGGCCTTCG--GTAACGTTTCTTGTTCAGTATTTGTTG
CONTIG_253_p11_0.52%  GCGCTCTC-TCTCGGCCTTCCG----ACGTTTCTTGTTCAGTATTTGTTG
CONTIG_252_p12_0.45%  GCGCTCTC-TCTCGGCCTTCCG-----CGTTTCTTGTTCAGTATTTGTTG
CONTIG_257_p13_0.39%  GCGCTCTC-TCTCGGCCTTCCTGGTAACGTTTCTTGTTCAGTATTTGTTG
CONTIG_249_p14_0.33%  GCGCTCTC-TCTCGGCCTTCCG--------TTCTTGTTCAGTATTTGTTG
CONTIG_249_p15_0.31%  GCGCTCTC-TCTCGGCCTTCC--------TTTCTTGTTCAGTATTTGTTG
CONTIG_257_p16_0.29%  GCGCTCTC-TCTCGGCCTTCCCGGTAACGTTTCTTGTTCAGTATTTGTTG
CONTIG_252_p17_0.25%  GCGCTCTC-TCTCGGCCTTCC-----ACGTTTCTTGTTCAGTATTTGTTG
CONTIG_251_p18_0.2%   GCGCTCTC-TCTCGGCCTTCC------CGTTTCTTGTTCAGTATTTGTTG
CONTIG_253_p19_0.17%  GCGCTCTC-TCTCGGCCTTCC----AACGTTTCTTGTTCAGTATTTGTTG
CONTIG_255_p20_0.16%  GCGCTCTC-TCTCGGCCTTCCG-GTAACGTTTCTTGTTCAGTATTTGTTG
CONTIG_247_p21_0.15%  GCGCTCTC-TCTCGGCCTTCC----------TCTTGTTCAGTATTTGTTG
CONTIG_248_p22_0.15%  GCGCTCTC-TCTCGGCCTTCC---------TTCTTGTTCAGTATTTGTTG
CONTIG_251_p23_0.15%  GCGCTCTC-TCTCGGCCTTCCG------GTTTCTTGTTCAGTATTTGTTG
CONTIG_245_p24_0.14%  GCGCTCTC-TCTCGGCCT------------TTCTTGTTCAGTATTTGTTG
CONTIG_257_p25_0.14%  GCGCTCTC-TCTCGGCCTTCCGTGTAACGTTTCTTGTTCAGTATTTGTTG
CONTIG_257_p26_0.13%  GCGCTCTCATCTCGGCCTTCCG-GTAATGTTTCTTGTTCAGTATTTGTTG
CONTIG_253_p27_0.11%  GCGCTCTC-TCTCGGCCTTCCG----ATGTTTCTTGTTCAGTATTTGTTG
CONTIG_254_p28_0.1%   GCGCTCTC-TCTCGGCCTTGG---TAATGTTTCTTGTTCAGTATTTGTTG
CONTIG_251_p29_0.1%   GCGCTCTCTTCTCGGCCTTCC-------GTTTCTTGTTCAGTATTTGTTG
CONTIG_254_p30_0.09%  GCGCTCTC-TCTCGGCCTTCCG---AACGTTTCTTGTTCAGTATTTGTTG
CONTIG_249_p31_0.09%  GCGCTCTC-TCTCGGCCTTCC--------CTTCTTGTTCAGTATTTGTTG
                      *******  *********             ********* *** *****
```

Figure 2C

```
NCBI_gi_392931134_255  TATTTGCTTTCATATGACCAAATTCTTCATAATTAAAGATCGGTATAGAA
CONTIG_256_p1_55.02%   TATTTGCTTTCATATGACCAAATTCTTCATAATTAAAGATCGGTATAGAA
CONTIG_256_p2_23.68%   TATTTGCTTTCATATGACCAAATTCTTCATAATTAAAGATCGGTATAGAA
CONTIG_255_p3_5.63%    TATTTGCTTTCATATGACCAAATTCTTCATAATTAAAGATCGGTATAGAA
CONTIG_257_p4_4.3%     TATTTGCTTTCATATGACCAAATTCTTCATAATTAAAGATCGGTATAGAA
CONTIG_250_p5_2.36%    TATTTGCTTTCATATGACCAAATTCTTCATAATTAAAGATCGGTATAGAA
CONTIG_257_p6_1.43%    TATTTGCTTTCATATGACCAAATTCTTCATAATTAAAGATCGGTATAGAA
CONTIG_257_p7_1.03%    TATTTGCTTTCATATGACCAAATTCTTCATAATTAAAGATCGGTATAGAA
CONTIG_254_p8_0.73%    TATTTGCTTTCATATGACCAAATTCTTCATAATTAAAGATCGGTATAGAA
CONTIG_255_p9_0.64%    TATTTGCTTTCATATGACCAAATTCTTCATAATTAAAGATCGGTATAGAA
CONTIG_255_p10_0.61%   TATTTGCTTTCATATGACCAAATTCTTCATAATTAAAGATCGGTATAGAA
CONTIG_253_p11_0.52%   TATTTGCTTTCATATGACCAAATTCTTCATAATTAAAGATCGGTATAGAA
CONTIG_252_p12_0.45%   TATTTGCTTTCATATGACCAAATTCTTCATAATTAAAGATCGGTATAGAA
CONTIG_257_p13_0.39%   TATTTGCTTTCATATGACCAAATTCTTCATAATTAAAGATCGGTATAGAA
CONTIG_249_p14_0.33%   TATTTGCTTTCATATGACCAAATTCTTCATAATTAAAGATCGGTATAGAA
CONTIG_249_p15_0.31%   TATTTGCTTTCATATGACCAAATTCTTCATAATTAAAGATCGGTATAGAA
CONTIG_257_p16_0.29%   TATTTGCTTTCATATGACCAAATTCTTCATAATTAAAGATCGGTATAGAA
CONTIG_252_p17_0.25%   TATTTGCTTTCATATGACCAAATTCTTCATAATTAAAGATCGGTATAGAA
CONTIG_251_p18_0.2%    TATTTGCTTTCATATGACCAAATTCTTCATAATTAAAGATCGGTATAGAA
CONTIG_253_p19_0.17%   TATTTGCTTTCATATGACCAAATTCTTCATAATTAAAGATCGGTATAGAA
CONTIG_255_p20_0.16%   TATTTGCTTTCATATGACCAAATTCTTCATAATTAAAGATCGGTATAGAA
CONTIG_247_p21_0.15%   TATTTGCTTTCATATGACCAAATTCTTCATAATTAAAGATCGGTATAGAA
CONTIG_248_p22_0.15%   TATTTGCTTTCATATGACCAAATTCTTCATAATTAAAGATCGGTATAGAA
CONTIG_251_p23_0.15%   TATTTGCTTTCATATGACCAAATTCTTCATAATTAAAGATCGGTATAGAA
CONTIG_245_p24_0.14%   TATTTGCTTTCATATGACCAAATTCTTCATAATTAAAGATCGGTATAGAA
CONTIG_257_p25_0.14%   TATTTGCTTTCATATGACCAAATTCTTCATAATTAAAGATCGGTATAGAA
CONTIG_257_p26_0.13%   TATTTGCTTTCATATGACCAAATTCTTCATAATTAAAGATCGGTATAGAA
CONTIG_253_p27_0.11%   TATTTGCTTTCATATGACCAAATTCTTCATAATTAAAGATCGGTATAGAA
CONTIG_254_p28_0.1%    TATTTGCTTTCATATGACCAAATTCTTCATAATTAAAGATCGGTATAGAA
CONTIG_251_p29_0.1%    TATTTGCTTTCATATGACCAAATTCTTCATAATTAAAGATCGGTATAGAA
CONTIG_254_p30_0.09%   TATTTGCTTTCATATGACCAAATTCTTCATAATTAAAGATCGGTATAGAA
CONTIG_249_p31_0.09%   TATTTGCTTTCATATGACCAAATTCTTCATAATTAAAGATCGGTATAGAA
                       **************************************************
```

Figure 2D

```
NCBI_gi_392931134_255 GTCATAGATTACATATATGTACATTTGCACGGGTGAGTTTGCAACAAATG
CONTIG_256_p1_55.02%  GTCATAGATTACATATATGTACATTTGCACGGGTGAGTTTGCAACAAATG
CONTIG_256_p2_23.68%  GTCATAGATTACATATATGTACATTTGCACGGGTGAGTTTGCAACAAATG
CONTIG_255_p3_5.63%   GTCATAGATTACATATATGTACATTTGCACGGGTGAGTTTGCAACAAATG
CONTIG_257_p4_4.3%    GTCATAGATTACATATATGTACATTTGCACGGGTGAGTTTGCAACAAATG
CONTIG_250_p5_2.36%   GTCATAGATTACATATATGTACATTTGCACGGGTGAGTTTGCAACAAATG
CONTIG_257_p6_1.43%   GTCATAGATTACATATATGTACATTTGCACGGGTGAGTTTGCAACAAATG
CONTIG_257_p7_1.03%   GTCATAGATTACATATATGTACATTTGCACGGGTGAGTTTGCAACAAATG
CONTIG_254_p8_0.73%   GTCATAGATTACATATATGTACATTTGCACGGGTGAGTTTGCAACAAATG
CONTIG_255_p9_0.64%   GTCATAGATTACATATATGTACATTTGCACGGGTGAGTTTGCAACAAATG
CONTIG_255_p10_0.61%  GTCATAGATTACATATATGTACATTTGCACGGGTGAGTTTGCAACAAATG
CONTIG_253_p11_0.52%  GTCATAGATTACATATATGTACATTTGCACGGGTGAGTTTGCAACAAATG
CONTIG_252_p12_0.45%  GTCATAGATTACATATATGTACATTTGCACGGGTGAGTTTGCAACAAATG
CONTIG_257_p13_0.39%  GTCATAGATTACATATATGTACATTTGCACGGGTGAGTTTGCAACAAATG
CONTIG_249_p14_0.33%  GTCATAGATTACATATATGTACATTTGCACGGGTGAGTTTGCAACAAATG
CONTIG_249_p15_0.31%  GTCATAGATTACATATATGTACATTTGCACGGGTGAGTTTGCAACAAATG
CONTIG_257_p16_0.29%  GTCATAGATTACATATATGTACATTTGCACGGGTGAGTTTGCAACAAATG
CONTIG_252_p17_0.25%  GTCATAGATTACATATATGTACATTTGCACGGGTGAGTTTGCAACAAATG
CONTIG_251_p18_0.2%   GTCATAGATTACATATATGTACATTTGCACGGGTGAGTTTGCAACAAATG
CONTIG_253_p19_0.17%  GTCATAGATTACATATATGTACATTTGCACGGGTGAGTTTGCAACAAATG
CONTIG_255_p20_0.16%  GTCATAGATTACATATATGTACATTTGCACGGGTGAGTTTGCAACAAATG
CONTIG_247_p21_0.15%  GTCATAGATTACATATATGTACATTTGCACGGGTGAGTTTGCAACAAATG
CONTIG_248_p22_0.15%  GTCATAGATTACATATATGTACATTTGCACGGGTGAGTTTGCAACAAATG
CONTIG_251_p23_0.15%  GTCATAGATTACATATATGTACATTTGCACGGGTGAGTTTGCAACAAATG
CONTIG_245_p24_0.14%  GTCATAGATTACATATATGTACATTTGCACGGGTGAGTTTGCAACAAATG
CONTIG_257_p25_0.14%  GTCATAGATTACATATATGTACATTTGCACGGGTGAGTTTGCAACAAATG
CONTIG_257_p26_0.13%  GTCATAGATTACATATATGTACATTTGCACGGGTGAGTTTGCAACAAATG
CONTIG_253_p27_0.11%  GTCATAGATTACATATATGTACATTTGCACGGGTGAGTTTGCAACAAATG
CONTIG_254_p28_0.1%   GTCATAGATTACATATATGTACATTTGCACGGGTGAGTTTGCAACAAATG
CONTIG_251_p29_0.1%   GTCATAGATTACATATATGTACATTTGCACGGGTGAGTTTGCAACAAATG
CONTIG_254_p30_0.09%  GTCATAGATTACATATATGTACATTTGCACGGGTGAGTTTGCAACAAATG
CONTIG_249_p31_0.09%  GTCATAGATTACATATATGTACATTTGCACGGGTGAGTTTGCAACAAATG
                      **************************************************
```

Figure 2E

```
NCBI_gi_392931134_255 TCGTTTTACTTTGTGAAATTTAATCCCTAATCATGTTTTAGGAATGCTGC
CONTIG_256_p1_55.02%  TCGTTTTACTTTGTGAAATTTAATCCCTAATCATGTTTTAGGAATGCTGC
CONTIG_256_p2_23.68%  TCGTTTTACTTTGTGAAATTTAATCCCTAATCATGTTTTAGGAATGCTGC
CONTIG_255_p3_5.63%   TCGTTTTACTTTGTGAAATTTAATCCCTAATCATGTTTTAGGAATGCTGC
CONTIG_257_p4_4.3%    TCGTTTTACTTTGTGAAATTTAATCCCTAATCATGTTTTAGGAATGCTGC
CONTIG_250_p5_2.36%   TCGTTTTACTTTGTGAAATTTAATCCCTAATCATGTTTTAGGAATGCTGC
CONTIG_257_p6_1.43%   TCGTTTTACTTTGTGAAATTTAATCCCTAATCATGTTTTAGGAATGCTGC
CONTIG_257_p7_1.03%   TCGTTTTACTTTGTGAAATTTAATCCCTAATCATGTTTTAGGAATGCTGC
CONTIG_254_p8_0.73%   TCGTTTTACTTTGTGAAATTTAATCCCTAATCATGTTTTAGGAATGCTGC
CONTIG_255_p9_0.64%   TCGTTTTACTTTGTGAAATTTAATCCCTAATCATGTTTTAGGAATGCTGC
CONTIG_255_p10_0.61%  TCGTTTTACTTTGTGAAATTTAATCCCTAATCATGTTTTAGGAATGCTGC
CONTIG_253_p11_0.52%  TCGTTTTACTTTGTGAAATTTAATCCCTAATCATGTTTTAGGAATGCTGC
CONTIG_252_p12_0.45%  TCGTTTTACTTTGTGAAATTTAATCCCTAATCATGTTTTAGGAATGCTGC
CONTIG_257_p13_0.39%  TCGTTTTACTTTGTGAAATTTAATCCCTAATCATGTTTTAGGAATGCTGC
CONTIG_249_p14_0.33%  TCGTTTTACTTTGTGAAATTTAATCCCTAATCATGTTTTAGGAATGCTGC
CONTIG_249_p15_0.31%  TCGTTTTACTTTGTGAAATTTAATCCCTAATCATGTTTTAGGAATGCTGC
CONTIG_257_p16_0.29%  TCGTTTTACTTTGTGAAATTTAATCCCTAATCATGTTTTAGGAATGCTGC
CONTIG_252_p17_0.25%  TCGTTTTACTTTGTGAAATTTAATCCCTAATCATGTTTTAGGAATGCTGC
CONTIG_251_p18_0.2%   TCGTTTTACTTTGTGAAATTTAATCCCTAATCATGTTTTAGGAATGCTGC
CONTIG_253_p19_0.17%  TCGTTTTACTTTGTGAAATTTAATCCCTAATCATGTTTTAGGAATGCTGC
CONTIG_255_p20_0.16%  TCGTTTTACTTTGTGAAATTTAATCCCTAATCATGTTTTAGGAATGCTGC
CONTIG_247_p21_0.15%  TCGTTTTACTTTGTGAAATTTAATCCCTAATCATGTTTTAGGAATGCTGC
CONTIG_248_p22_0.15%  TCGTTTTACTTTGTGAAATTTAATCCCTAATCATGTTTTAGGAATGCTGC
CONTIG_251_p23_0.15%  TCGTTTTACTTTGTGAAATTTAATCCCTAATCATGTTTTAGGAATGCTGC
CONTIG_245_p24_0.14%  TCGTTTTACTTTGTGAAATTTAATCCCTAATCATGTTTTAGGAATGCTGC
CONTIG_257_p25_0.14%  TCGTTTTACTTTGTGAAATTTAATCCCTAATCATGTTTTAGGAATGCTGC
CONTIG_257_p26_0.13%  TCGTTTTACTTTGTGAAATTTAATCCCTAATCATGTTTTAGGAATGCTGC
CONTIG_253_p27_0.11%  TCGTTTTACTTTGTGAAATTTAATCCCTAATCATGTTTTAGGAATGCTGC
CONTIG_254_p28_0.1%   TCGTTTTACTTTGTGAAATTTAATCCCTAATCATGTTTTAGGAATGCTGC
CONTIG_251_p29_0.1%   TCGTTTTACTTTGTGAAATTTAATCCCTAATCATGTTTTAGGAATGCTGC
CONTIG_254_p30_0.09%  TCGTTTTACTTTGTGAAATTTAATCCCTAATCATGTTTTAGGAATGCTGC
CONTIG_249_p31_0.09%  TCGTTTTACTTTGTGAAATTTAATCCCTAATCATGTTTTAGGAATGCTGC
                      **************************************************
```

Figure 2F

```
NCBI_gi_392931134_255 ACCGTGCC  (SEQ ID NO:76)
CONTIG_256_p1_55.02%  ACCGTGCC  (SEQ ID NO:77)
CONTIG_256_p2_23.68%  ACCGTGCC  (SEQ ID NO:78)
CONTIG_255_p3_5.63%   ACCGTGCC  (SEQ ID NO:79)
CONTIG_257_p4_4.3%    ACCGTGCC  (SEQ ID NO:80)
CONTIG_250_p5_2.36%   ACCGTGCC  (SEQ ID NO:81)
CONTIG_257_p6_1.43%   ACCGTGCC  (SEQ ID NO:82)
CONTIG_257_p7_1.03%   ACCGTGCC  (SEQ ID NO:83)
CONTIG_254_p8_0.73%   ACCGTGCC  (SEQ ID NO:84)
CONTIG_255_p9_0.64%   ACCGTGCC  (SEQ ID NO:85)
CONTIG_255_p10_0.61%  ACCGTGCC  (SEQ ID NO:86)
CONTIG_253_p11_0.52%  ACCGTGCC  (SEQ ID NO:87)
CONTIG_252_p12_0.45%  ACCGTGCC  (SEQ ID NO:88)
CONTIG_257_p13_0.39%  ACCGTGCC  (SEQ ID NO:89)
CONTIG_249_p14_0.33%  ACCGTGCC  (SEQ ID NO:90)
CONTIG_249_p15_0.31%  ACCGTGCC  (SEQ ID NO:91)
CONTIG_257_p16_0.29%  ACCGTGCC  (SEQ ID NO:92)
CONTIG_252_p17_0.25%  ACCGTGCC  (SEQ ID NO:93)
CONTIG_251_p18_0.2%   ACCGTGCC  (SEQ ID NO:94)
CONTIG_253_p19_0.17%  ACCGTGCC  (SEQ ID NO:95)
CONTIG_255_p20_0.16%  ACCGTGCC  (SEQ ID NO:96)
CONTIG_247_p21_0.15%  ACCGTGCC  (SEQ ID NO:97)
CONTIG_248_p22_0.15%  ACCGTGCC  (SEQ ID NO:98)
CONTIG_251_p23_0.15%  ACCGTGCC  (SEQ ID NO:99)
CONTIG_245_p24_0.14%  ACCGTGCC  (SEQ ID NO:100)
CONTIG_257_p25_0.14%  ACCGTGCC  (SEQ ID NO:101)
CONTIG_257_p26_0.13%  ACCGTGCC  (SEQ ID NO:102)
CONTIG_253_p27_0.11%  ACCGTGCC  (SEQ ID NO:103)
CONTIG_254_p28_0.1%   ACCGTGCC  (SEQ ID NO:104)
CONTIG_251_p29_0.1%   ACCGTGCC  (SEQ ID NO:105)
CONTIG_254_p30_0.09%  ACCGTGCC  (SEQ ID NO:106)
CONTIG_249_p31_0.09%  ACCGTGCC  (SEQ ID NO:107)
                      ********
```

Figure 3A

```
NCBI_gi_199580303_202  CCGATGGTCTTCAGTTCTCTTCCTTGTT-ATGGTCTCCCCCACGTGACCC
CONTIG_207_p1_23.91%   CCGATGGTCTTCAGTTCTCTTCCTTGTT-ATGGTCTCCCCCACGTGACCC
CONTIG_205_p2_10.76%   CCGATGGTCTTCAGTTCTCTTCCTTGTT---GGTCTCCCCCACGTGACCC
CONTIG_204_p3_9.83%    CCGATGGTCTTCAGTTCTCTTCCTTGTG----GTCTCCCCCACGTGACCC
CONTIG_208_p4_8.98%    CCGATGGTCTTCAGTTCTCTTCCTTGTTTATGGTCTCCCCCACGTGACCC
CONTIG_206_p5_8.76%    CCGATGGTCTTCAGTTCTCTTCCTTGTA--TGGTCTCCCCCACGTGACCC
CONTIG_206_p6_5.77%    CCGATGGTCTTCAGTTCTCTTCCTTGTT-ATGGTCTCCCCCACGTGACCC
CONTIG_202_p7_5.69%    CCGATGGTCTTCAGTTCTCTTCCTTGT------TCTCCCCCACGTGACCC
CONTIG_201_p8_5.07%    CCGATGGTCTTCAGTTCTCTTCCTTG-------TCTCCCCCACGTGACCC
CONTIG_203_p9_2.64%    CCGATGGTCTTCAGTTCTCTTCCTTGTG----GTCTCCCCCACGTGACCC
CONTIG_204_p10_2.55%   CCGATGGTCTTCAGTTCTCTTCCTTGTT---GGTCTCCCCCACGTGACCC
CONTIG_205_p11_2.26%   CCGATGGTCTTCAGTTCTCTTCCTTGTA--TGGTCTCCCCCACGTGACCC
CONTIG_207_p12_2.25%   CCGATGGTCTTCAGTTCTCTTCCTTGTTTATGGTCTCCCCCACGTGACCC
CONTIG_203_p13_2.13%   CCGATGGTCTTCAGTTCTCTTCCTTGT-----GTCTCCCCCACGTGACCC
CONTIG_201_p14_1.46%   CCGATGGTCTTCAGTTCTCTTCCTTGT------TCTCCCCCACGTGACCC
CONTIG_200_p15_1.24%   CCGATGGTCTTCAGTTCTCTTCCTTG-------TCTCCCCCACGTGACCC
CONTIG_200_p16_1.21%   CCGATGGTCTTCAGTTCTCTTCCTTGT--------TCCCCCACGTGACCC
CONTIG_199_p17_1.2%    CCGATGGTCTTCAGTTCTCTTCCTTGT---------CCCCCACGTGACCC
CONTIG_204_p18_0.89%   CCGATGGTCTTCAGTTCTCTTCCTTGTT----GTCTCCCCCACGTGACCC
CONTIG_208_p19_0.66%   CCGATGGTCTTCAGTTCTCTTCCTTGTATATGGTCTCCCCCACGTGACCC
CONTIG_202_p20_0.46%   CCGATGGTCTTCAGTTCTCTTCCTTGT-----GTCTCCCCCACGTGACCC
CONTIG_203_p21_0.44%   CCGATGGTCTTCAGTTCTCTTCCTTGTT-----TCTCCCCCACGTGACCC
CONTIG_202_p22_0.38%   CCGATGGTCTTCAGTTCTCTTCCTTG------GTCTCCCCCACGTGACCC
CONTIG_206_p23_0.32%   CCGATGGTCTTCAGTTCTCTTCCTTGTT--TGGTCTCCCCCACGTGACCC
CONTIG_198_p24_0.28%   CCGATGGTCTTCAGTTCTCTTCCTTGT----------CCCCACGTGACCC
CONTIG_201_p25_0.28%   CCGATGGTCTTCAGTTCTCTTCCTTGT-------TTCCCCCACGTGACCC
CONTIG_203_p26_0.23%   CCGATGGTCTTCAGTTCTCTTCCTTGTT----GTCTCCCCCACGTGACCC
CONTIG_199_p27_0.21%   CCGATGGTCTTCAGTTCTCTTCCTTGT--------TCCCCCACGTGACCC
                       **************************           *************

NCBI_gi_199580303_202  TCAACAACATAAGGTACTTAACCATA-----ATAAAGCTTCAGATGTTTC
CONTIG_207_p1_23.91%   TCAACAACATAAGGTACTTAACAATAAATAAATAAAGCCTCAGATGTCTC
CONTIG_205_p2_10.76%   TCAACAACATAAGGTACTTAACAATAAATAAATAAAGCCTCAGATGTCTC
CONTIG_204_p3_9.83%    TCAACAACATAAGGTACTTAACAATAAATAAATAAAGCCTCAGATGTCTC
CONTIG_208_p4_8.98%    TCAACAACATAAGGTACTTAACAATAAATAAATAAAGCCTCAGATGTCTC
CONTIG_206_p5_8.76%    TCAACAACATAAGGTACTTAACAATAAATAAATAAAGCCTCAGATGTCTC
CONTIG_206_p6_5.77%    TCAACAACATAAGGTACTTAACAATA-ATAAATAAAGCCTCAGATGTCTC
CONTIG_202_p7_5.69%    TCAACAACATAAGGTACTTAACAATAAATAAATAAAGCCTCAGATGTCTC
CONTIG_201_p8_5.07%    TCAACAACATAAGGTACTTAACAATAAATAAATAAAGCCTCAGATGTCTC
CONTIG_203_p9_2.64%    TCAACAACATAAGGTACTTAACAATA-ATAAATAAAGCCTCAGATGTCTC
CONTIG_204_p10_2.55%   TCAACAACATAAGGTACTTAACAATA-ATAAATAAAGCCTCAGATGTCTC
CONTIG_205_p11_2.26%   TCAACAACATAAGGTACTTAACAATA-ATAAATAAAGCCTCAGATGTCTC
CONTIG_207_p12_2.25%   TCAACAACATAAGGTACTTAACAATA-ATAAATAAAGCCTCAGATGTCTC
CONTIG_203_p13_2.13%   TCAACAACATAAGGTACTTAACAATAAATAAATAAAGCCTCAGATGTCTC
CONTIG_201_p14_1.46%   TCAACAACATAAGGTACTTAACAATA-ATAAATAAAGCCTCAGATGTCTC
CONTIG_200_p15_1.24%   TCAACAACATAAGGTACTTAACAATA-ATAAATAAAGCCTCAGATGTCTC
CONTIG_200_p16_1.21%   TCAACAACATAAGGTACTTAACAATAAATAAATAAAGCCTCAGATGTCTC
CONTIG_199_p17_1.2%    TCAACAACATAAGGTACTTAACAATAAATAAATAAAGCCTCAGATGTCTC
CONTIG_204_p18_0.89%   TCAACAACATAAGGTACTTAACAATAAATAAATAAAGCCTCAGATGTCTC
CONTIG_208_p19_0.66%   TCAACAACATAAGGTACTTAACAATAAATAAATAAAGCCTCAGATGTCTC
CONTIG_202_p20_0.46%   TCAACAACATAAGGTACTTAACAATA-ATAAATAAAGCCTCAGATGTCTC
CONTIG_203_p21_0.44%   TCAACAACATAAGGTACTTAACAATAAATAAATAAAGCCTCAGATGTCTC
CONTIG_202_p22_0.38%   TCAACAACATAAGGTACTTAACAATAAATAAATAAAGCCTCAGATGTCTC
CONTIG_206_p23_0.32%   TCAACAACATAAGGTACTTAACAATAAATAAATAAAGCCTCAGATGTCTC
CONTIG_198_p24_0.28%   TCAACAACATAAGGTACTTAACAATAAATAAATAAAGCCTCAGATGTCTC
CONTIG_201_p25_0.28%   TCAACAACATAAGGTACTTAACAATAAATAAATAAAGCCTCAGATGTCTC
CONTIG_203_p26_0.23%   TCAACAACATAAGGTACTTAACAATA-ATAAATAAAGCCTCAGATGTCTC
CONTIG_199_p27_0.21%   TCAACAACATAAGGTACTTAACAATA-ATAAATAAAGCCTCAGATGTCTC
                       ********************** ***     ******* ******** **
```

Figure 3B

```
NCBI_gi_199580303_202  ATCCATGAACCGCTGCTGATTGTCTTTCTCCTTAGGATCAAGTCGTTGCT
CONTIG_207_p1_23.91%   ATCCATGAACCGGTGCTGATTGTCTTTCTCCTTAGGATCAAGTCGTTGCT
CONTIG_205_p2_10.76%   ATCCATGAACCGGTGCTGATTGTCTTTCTCCTTAGGATCAAGTCGTTGCT
CONTIG_204_p3_9.83%    ATCCATGAACCGGTGCTGATTGTCTTTCTCCTTAGGATCAAGTCGTTGCT
CONTIG_208_p4_8.98%    ATCCATGAACCGGTGCTGATTGTCTTTCTCCTTAGGATCAAGTCGTTGCT
CONTIG_206_p5_8.76%    ATCCATGAACCGGTGCTGATTGTCTTTCTCCTTAGGATCAAGTCGTTGCT
CONTIG_206_p6_5.77%    ATCCATGAACCGGTGCTGATTGTCTTTCTCCTTAGGATCAAGTCGTTGCT
CONTIG_202_p7_5.69%    ATCCATGAACCGGTGCTGATTGTCTTTCTCCTTAGGATCAAGTCGTTGCT
CONTIG_201_p8_5.07%    ATCCATGAACCGGTGCTGATTGTCTTTCTCCTTAGGATCAAGTCGTTGCT
CONTIG_203_p9_2.64%    ATCCATGAACCGGTGCTGATTGTCTTTCTCCTTAGGATCAAGTCGTTGCT
CONTIG_204_p10_2.55%   ATCCATGAACCGGTGCTGATTGTCTTTCTCCTTAGGATCAAGTCGTTGCT
CONTIG_205_p11_2.26%   ATCCATGAACCGGTGCTGATTGTCTTTCTCCTTAGGATCAAGTCGTTGCT
CONTIG_207_p12_2.25%   ATCCATGAACCGGTGCTGATTGTCTTTCTCCTTAGGATCAAGTCGTTGCT
CONTIG_203_p13_2.13%   ATCCATGAACCGGTGCTGATTGTCTTTCTCCTTAGGATCAAGTCGTTGCT
CONTIG_201_p14_1.46%   ATCCATGAACCGGTGCTGATTGTCTTTCTCCTTAGGATCAAGTCGTTGCT
CONTIG_200_p15_1.24%   ATCCATGAACCGGTGCTGATTGTCTTTCTCCTTAGGATCAAGTCGTTGCT
CONTIG_200_p16_1.21%   ATCCATGAACCGGTGCTGATTGTCTTTCTCCTTAGGATCAAGTCGTTGCT
CONTIG_199_p17_1.2%    ATCCATGAACCGGTGCTGATTGTCTTTCTCCTTAGGATCAAGTCGTTGCT
CONTIG_204_p18_0.89%   ATCCATGAACCGGTGCTGATTGTCTTTCTCCTTAGGATCAAGTCGTTGCT
CONTIG_208_p19_0.66%   ATCCATGAACCGGTGCTGATTGTCTTTCTCCTTAGGATCAAGTCGTTGCT
CONTIG_202_p20_0.46%   ATCCATGAACCGGTGCTGATTGTCTTTCTCCTTAGGATCAAGTCGTTGCT
CONTIG_203_p21_0.44%   ATCCATGAACCGGTGCTGATTGTCTTTCTCCTTAGGATCAAGTCGTTGCT
CONTIG_202_p22_0.38%   ATCCATGAACCGGTGCTGATTGTCTTTCTCCTTAGGATCAAGTCGTTGCT
CONTIG_206_p23_0.32%   ATCCATGAACCGGTGCTGATTGTCTTTCTCCTTAGGATCAAGTCGTTGCT
CONTIG_198_p24_0.28%   ATCCATGAACCGGTGCTGATTGTCTTTCTCCTTAGGATCAAGTCGTTGCT
CONTIG_201_p25_0.28%   ATCCATGAACCGGTGCTGATTGTCTTTCTCCTTAGGATCAAGTCGTTGCT
CONTIG_203_p26_0.23%   ATCCATGAACCGGTGCTGATTGTCTTTCTCCTTAGGATCAAGTCGTTGCT
CONTIG_199_p27_0.21%   ATCCATGAACCGGTGCTGATTGTCTTTCTCCTTAGGATCAAGTCGTTGCT
                       ************ *************************************

NCBI_gi_199580303_202  TATGTCGAATACTTTGGTCAGTTCACATCAGAGCAATTCCCTGATGATAT
CONTIG_207_p1_23.91%   TATGTCGAATACTTTGGTCAGTTCACATCAGAGCAATTCCCTGATGATAT
CONTIG_205_p2_10.76%   TATGTCGAATACTTTGGTCAGTTCACATCAGAGCAATTCCCTGATGATAT
CONTIG_204_p3_9.83%    TATGTCGAATACTTTGGTCAGTTCACATCAGAGCAATTCCCTGATGATAT
CONTIG_208_p4_8.98%    TATGTCGAATACTTTGGTCAGTTCACATCAGAGCAATTCCCTGATGATAT
CONTIG_206_p5_8.76%    TATGTCGAATACTTTGGTCAGTTCACATCAGAGCAATTCCCTGATGATAT
CONTIG_206_p6_5.77%    TATGTCGAATACTTTGGTCAGTTCACATCAGAGCAATTCCCTGATGATAT
CONTIG_202_p7_5.69%    TATGTCGAATACTTTGGTCAGTTCACATCAGAGCAATTCCCTGATGATAT
CONTIG_201_p8_5.07%    TATGTCGAATACTTTGGTCAGTTCACATCAGAGCAATTCCCTGATGATAT
CONTIG_203_p9_2.64%    TATGTCGAATACTTTGGTCAGTTCACATCAGAGCAATTCCCTGATGATAT
CONTIG_204_p10_2.55%   TATGTCGAATACTTTGGTCAGTTCACATCAGAGCAATTCCCTGATGATAT
CONTIG_205_p11_2.26%   TATGTCGAATACTTTGGTCAGTTCACATCAGAGCAATTCCCTGATGATAT
CONTIG_207_p12_2.25%   TATGTCGAATACTTTGGTCAGTTCACATCAGAGCAATTCCCTGATGATAT
CONTIG_203_p13_2.13%   TATGTCGAATACTTTGGTCAGTTCACATCAGAGCAATTCCCTGATGATAT
CONTIG_201_p14_1.46%   TATGTCGAATACTTTGGTCAGTTCACATCAGAGCAATTCCCTGATGATAT
CONTIG_200_p15_1.24%   TATGTCGAATACTTTGGTCAGTTCACATCAGAGCAATTCCCTGATGATAT
CONTIG_200_p16_1.21%   TATGTCGAATACTTTGGTCAGTTCACATCAGAGCAATTCCCTGATGATAT
CONTIG_199_p17_1.2%    TATGTCGAATACTTTGGTCAGTTCACATCAGAGCAATTCCCTGATGATAT
CONTIG_204_p18_0.89%   TATGTCGAATACTTTGGTCAGTTCACATCAGAGCAATTCCCTGATGATAT
CONTIG_208_p19_0.66%   TATGTCGAATACTTTGGTCAGTTCACATCAGAGCAATTCCCTGATGATAT
CONTIG_202_p20_0.46%   TATGTCGAATACTTTGGTCAGTTCACATCAGAGCAATTCCCTGATGATAT
CONTIG_203_p21_0.44%   TATGTCGAATACTTTGGTCAGTTCACATCAGAGCAATTCCCTGATGATAT
CONTIG_202_p22_0.38%   TATGTCGAATACTTTGGTCAGTTCACATCAGAGCAATTCCCTGATGATAT
CONTIG_206_p23_0.32%   TATGTCGAATACTTTGGTCAGTTCACATCAGAGCAATTCCCTGATGATAT
CONTIG_198_p24_0.28%   TATGTCGAATACTTTGGTCAGTTCACATCAGAGCAATTCCCTGATGATAT
CONTIG_201_p25_0.28%   TATGTCGAATACTTTGGTCAGTTCACATCAGAGCAATTCCCTGATGATAT
CONTIG_203_p26_0.23%   TATGTCGAATACTTTGGTCAGTTCACATCAGAGCAATTCCCTGATGATAT
CONTIG_199_p27_0.21%   TATGTCGAATACTTTGGTCAGTTCACATCAGAGCAATTCCCTGATGATAT
                       **************************************************
```

Figure 3C

| | | |
|---|---|---|
| NCBI_gi_199580303_202 | TGCTGAGG | (SEQ ID NO:108) |
| CONTIG_207_p1_23.91% | TGCTGAGG | (SEQ ID NO:109) |
| CONTIG_205_p2_10.76% | TGCTGAGG | (SEQ ID NO:110) |
| CONTIG_204_p3_9.83% | TGCTGAGG | (SEQ ID NO:111) |
| CONTIG_208_p4_8.98% | TGCTGAGG | (SEQ ID NO:112) |
| CONTIG_206_p5_8.76% | TGCTGAGG | (SEQ ID NO:113) |
| CONTIG_206_p6_5.77% | TGCTGAGG | (SEQ ID NO:114) |
| CONTIG_202_p7_5.69% | TGCTGAGG | (SEQ ID NO:115) |
| CONTIG_201_p8_5.07% | TGCTGAGG | (SEQ ID NO:116) |
| CONTIG_203_p9_2.64% | TGCTGAGG | (SEQ ID NO:117) |
| CONTIG_204_p10_2.55% | TGCTGAGG | (SEQ ID NO:118) |
| CONTIG_205_p11_2.26% | TGCTGAGG | (SEQ ID NO:119) |
| CONTIG_207_p12_2.25% | TGCTGAGG | (SEQ ID NO:120) |
| CONTIG_203_p13_2.13% | TGCTGAGG | (SEQ ID NO:121) |
| CONTIG_201_p14_1.46% | TGCTGAGG | (SEQ ID NO:122) |
| CONTIG_200_p15_1.24% | TGCTGAGG | (SEQ ID NO:123) |
| CONTIG_200_p16_1.21% | TGCTGAGG | (SEQ ID NO:124) |
| CONTIG_199_p17_1.2% | TGCTGAGG | (SEQ ID NO:125) |
| CONTIG_204_p18_0.89% | TGCTGAGG | (SEQ ID NO:126) |
| CONTIG_208_p19_0.66% | TGCTGAGG | (SEQ ID NO:127) |
| CONTIG_202_p20_0.46% | TGCTGAGG | (SEQ ID NO:128) |
| CONTIG_203_p21_0.44% | TGCTGAGG | (SEQ ID NO:129) |
| CONTIG_202_p22_0.38% | TGCTGAGG | (SEQ ID NO:130) |
| CONTIG_206_p23_0.32% | TGCTGAGG | (SEQ ID NO:131) |
| CONTIG_198_p24_0.28% | TGCTGAGG | (SEQ ID NO:132) |
| CONTIG_201_p25_0.28% | TGCTGAGG | (SEQ ID NO:133) |
| CONTIG_203_p26_0.23% | TGCTGAGG | (SEQ ID NO:134) |
| CONTIG_199_p27_0.21% | TGCTGAGG | (SEQ ID NO:135) |
| | ******** | |

METHODS OF ALTERING A TARGET NUCLEOTIDE SEQUENCE WITH AN RNA-GUIDED NUCLEASE AND A SINGLE GUIDE RNA

PRIORITY CLAIMS AND RELATED APPLICATIONS

This application claims the benefit of priority to U.S. Provisional Patent Application 62/440,676, filed on 30 Dec. 2016, which is incorporated by reference in its entirety herein.

INCORPORATION OF SEQUENCE LISTING

The sequence listing contained in the file named "10002P1_ST25.txt", which is 142 kilobytes measured in operating system Windows 7 x64, and which was created on 29 Dec. 2017 is incorporated herein by reference in its entirety.

FIELD

Aspects of this invention relate to agricultural biotechnology. Disclosed herein are novel plant cells, plants and seeds derived from such plant cells and having enhanced traits, and methods of making and using such plant cells and derived plants and seeds.

BACKGROUND

Recent advances in genome editing technologies have provided opportunities for precise modification of the genome in many types of organisms, including plants and animals. For example, technologies based on genome editing proteins, such as zinc finger nucleases, TALENs, and CRISPR systems are advancing rapidly and it is now possible to target genetic changes to specific DNA sequences in the genome.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Other CRISPR nucleases useful for editing genomes include C2c1 and C2c3 (see Shmakov et al. (2015) *Mol. Cell,* 60:385-397) and CasX and CasY (see Burstein et al. (2016) *Nature*, doi:10.1038/nature21059). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246).

SUMMARY

Disclosed herein are methods for providing novel plant cells or plant protoplasts, plant callus, tissues or parts, whole plants, and seeds having one or more altered genetic sequences.

In one aspect, the invention provides a method of delivering a guide RNA (gRNA) (or other sequence-editing guide nucleic acid capable of directing a nuclease to a specific target sequence) to a plant cell or plant protoplast. The gRNA can be provided as a CRISPR RNA (crRNA) or as a single guide RNA (sgRNA) or as a polynucleotide that encodes or is processed to a crRNA or sgRNA, wherein the gRNA has a nucleotide sequence designed to alter a target nucleotide sequence in the plant cell or plant protoplast. In embodiments, the plant cell or plant protoplast is a cell capable of division and differentiation. In embodiments, the plant cell or plant protoplast is obtained from a monocot plant or in a dicot plant, and can be haploid or diploid. In embodiments, the plant cell or plant protoplast contains a nuclease, such as a Cas9 nuclease or other RNA-guided nuclease, that is capable of altering the target nucleotide sequence; in other embodiments the nuclease is provided to the plant cell or plant protoplast, either together with the crRNA (or other genome-editing polynucleotide) or separately. The nuclease can be provided as a functional enzyme (e. g., as a ribonucleoprotein or micelle or other molecular or supramolecular complex), or as a polynucleotide that encodes the functional nuclease. The target nucleotide sequence is one or more nucleotide sequences, including protein-coding sequence or non-coding sequence or a combination thereof. Embodiments include a plant nuclear sequence, a plant plastid sequence, a plant mitochondrial sequence, a sequence of a symbiont, pest, or pathogen of a plant, and combinations thereof. The crRNA (or other sequence-editing polynucleotide) and the RNA-guided nuclease are provided separately (e. g., in discrete compositions or in discrete steps), or alternatively are provided simultaneously (e. g., combined in a single composition, or in a single step or treatment). Embodiments of the method include one or more delivery steps or treatments, including treatment with at least one chemical, enzymatic, or physical agent or use of techniques such as application of heat or cold, ultrasonication, centrifugation, and electroporation, whereby the gRNA is delivered to the plant cell or plant protoplast. In embodiments, the method further includes growing or regeneration of a seedling, plantlet, or plant from the plant cell or plant protoplast having the altered target nucleotide sequence. Related aspects include: compositions including a plant cell or plant protoplast and at least one gRNA, the plant cell or plant protoplast with the altered target nucleotide sequence provided by the method; pluralities, arrays, and heterogeneous populations of such plant cells or plant protoplasts; and callus, seedlings, plantlets, and plants and their seeds, grown or regenerated from the plant cell or plant protoplast and having the altered target nucleotide sequence, and pluralities, arrays, and heterogeneous populations thereof.

In another aspect, the invention provides a method of providing a plant cell or plant protoplast having a genetic alteration, including the step of delivering an effector molecule such as a sequence-specific nuclease or a guide nucleic acid to a plant cell or plant protoplast, resulting in a genetic alteration of the plant cell or plant protoplast; related methods further include the step of growing or regenerating a plant from the resulting genetically altered plant cell or plant protoplast, wherein the plant includes differentiated cells or tissues having the genetic alteration. In various embodiments, the plant cell or plant protoplast is an isolated plant cell or isolated plant protoplast, is monocot or dicot, is haploid or diploid, and is capable of division and differentiation or capable of growth or regeneration into callus, a seedling, a plantlet, or a plant. In related embodiments, the plant cell or plant protoplast is in, or is isolated from, a plant or part of a plant. Embodiments include those wherein the effector molecule is at least one selected from the group consisting of: a polynucleotide, a ribonucleoprotein, a polypeptide (for example, a protein, an enzyme, or a nuclease), and a polynucleotide encoding a polypeptide; or a combination thereof. Embodiments of the method include one or more delivery steps or treatments, including treatment with chemical or physical agents or use of techniques such as application of heat or cold, ultrasonication, centrifugation, and electroporation. Related aspects include plants having a genetic alteration provided by the method, heterogeneous populations or libraries of such plants, succeeding generations or seeds of such plants, parts of the plants, or products (such as processed products or commodity products) made from the plants or their seeds.

In another aspect, the invention provides a method of identifying a nucleotide sequence (or alteration of a nucleotide sequence) associated with a phenotype of interest, including altering the genome of a population of plant cells or protoplasts, optionally growing or regenerating a population of calli, seedlings, plantlets, or plants from the population of plant cells or protoplasts, and selecting the plant cells or protoplasts (or calli, seedlings, plantlets, or plants) exhibiting the phenotype of interest. Embodiments of the method include culturing or growing the plant cells or protoplasts (or calli, seedlings, plantlets, or plants) under conditions that permit expression of the phenotype of interest. Related aspects include compositions including (a) a population of plant cells or plant protoplasts, a library of gRNAs, and an RNA-guided nuclease, or (b) a population of plant cells or plant protoplasts and at least one double-stranded break (DSB)-inducing effector molecule (e. g., at least one gRNA, or both at least one gRNA and an RNA-guided nuclease).

BRIEF DESCRIPTION OF THE DRAWINGS

FIGS. 1A-1C depict the Clustal-W multiple-sequence alignment of the next-generation sequencing reads of the maize (*Zea mays*) alcohol dehydrogenase ADH1 that were amplified and sequenced as described in detail in Example 4. Sequencing reads are identified by a number beginning with the letter P and are listed from highest to lowest percentage of total NGS reads. P1 identifies the non-edited sequence, i. e., identical to the reference sequence identified at the beginning of the list by an "NCBI_gi" number (NCBI accession number). Asterisks in the last line of the alignment indicate conserved nucleotides.

FIGS. 2A-2F depict the Clustal-W multiple-sequence alignment of the next-generation sequencing reads of the kale (*Brassica oleracea*) Myb-like transcription factor 2, BoMYBL2 that were amplified and sequenced as described in detail in Example 5. Sequencing reads are identified by a number beginning with the letter P and are listed from highest to lowest percentage of total NGS reads. P1 identifies the non-edited sequence, i. e., identical to the reference sequence identified at the beginning of the list by an "NCBI_gi" number (NCBI accession number). Asterisks in the last line of the alignment indicate conserved nucleotides.

FIGS. 3A-3C depict the Clustal-W multiple-sequence alignment of the next-generation sequencing reads of the kale (*Brassica oleracea*) "*Gigantea*" gene BoGI that were amplified and sequenced as described in detail in Example 5. Sequencing reads are identified by a number beginning with the letter P and are listed from highest to lowest percentage of total NGS reads. P1 identifies the non-edited sequence, i. e., identical to the reference sequence identified at the beginning of the list by an "NCBI_gi" number (NCBI accession number). Asterisks in the last line of the alignment indicate conserved nucleotides.

DETAILED DESCRIPTION OF THE INVENTION

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art. Where a term is provided in the singular, the inventors also contemplate aspects of the invention described by the plural of that term.

By "polynucleotide" is meant a nucleic acid molecule containing multiple nucleotides and refers to "oligonucleotides" (defined here as a polynucleotide molecule of between 2-25 nucleotides in length) and polynucleotides of 26 or more nucleotides. Polynucleotides are generally described as single- or double-stranded. Where a polynucleotide contains double-stranded regions formed by intra- or intermolecular hybridization, the length of each double-stranded region is conveniently described in terms of the number of base pairs. Aspects of this invention include the use of polynucleotides or compositions containing polynucleotides; embodiments include one or more oligonucleotides or polynucleotides or a mixture of both, including single- or double-stranded RNA or single- or double-stranded DNA or double-stranded DNA/RNA hybrids or chemically modified analogues or a mixture thereof. In various embodiments, the polynucleotide includes a combination of ribonucleotides and deoxyribonucleotides (e. g., synthetic polynucleotides consisting mainly of ribonucleotides but with one or more terminal deoxyribonucleotides or synthetic polynucleotides consisting mainly of deoxyribonucleotides but with one or more terminal dideoxyribonucleotides), or includes non-canonical nucleotides such as inosine, thiouridine, or pseudouridine. In embodiments, the polynucleotide includes chemically modified nucleotides (see, e. g., Verma and Eckstein (1998) *Annu. Rev. Biochem.,* 67:99-134); for example, the naturally occurring phosphodiester backbone of an oligonucleotide or polynucleotide can be partially or completely modified with phosphorothioate, phosphorodithioate, or methylphosphonate internucleotide linkage modifications, modified nucleoside bases or modified sugars can be used in oligonucleotide or polynucleotide synthesis, and oligonucleotides or polynucleotides can be labelled with a fluorescent moiety (e. g., fluorescein or rhodamine) or other label (e. g., biotin). Modified nucleic acids, particularly modified RNAs, are disclosed in U.S. Pat. No. 9,464,124, incorporated by reference in its entirety herein.

CRISPR (Clustered Regularly Interspaced Short Palindromic Repeats)/Cas (CRISPR-associated) systems, or CRISPR systems, are adaptive defense systems originally discovered in bacteria and archaea. CRISPR systems use RNA-guided nucleases termed CRISPR-associated or "Cas" endonucleases (e. g., Cas9 or Cpf1) to cleave foreign DNA. In a typical CRISPR/Cas system, a Cas endonuclease is directed to a target nucleotide sequence (e. g., a site in the genome that is to be sequence-edited) by sequence-specific, non-coding "guide RNAs" that target single- or double-stranded DNA sequences. In microbial hosts, CRISPR loci encode both Cas endonucleases and "CRISPR arrays" of the non-coding RNA elements that determine the specificity of the CRISPR-mediated nucleic acid cleavage.

Three classes (I-III) of CRISPR systems have been identified across a wide range of bacterial hosts. The well characterized class II CRISPR systems use a single Cas endonuclease (rather than multiple Cas proteins). One class II CRISPR system includes a type II Cas endonuclease such as Cas9, a CRISPR RNA ("crRNA"), and a trans-activating crRNA ("tracrRNA"). The crRNA contains a "guide RNA", typically a 20-nucleotide RNA sequence that corresponds to (i. e., is identical or nearly identical to, or alternatively is complementary or nearly complementary to) a 20-nucleotide target DNA sequence. The crRNA also contains a region that binds to the tracrRNA to form a partially double-stranded structure which is cleaved by RNase III, resulting in a crRNA/tracrRNA hybrid. The crRNA/tracrRNA hybrid then directs the Cas9 endonuclease to recognize and cleave the target DNA sequence.

The target DNA sequence must generally be adjacent to a "protospacer adjacent motif" ("PAM") that is specific for a given Cas endonuclease; however, PAM sequences are short and relatively non-specific, appearing throughout a given genome. CRISPR endonucleases identified from various prokaryotic species have unique PAM sequence requirements; examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), and 5'-NNNGATT (*Neisseria meningitidis*). Some endonucleases, e. g., Cas9 endonucleases, are associated with G-rich PAM sites, e. g., 5'-NGG, and perform blunt-end cleaving of the target DNA at a location 3 nucleotides upstream from (5' from) the PAM site.

Another class II CRISPR system includes the type V endonuclease Cpf1, which is a smaller endonuclease than is Cas9; examples include AsCpf1 (from *Acidaminococcus* sp.) and LbCpf1 (from *Lachnospiraceae* sp.). Cpf1-associated CRISPR arrays are processed into mature crRNAs without the requirement of a tracrRNA; in other words, a Cpf1 system requires only the Cpf1 nuclease and a crRNA to cleave the target DNA sequence. Cpf1 endonucleases, are associated with T-rich PAM sites, e. g., 5'-TTN. Cpf1 can also recognize a 5'-CTA PAM motif. Cpf1 cleaves the target DNA by introducing an offset or staggered double-strand break with a 4- or 5-nucleotide 5' overhang, for example, cleaving a target DNA with a 5-nucleotide offset or staggered cut located 18 nucleotides downstream from (3' from) from the PAM site on the coding strand and 23 nucleotides downstream from the PAM site on the complimentary strand; the 5-nucleotide overhang that results from such offset cleavage allows more precise genome editing by DNA insertion by homologous recombination than by insertion at blunt-end cleaved DNA. See, e. g., Zetsche et al. (2015) Cell, 163:759-771. Other CRISPR nucleases useful in methods and compositions of the invention include C2c1 and C2c3 (see Shmakov et al. (2015) *Mol. Cell,* 60:385-397) and CasX and CasY (see Burstein et al. (2016) *Nature*, doi: 10.1038/nature21059). Like other CRISPR nucleases, C2c1 from *Alicyclobacillus acidoterrestris* (AacC2c1) requires a guide RNA and PAM recognition site; C2c1 cleavage results in a staggered seven-nucleotide DSB in the target DNA (see Yang et al. (2016) Cell, 167:1814-1828.e12) and is reported to have high mismatch sensitivity, thus reducing off-target effects (see Liu et al. (2016) Mol. Cell, available on line at dx[dot]doi[dot]org/10[dot]1016/j[dot]molcel[dot]2016[dot]11.040). Yet other CRISPR nucleases include nucleases identified from the genomes of uncultivated microbes, such as CasX and CasY; see Burstein et al. (2016) *Nature*, doi:10.1038/nature21059.

For the purposes of gene editing, CRISPR arrays can be designed to contain one or multiple guide RNA sequences corresponding to a desired target DNA sequence; see, for example, Cong et al. (2013) Science, 339:819-823; Ran et al. (2013) *Nature Protocols,* 8:2281-2308. At least 16 or 17 nucleotides of gRNA sequence are required by Cas9 for DNA cleavage to occur; for Cpf1 at least 16 nucleotides of gRNA sequence are needed to achieve detectable DNA cleavage and at least 18 nucleotides of gRNA sequence were reported necessary for efficient DNA cleavage in vitro; see Zetsche et al. (2015) *Cell,* 163:759-771. In practice, guide RNA sequences are generally designed to have a length of between 17-24 nucleotides (frequently 19, 20, or 21 nucleotides) and exact complementarity (i. e., perfect base-pairing) to the targeted gene or nucleic acid sequence; guide RNAs having less than 100% complementarity to the target sequence can be used (e. g., a gRNA with a length of 20 nucleotides and between 1-4 mismatches to the target sequence) but can increase the potential for off-target effects. The design of effective guide RNAs for use in plant genome editing is disclosed in US Patent Application Publication 2015/0082478 A1, the entire specification of which is incorporated herein by reference. More recently, efficient gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing); see, for example, Cong et al. (2013) Science, 339:819-823; Xing et al. (2014) *BMC Plant Biol.,* 14:327-340. Chemically modified sgRNAs have been demonstrated to be effective in genome editing; see, for example, Hendel et al. (2015) *Nature Biotechnol.,* 985-991.

CRISPR-type genome editing has value in various aspects of agriculture research and development. CRISPR elements, i. e., CRISPR endonucleases and CRISPR single-guide RNAs, are useful in effecting genome editing without remnants of the CRISPR elements or selective genetic markers occurring in progeny. Alternatively, genome-inserted CRISPR elements are useful in plant lines adapted for multiplex genetic screening and breeding. For instance, a plant species can be created to express one or more of a CRISPR endonuclease such as a Cas9- or a Cpf1-type endonuclease or combinations with unique PAM recognition sites. Cpf1 endonuclease and corresponding guide RNAs and PAM sites are disclosed in US Patent Application Publication 2016/0208243 A1, which is incorporated herein by reference for its disclosure of DNA encoding Cpf1 endonucleases and guide RNAs and PAM sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for trait introgression. Multiple endonucleases can be provided in expression cassettes with the appropriate promoters to allow multiple genome editing in a spatially or temporally separated fashion in either in chromosome DNA or episome DNA.

Whereas wild-type Cas9 generates double-strand breaks (DSBs) at specific DNA sequences targeted by a gRNA, a number of CRISPR endonucleases having modified functionalities are available, for example: (1) a "nickase" version of Cas9 generates only a single-strand break; (2) a catalytically inactive Cas9 ("dCas9") does not cut the target DNA but interferes with transcription; dCas9 can further be fused with a repressor peptide; (3) a catalytically inactive Cas9 ("dCas9") fused to an activator peptide can activate or increase gene expression; (4) a catalytically inactive Cas9 (dCas9) fused to FokI nuclease ("dCas9-FokI") can be used to generate DSBs at target sequences homologous to two gRNAs. See, e. g., the numerous CRISPR/Cas9 plasmids disclosed in and publicly available from the Addgene repository (Addgene, 75 Sidney St., Suite 550A, Cambridge, MA 02139; addgene [dot]org/crispr/). A "double nickase" Cas9 that introduces two separate double-strand breaks, each directed by a separate guide RNA, is described as achieving more accurate genome editing by Ran et al. (2013) Cell, 154:1380-1389.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety.

In some embodiments, one or more vectors driving expression of one or more polynucleotides encoding elements of a genome-editing system (e. g., encoding a guide RNA or a nuclease) are introduced into a plant cell or a plant protoplast, whereby these elements, when expressed, result in alteration of a target nucleotide sequence. In embodiments, a vector comprises a regulatory element such as a promoter operably linked to one or more polynucleotides encoding elements of a genome-editing system. In such embodiments, expression of these polynucleotides can be controlled by selection of the appropriate promoter, particularly promoters functional in a plant cell; useful promoters include constitutive, conditional, inducible, and temporally or spatially specific promoters (e. g., a tissue specific promoter, a developmentally regulated promoter, or a cell cycle regulated promoter). In embodiments the promoter is operably linked to nucleotide sequences encoding multiple guide RNAs, wherein the sequences encoding guide RNAs are separated by a cleavage site such as a nucleotide sequence encoding a microRNA recognition/cleavage site or a self-cleaving ribozyme (see, e. g., Ferré-D'Amaré and Scott (2014) *Cold Spring Harbor Perspectives Biol.,* 2:a003574). In embodiments, the promoter is a pol II promoter operably linked to a nucleotide sequence encoding one or more guide RNAs. In embodiments, the promoter operably linked to one or more polynucleotides encoding elements of a genome-editing system is a constitutive promoter that drives DNA expression in plant cells including in the nucleus or in an organelle such as a chloroplast or mitochondrion. Examples of constitutive promoters include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and a opaline synthase (NOS) and octapine synthase (OCS) promoter from *Agrobacterium tumefaciens*. In embodiments, the promoter operably linked to one or more polynucleotides encoding elements of a genome-editing system is a promoter from figwort mosaic virus (FMV), a RUBISCO promoter, or a pyruvate phosphate dikinase (PDK) promoter, which is active in the chloroplasts of mesophyll cells. Other contemplated promoters include cell-specific or tissue-specific or developmentally regulated promoters, for example, a promoter that limits the expression of the nucleic acid targeting system to germline or reproductive cells (e. g., promoters of genes encoding DNA ligases, recombinases, replicases, or other genes specifically expressed in germline or reproductive cells); in such embodiments, the nuclease-mediated genetic modification (e. g., chromosomal or episomal double-stranded DNA cleavage) is limited only those cells from which DNA is inherited in subsequent generations, which is advantageous where it is desirable that expression of the genome-editing system be limited in order to avoid genotoxicity or other unwanted effects. All of the patent publications referenced in this paragraph are incorporated herein by reference in their entirety.

In some embodiments, elements of a genome-editing system (e. g., an RNA-guided nuclease and a guide RNA) are operably linked to separate regulatory elements on separate vectors. In other embodiments, two or more elements of a genome-editing system expressed from the same or different regulatory elements or promoters are combined in a single vector, optionally with one or more additional vectors providing any additional necessary elements of a genome-editing system not included in the first vector. For example, multiple guide RNAs can be expressed from one vector, with the appropriate RNA-guided nuclease expressed from a second vector. In another example, one or more vectors for the expression of one or more guide RNAs (e. g., crRNAs or sgRNAs) are delivered to a plant cell or a plant protoplast that expresses the appropriate RNA-guided nuclease, or to a plant cell or a plant protoplast that otherwise contains the nuclease, such as by way of prior administration thereto of a vector for in vivo expression of the nuclease.

Genome-editing system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In embodiments, the endonuclease and the nucleic acid-targeting guide RNA may be operably linked to and expressed from the same promoter. In embodiments, a single promoter drives expression of a transcript encoding an endonuclease and the guide RNA, embedded within one or more intron sequences (e. g., each in a different intron, two or more in at least one intron, or all in a single intron), which can be plant-derived; such use of introns is especially contemplated when the expression vector is being transformed or transfected into a monocot plant cell or a monocot plant protoplast.

Expression vectors provided herein may contain a DNA segment near the 3' end of an expression cassette that acts as a signal to terminate transcription and directs polyadenylation of the resultant mRNA. These are commonly referred to as "3'-untranslated regions" or "3'-UTRs" or "polyadenylation signals". Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in US Patent Application Publication 2002/0192813 A1, incorporated herein by reference.

In certain embodiments, a vector or an expression cassette includes additional components, e. g., a polynucleotide encoding a drug resistance or herbicide gene or a polynucleotide encoding a detectable marker such as green fluorescent protein (GFP) or beta-glucuronidase (gus) to allow convenient screening or selection of cells expressing the vector. In embodiments, the vector or expression cassette includes additional elements for improving delivery to the plant cell or plant protoplast or for directing or modifying expression of one or more genome-editing system elements, for example, fusing a sequence encoding a cell-penetrating peptide, localization signal, transit, or targeting peptide to the RNA-guided nuclease, or adding a nucleotide sequence to stabilize a guide RNA; such fusion proteins (and the polypeptides encoding such fusion proteins) or combination polypeptides, as well as expression cassettes and vectors for their expression in a cell, are specifically claimed. In embodiments, an RNA-guided nuclease (e. g., Cas9, Cpf1, CasY, CasX, C2c1, or C2c3) is fused to a localization signal, transit, or targeting peptide, e. g., a nuclear localization signal (NLS), a chloroplast transit peptide (CTP), or a mitochondrial targeting peptide (MTP); in a vector or an expression cassette, the nucleotide sequence encoding any of these can be located either 5' and/or 3' to the DNA encoding the nuclease. For example, a plant-codon-optimized Cas9 (pco-Cas9) from *Streptococcus pyogenes* and *S. thermophilus* containing nuclear localization signals and codon-optimized for expression in maize is disclosed in PCT/US2015/018104 (published as WO/2015/131101 and claiming priority to U.S. Provisional Patent Application 61/945,700), incorporated herein by reference. In another example, a chloroplast-targeting RNA is appended to the 5' end of an mRNA encoding an endonuclease to drive the accumulation of the mRNA in chloroplasts; see Gomez, et al. (2010) *Plant Signal Behav.,* 5: 1517-1519. In an embodiment, a Cas9 from *Streptococcus pyogenes* is fused to a nuclear localization signal (NLS), such as the NLS from SV40. In an embodiment, a Cas9 from *Streptococcus pyogenes* is fused to a cell-penetrating peptide (CPP), such as octa-arginine or nona-arginine or a homoarginine 12-mer oligopeptide, or a CPP disclosed in the database of cell-penetrating peptides CPPsite 2.0, publicly available at crdd [dot]osdd[dot]net/raghava/cppsite/. In an embodiment, a Cas9 from *Streptococcus pyogenes* is fused to a chloroplast transit peptide (CTP) sequence. In embodiments, a CTP sequence is obtained from any nuclear gene that encodes a protein that targets a chloroplast, and the isolated or synthesized CTP DNA is appended to the 5' end of the DNA that encodes a nuclease targeted for use in a chloroplast. Chloroplast transit peptides and their use are described in U.S. Pat. Nos. 5,188,642, 5,728,925, and 8,420,888, all of which are incorporated herein by reference in their entirety. Specifically, the CTP nucleotide sequences provided with the sequence identifier (SEQ ID) numbers 12-15 and 17-22 of U.S. Pat. No. 8,420,888 are incorporated herein by reference. In an embodiment, a Cas9 from *Streptococcus pyogenes* is fused to a mitochondrial targeting peptide (MTP), such as a plant MTP sequence; see, e. g., Jores et al. (2016) *Nature Communications,* 7:12036-12051.

Plasmids designed for use in plants and encoding CRISPR genome editing elements (CRISPR nucleases and guide RNAs) are publicly available from plasmid repositories such as Addgene (Cambridge, Massachusetts; also see "addgene [dot]com"). In embodiments, such plasmids are used to co-express both CRISPR nuclease mRNA and guide RNA(s); in other embodiments, CRISPR endonuclease mRNA and guide RNA are delivered from separate plasmids. In embodiments, the plasmids are *Agrobacterium* TI plasmids. Materials and methods for preparing expression cassettes and vectors for CRISPR endonuclease and guide RNA for stably integrated and/or transient plant transformation are disclosed in PCT/US2015/018104 (published as WO/2015/131101 and claiming priority to U.S. Provisional Patent Application 61/945,700), US Patent Application Publication 2015/0082478 A1, and PCT/US2015/038767 (published as WO/2016/007347 and claiming priority to U.S. Provisional Patent Application 62/023,246), all of which are incorporated herein by reference in their entirety. In embodiments, such expression cassettes are isolated linear fragments, or are part of a larger construct that includes bacterial replication elements and selectable markers; such embodiments are useful, e. g., for particle bombardment or nanoparticle delivery or protoplast transformation. In embodiments, the expression cassette is adjacent to or located between T-DNA borders or contained within a binary vector, e. g., for *Agrobacterium*-mediated transformation. In embodiments, a plasmid encoding a CRISPR nuclease is delivered to a plant cell or a plant protoplast for stable integration of the CRISPR nuclease into the genome of the plant cell or plant protoplast, or alternatively for transient expression of the CRISPR nuclease. In embodiments, plasmids encoding a CRISPR nuclease are delivered to a plant cell or a plant protoplast to achieve stable or transient expression of the CRISPR nuclease, and one or multiple guide RNAs (such as a library of individual guide RNAs or multiple pooled guide RNAs) or plasmids encoding the guide RNAs are delivered to the plant cell or plant protoplast individually or in combinations, thus providing libraries or arrays of plant cells or plant protoplasts (or of plant callus or whole plants derived therefrom), in which a variety of genome edits are provided by the different guide RNAs.

In certain embodiments where the genome-editing system is a CRISPR system, expression of the guide RNA is driven by a plant U6 spliceosomal RNA promoter, which can be native to the genome of the plant cell or plant protoplast or from a different species, e. g., a U6 promoter from maize, tomato, or soybean such as those disclosed in PCT/US2015/018104 (published as WO 2015/131101 and claiming priority to U.S. Provisional Patent Application 61/945,700), incorporated herein by reference, or a homologue thereof; such a promoter is operably linked to DNA encoding the guide RNA for directing an endonuclease, followed by a suitable 3' element such as a U6 poly-T terminator. In another embodiment, an expression cassette for expressing guide RNAs in plants is used, wherein the promoter is a plant U3, 7SL (signal recognition particle RNA), U2, or U5 promoter, or chimerics thereof, e. g., as described in PCT/US2015/018104 (published as WO 2015/131101 and claiming priority to U.S. Provisional Patent Application 61/945,700), incorporated herein by reference. When multiple or different guide RNA sequences are used, a single expression construct may be used to correspondingly direct the genome editing activity to the multiple or different target sequences in a plant cell or a plant protoplast. In various embodiments, a single vector includes 1, 2, 3, 4, 5, 6, 7, 8, 9, 10, about 15, about 20, or more guide RNA sequences; in other embodiments, 1, 2, 3, 4, 5, 6, 7, 8, 9, 10, about 15, about 20, or more guide RNA sequences are provided on multiple vectors, which can be delivered to one or multiple plant cells or plant protoplasts (e. g., delivered to an array of plant cells or plant protoplasts, or to a pooled population of plant cells or plant protoplasts).

In embodiments, one or more guide RNAs and the corresponding RNA-guided nuclease are delivered together or simultaneously. In other embodiments, one or more guide RNAs and the corresponding RNA-guided nuclease are delivered separately; these can be delivered in separate, discrete steps and using the same or different delivery techniques. In an example, an RNA-guided nuclease is delivered to a plant cell or plant protoplast by particle bombardment, on carbon nanotubes, or by *Agrobacterium*-mediated transformation, and one or more guide RNAs is delivered to the plant cell or plant protoplast in a separate step using the same or different delivery technique. In embodiments, an RNA-guided nuclease encoded by a DNA molecule or an mRNA is delivered to a plant cell or plant protoplast with enough time prior to delivery of the guide RNA to permit expression of the nuclease in the plant cell or plant protoplast; for example, an RNA-guided nuclease encoded by a DNA molecule or an mRNA is delivered to a plant cell or plant protoplast between 1-12 hours (e. g., about 1, 2, 3, 4, 5, 6, 7, 8, 9, 10, 11, or 12 hours, or between about 1-6 hours or between about 2-6 hours) prior to the delivery of the guide RNA to the plant cell or plant protoplast. In embodiments, whether the RNA-guided nuclease is delivered simultaneously with or separately from an initial dose of guide RNA, succeeding "booster" doses of guide RNA are delivered subsequent to the delivery of the initial dose; for example, a second "booster" dose of guide RNA is delivered to a plant cell or plant protoplast between 1-12 hours (e. g., about 1, 2, 3, 4, 5, 6, 7, 8, 9, 10, 11, or 12 hours, or between about 1-6 hours or between about 2-6 hours) subsequent to the delivery of the initial dose of guide RNA to the plant cell or plant protoplast. Similarly, in some embodiments, multiple deliveries of an RNA-guided nuclease or of a DNA molecule or an mRNA encoding an RNA-guided nuclease are used to increase efficiency of the genome modification.

In embodiments, the desired genome modification involves homologous recombination, wherein one or more double-stranded DNA break in the target nucleotide sequence is generated by the RNA-guided nuclease and guide RNA(s), followed by repair of the break(s) using a homologous recombination mechanism ("homology-directed repair"). In such embodiments, a donor template that encodes the desired nucleotide sequence to be inserted or knocked-in at the double-stranded break is provided to the plant cell or plant protoplast; examples of suitable templates include single-stranded DNA templates and double-stranded DNA templates (e. g., in the form of a plasmid). In general, a donor template encoding a nucleotide change over a region of less than about 50 nucleotides is conveniently provided in the form of single-stranded DNA; larger donor templates (e. g., more than 100 nucleotides) are often conveniently provided as double-stranded DNA plasmids. In embodiments, the various compositions and methods described herein for delivering guide RNAs and nucleases are also generally useful for delivering the donor template polynucleotide to the plant cell or plant protoplast; this delivery can be simultaneous with, or separate from (generally after) delivery of the nuclease and guide RNA to the plant cell or plant protoplast. For example, a donor template can be transiently introduced into a plant cell or plant protoplast, optionally with the nuclease and/or gRNA; in embodiments, the donor template is provided to the plant cell or plant protoplast in a quantity that is sufficient to achieve the desired homology-directed repair but that does not persist in the plant cell or plant protoplast after a given period of time (e. g., after one or more cell division cycles). In embodiments, a donor template has a core nucleotide sequence that differs from the target nucleotide sequence (e. g., a homologous endogenous genomic region) by at least 1, at least 5, at least 10, at least 20, at least 30, at least 40, at least 50, or more nucleotides. This core sequence is flanked by "homology arms" or regions of high sequence identity with the targeted nucleotide sequence; in embodiments, the regions of high identity include at least 10, at least 50, at least 100, at least 150, at least 200, at least 300, at least 400, at least 500, at least 600, at least 750, or at least 1000 nucleotides on each side of the core sequence. In embodiments where the donor template is in the form of a single-stranded DNA, the core sequence is flanked by homology arms including at least 10, at least 20, at least 30, at least 40, at least 50, at least 60, at least 70, at least 80, or at least 100 nucleotides on each side of the core sequence. In embodiments where the donor template is in the form of a double-stranded DNA plasmid, the core sequence is flanked by homology arms including at least 500, at least 600, at least 700, at least 800, at least 900, or at least 1000 nucleotides on each side of the core sequence. In an embodiment, two separate double-strand breaks are introduced into the plant cell or plant protoplast's target nucleotide sequence with a "double nickase" Cas9 (see Ran et al. (2013) Cell, 154:1380-1389), followed by delivery of the donor template.

Methods of Altering a Target Nucleotide Sequence in a Plant Cell or Plant Protoplast In one aspect the invention provides a method of delivering a guide RNA (gRNA) to a plant cell or plant protoplast wherein the gRNA has a nucleotide sequence designed to alter a target nucleotide sequence in the plant cell or plant protoplast, wherein the gRNA is provided as a polynucleotide composition comprising: (i) a CRISPR RNA (crRNA) that includes the gRNA, or a polynucleotide that encodes a crRNA, or a polynucleotide that is processed into a crRNA; or (ii) a single guide RNA (sgRNA) that includes the gRNA, or a polynucleotide that encodes a sgRNA, or a polynucleotide that is processed into a sgRNA; wherein the delivery of the polynucleotide composition includes at least one treatment selected from the group consisting of: direct application; soaking or imbibition; vacuum infiltration; application of negative or positive pressure; introduction into the vascular system; microinjection; application of ultrasound or vibration; application of hydrodynamic pressure, friction, cavitation or shear stress; vortexing; centrifugation; mechanical cell wall or cell membrane deformation or breakage; enzymatic cell wall or cell membrane breakage or permeabilization; abrasion; electroporation; and treatment with at least one chemical, enzymatic, or physical agent; whereby the gRNA is delivered to the plant cell or plant protoplast. In embodiments, delivery of the gRNA results in alteration of the target nucleotide sequence in the plant cell or plant protoplast.

The target nucleotide sequence is one or more nucleotide sequences, including protein-coding sequence or non-coding sequence or a combination thereof. Embodiments include a plant nuclear sequence, a plant plastid sequence, a plant mitochondrial sequence, a sequence of a symbiont, pest, or pathogen of a plant, and combinations thereof.

Embodiments include exons, introns, regulatory sequences including promoters, other 5' elements and 3' elements, and genomic loci encoding non-coding RNAs including long non-coding RNAs (lncRNAs), microRNAs (miRNAs), and trans-acting siRNAs (ta-siRNAs). In embodiments, multiple target nucleotide sequences are altered, for example, by delivery of multiple gRNAs to the plant cell or plant protoplast; the multiple target nucleotide sequences can be part of the same gene (e. g., different locations in a single coding region or in different exons of a protein-coding gene) or different genes.

In embodiments, the guide RNA (gRNA) has a sequence of between 16-24 nucleotides in length (e. g., 16, 17, 18, 19, 20, 21, 22, 23, or 24 nucleotides in length). Specific embodiments include gRNAs of 19, 20, or 21 nucleotides in length and having 100% complementarity to the target nucleotide sequence. In many embodiments the gRNA has exact complementarity (i. e., perfect base-pairing) to the target nucleotide sequence; in certain other embodiments the gRNA has less than 100% complementarity to the target nucleotide sequence. The design of effective gRNAs for use in plant genome editing is disclosed in US Patent Application Publication 2015/0082478 A1, the entire specification of which is incorporated herein by reference. In embodiments where multiple gRNAs are employed, the multiple gRNAs can be delivered separately (as separate RNA molecules or encoded by separate DNA molecules) or in combination, e. g., as an RNA molecule containing multiple gRNA sequences or as a DNA molecule encoding an RNA molecule containing multiple gRNA sequences; see, for example, US Patent Application Publication 2016/0264981 A1, the entire specification of which is incorporated herein by reference, which discloses RNA molecules including multiple RNA sequences (such as gRNA sequences) separated by tRNA cleavage sequences. Efficient Cas9-mediated gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing).

Thus, in certain embodiments wherein the nuclease is a Cas9-type nuclease, the gRNA can be provided as a polynucleotide composition including: (a) a CRISPR RNA (crRNA) that includes the gRNA together with a separate tracrRNA, or (b) at least one polynucleotide that encodes a crRNA and a tracrRNA (on a single polynucleotide or on separate polynucleotides), or (c) at least one polynucleotide that is processed into one or more crRNAs and a tracrRNA. In other embodiments wherein the nuclease is a Cas9-type nuclease, the gRNA can be provided as a polynucleotide composition including a CRISPR RNA (crRNA) that includes the gRNA, and the required tracrRNA is provided in a separate composition or in a separate step, or is otherwise provided to the plant cell or plant protoplast (for example, to a plant cell or plant protoplast that stably or transiently expresses the tracrRNA from a polynucleotide encoding the tracrRNA). In other embodiments wherein the nuclease is a Cas9-type nuclease, the gRNA can be provided as a polynucleotide composition comprising: (a) a single guide RNA (sgRNA) that includes the gRNA, or (b) a polynucleotide that encodes a sgRNA, or (c) a polynucleotide that is processed into a sgRNA. Cpf1-mediated gene editing does not require a tracrRNA; thus, in embodiments wherein the nuclease is a Cpf1-type nuclease, the gRNA is provided as a polynucleotide composition comprising (a) a CRISPR RNA (crRNA) that includes the gRNA, or (b) a polynucleotide that encodes a crRNA, or (c) a polynucleotide that is processed into a crRNA.

In embodiments of the method, the polynucleotide composition optionally includes an RNA-guided nuclease, or a polynucleotide that encodes the RNA-guided nuclease. In other embodiments of the method, the method further includes the step of providing to the plant cell or plant protoplast an RNA-guided nuclease or a polynucleotide that encodes the RNA-guided nuclease. In other embodiments of the method, the plant cell or plant protoplast includes an RNA-guided nuclease or a polynucleotide that encodes the RNA-guided nuclease; in an example the plant cell or plant protoplast stably or transiently expresses the RNA-guided nuclease. In embodiments, the RNA-guided nuclease is selected from the group consisting of an RNA-guided DNA endonuclease, a type II Cas nuclease, a Cas9, a type V Cas nuclease, a Cpf1, a CasY, a CasX, a C2c1, a C2c3, an engineered RNA-guided nuclease, and a codon-optimized RNA-guided nuclease. In embodiments, the polynucleotide that encodes the RNA-guided nuclease is, for example, DNA that encodes the RNA-guided nuclease and is stably integrated in the genome of the plant cell or plant protoplast, DNA or RNA that encodes the RNA-guided nuclease and is transiently present in or introduced into the plant cell or plant protoplast; such DNA or RNA can be introduced, e. g., by using a vector such as a plasmid or viral vector or as an mRNA, or as vector-less DNA or RNA introduced directly into the plant cell or plant protoplast.

In embodiments of the method that further include the step of providing to the plant cell or plant protoplast an RNA-guided nuclease or a polynucleotide that encodes the RNA-guided nuclease, the RNA-guided nuclease is provided simultaneously with the polynucleotide composition that includes the gRNA, or in a separate step that precedes or follows the step of providing the polynucleotide composition. In embodiments, the polynucleotide composition that includes the gRNA further includes an RNA-guided nuclease or a polynucleotide that encodes the RNA-guided nuclease. In other embodiments, there is provided a separate composition that includes an RNA-guided nuclease or a polynucleotide that encodes the RNA-guided nuclease. In embodiments, the RNA-guided nuclease is provided as a ribonucleoprotein (RNP) complex, e. g., a preassembled RNP that includes the RNA-guided nuclease complexed with a polynucleotide including the gRNA or encoding a gRNA, or a preassembled RNP that includes a polynucleotide that encodes the RNA-guided nuclease (and optionally encodes the gRNA, or is provided with a separate polynucleotide including the gRNA or encoding a gRNA), complexed with a protein. In embodiments, the RNA-guided nuclease is a fusion protein, i. e., wherein the RNA-guided nuclease (e. g., Cas9, Cpf1, CasY, CasX, C2c1, or C2c3) is covalently bound through a peptide bond to a cell-penetrating peptide, a nuclear localization signal peptide, a chloroplast transit peptide, or a mitochondrial targeting peptide; such fusion proteins are conveniently encoded in a single nucleotide sequence, optionally including codons for linking amino acids. In embodiments, the RNA-guided nuclease or a polynucleotide that encodes the RNA-guided nuclease is provided as a complex with a cell-penetrating peptide or other transfecting agent. In embodiments, the RNA-guided nuclease or a polynucleotide that encodes the RNA-guided nuclease is complexed with, or covalently or non-covalently bound to, a further element, e. g., a carrier molecule, an antibody, an antigen, a viral movement protein, a polymer, a detectable label (e. g., a moiety detectable by fluorescence, radioactivity, or enzymatic or immunochemical reaction), a quantum dot, or a particulate or nanoparticulate. In embodiments, the RNA-guided nuclease or a polynucleotide that encodes the RNA-guided nuclease is provided in a solution, or is provided in a liposome, micelle, emulsion, reverse emulsion, suspension, or other mixed-phase composition.

The RNA-guided nuclease is provided to the plant cell or plant protoplast by any suitable technique. In embodiments, the RNA-guided nuclease is provided by directly contacting the plant cell or plant protoplast with the RNA-guided nuclease or the polynucleotide that encodes the RNA-guided nuclease. In embodiments, the RNA-guided nuclease is provided by transporting the RNA-guided nuclease or a polynucleotide that encodes the RNA-guided nuclease into the plant cell or plant protoplast using a chemical, enzymatic, or physical agent as provided in detail below in the paragraphs following the heading "Delivery Agents". In embodiments, the RNA-guided nuclease is provided by bacterially mediated (e. g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the plant cell or plant protoplast with a polynucleotide encoding the RNA-guided nuclease; see, e. g., Broothaerts et al. (2005) *Nature,* 433:629-633. In an embodiment, the RNA-guided nuclease is provided by transcription in the plant cell or plant protoplast of a DNA that encodes the RNA-guided nuclease and is stably integrated in the genome of the plant cell or plant protoplast or that is provided to the plant cell or plant protoplast in the form of a plasmid or expression vector (e. g., a viral vector) that encodes the RNA-guided nuclease (and optionally encodes one or more gRNAs, crRNAs, or sgRNAs, or is optionally provided with a separate plasmid or vector that encodes one or more gRNAs, crRNAs, or sgRNAs). In embodiments, the RNA-guided nuclease is provided to the plant cell or plant protoplast as a polynucleotide that encodes the RNA-guided nuclease, e. g., in the form of an mRNA encoding the nuclease.

Where a polynucleotide is concerned (e. g., a crRNA that includes the gRNA together with a separate tracrRNA, or at least one polynucleotide that encodes a crRNA and a tracrRNA (on a single polynucleotide or on separate polynucleotides), or at least one polynucleotide that is processed into one or more crRNAs and a tracrRNA, or a sgRNA that includes the gRNA, or a polynucleotide that encodes a sgRNA, or a polynucleotide that is processed into a sgRNA, or a polynucleotide that encodes the RNA-guided nuclease), embodiments of the polynucleotide include: (a) double-stranded RNA; (b) single-stranded RNA; (c) chemically modified RNA; (d) double-stranded DNA; (e) single-stranded DNA; (f) chemically modified DNA; or (g) a combination of (a)-(f). Where expression of a polynucleotide is involved (e. g., expression of a crRNA from a DNA encoding the crRNA, or expression and translation of a RNA-guided nuclease from a DNA encoding the nuclease), in some embodiments it is sufficient that expression be transient, i. e., not necessarily permanent or stable in the plant cell. Certain embodiments of the polynucleotide further include additional nucleotide sequences that provide useful functionality; non-limiting examples of such additional nucleotide sequences include an aptamer or riboswitch sequence, nucleotide sequence that provides secondary structure such as stem-loops or that provides a sequence-specific site for an enzyme (e. g., a sequence-specific recombinase or endonuclease site), T-DNA (e. g., DNA sequence encoding a gRNA, crRNA, tracrRNA, or sgRNA is enclosed between left and right T-DNA borders from *Agrobacterium* spp. or from other bacteria that infect or induce tumours in plants), a DNA nuclear-targeting sequence, a regulatory sequence such as a promoter sequence, and a transcript-stabilizing sequence. Certain embodiments of the polynucleotide include those wherein the polynucleotide is complexed with, or covalently or non-covalently bound to, a non-nucleic acid element, e. g., a carrier molecule, an antibody, an antigen, a viral movement protein, a cell-penetrating or pore-forming peptide, a polymer, a detectable label, a quantum dot, or a particulate or nanoparticulate.

Generally, the plant cell or plant protoplast is an isolated plant cell or plant protoplast (e. g., a plant cell or plant protoplast isolated from a whole plant or plant part or plant tissue, or an isolated plant cell or plant protoplast in suspension or plate culture). Similar but not identical methods and compositions for delivery of gRNAs or nucleases or polynucleotides encoding such are useful for editing the genome of non-isolated plant cells in situ or in planta, such as a plant cell located in an intact or growing plant or in a plant part or tissue. In embodiments, the plant cell or plant protoplast is capable of division and further differentiation. In embodiments, the plant cell or plant protoplast is obtained or isolated from a plant or part of a plant selected from the group consisting of a plant tissue, a whole plant, an intact nodal bud, a shoot apex or shoot apical meristem, a root apex or root apical meristem, lateral meristem, intercalary meristem, a seedling (e. g., a germinating seed or small seedling or a larger seedling with one or more true leaves), a whole seed (e. g., an intact seed, or a seed with part or all of its seed coat removed or treated to make permeable), a halved seed or other seed fragment, an embryo (e. g., a mature dissected zygotic embryo, a developing embryo, a dry or rehydrated or freshly excised embryo), and callus.

In embodiments, the plant cell or plant protoplast is diploid or polyploid. In embodiments, the plant cell or plant protoplast is haploid or can be induced to become haploid; techniques for making and using haploid plants and plant cells are known in the art, see, e. g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", a protocol publicly available at www[dot]openwetware[dot]org/images/d/d3/Haploid_Arabidopsis_protocol[dot]pdf; Ravi et al. (2014) *Nature Communications,* 5:5334, doi: 10.1038/ncomms6334); Examples of haploid cells include but are not limited to plant cells obtained from haploid plants and plant cells obtained from reproductive tissues, e. g., from flowers, developing flowers or flower buds, ovaries, ovules, megaspores, anthers, pollen, and microspores. In embodiments where the plant cell or plant protoplast is haploid, the method can further include the step of chromosome doubling (e. g., by spontaneous chromosomal doubling by meiotic non-reduction, or by using a chromosome doubling agent such as colchicine, oryzalin, or trifluralin) in the plant cell or plant protoplast including the altered target nucleotide sequence to produce a doubled haploid plant cell or plant protoplast that is homozygous for the altered target nucleotide sequence; yet other embodiments include regeneration of a doubled haploid plant from the doubled haploid plant cell or plant protoplast, wherein the regenerated doubled haploid plant is homozygous for the altered target nucleotide sequence. Thus, aspects of the invention are related to the haploid plant cell or plant protoplast having the altered target nucleotide sequence as well as a doubled haploid plant cell or plant protoplast or a doubled haploid plant that is homozygous for the altered target nucleotide sequence. Another aspect of the invention is related to a hybrid plant having at least one parent plant that is a doubled haploid plant provided by the method. Production of doubled haploid plants by these methods provides homozygosity in one generation, instead of requiring several generations of self-crossing to obtain homozygous plants; this may be particularly advantageous in slow-growing plants, such as fruit and other trees, or for producing hybrid plants that are offspring of at least one doubled-haploid plant.

In embodiments, the plant cell or plant protoplast is obtained from a dicot or a monocot plant of interest. Plants of interest include row crop plants, fruit-producing plants and trees, vegetables, trees, and ornamental plants including ornamental flowers, shrubs, trees, groundcovers, and turf grasses. Examples of commercially important cultivated crops, trees, and plants include: alfalfa (*Medicago sativa*), almonds (*Prunus dulcis*), apples (Malus x *domestica*), apricots (*Prunus armeniaca, P. brigantine, P. mandshurica, P. mume, P. sibirica*), asparagus (*Asparagus officinalis*), bananas (Musa spp.), barley (*Hordeum vulgare*), beans (*Phaseolus* spp.), blueberries and cranberries (*Vaccinium* spp.), cacao (*Theobroma cacao*), canola and rapeseed or oilseed rape, (*Brassica napus*), carnation (*Dianthus* caryophyllus), carrots (*Daucus carota sativus*), cassava (*Manihot esculentum*), cherry (*Prunus avium*), chickpea (Cider *arietinum*), chicory (*Cichorium intybus*), chili peppers and other *capsicum* peppers (*Capsicum annuum, C. frutescens, C. chinense, C. pubescens, C. baccatum*), chrysanthemums (*Chrysanthemum* spp.), coconut (*Cocos nucifera*), coffee (*Coffea* spp. including *Coffea arabica* and *Coffea canephora*), cotton (*Gossypium hirsutum* L.), cowpea (*Vigna unguiculata*), cucumber (*Cucumis sativus*), currants and gooseberries (*Ribes* spp.), eggplant or aubergine (*Solanum melongena*), *eucalyptus* (*Eucalyptus* spp.), flax (*Linum usitatissumum* L.), geraniums (*Pelargonium* spp.), grapefruit (*Citrus x paradisi*), grapes (Vitus spp.) including wine grapes (Vitus *vinifera*), guava (*Psidium guajava*), irises (Iris spp.), lemon (*Citrus limon*), lettuce (*Lactuca sativa*), limes (Citrus spp.), maize (*Zea mays* L.), mango (*Mangifera indica*), mangosteen (*Garcinia mangostana*), melon (*Cucumis melo*), millets (*Setaria* spp., *Echinochloa* spp., *Eleusine* spp, *Panicum* spp., *Pennisetum* spp.), oats (*Avena sativa*), oil palm (*Ellis quineensis*), olive (*Olea europaea*), onion (*Allium cepa*), orange (*Citrus sinensis*), *papaya* (*Carica papaya*), peaches and nectarines (*Prunus persica*), pear (*Pyrus* spp.), pea (Pisa *sativum*), peanut (*Arachis hypogaea*), peonies (*Paeonia* spp.), petunias (*Petunia* spp.), pineapple (*Ananas comosus*), plantains (*Musa* spp.), plum (*Prunus domestica*), poinsettia (*Euphorbia pulcherrima*), Polish canola (*Brassica rapa*), poplar (*Populus* spp.), potato (*Solanum tuberosum*), pumpkin (*Cucurbita pepo*), rice (*Oryza sativa* L.), roses (*Rosa* spp.), rubber (Hevea *brasiliensis*), rye (*Secale cereale*), safflower (*Carthamus tinctorius* L), sesame seed (*Sesame indium*), sorghum (*Sorghum bicolor*), soybean (*Glycine max* L.), squash (*Cucurbita pepo*), strawberries (*Fragaria* spp., *Fragaria x ananassa*), sugar beet (*Beta vulgaris*), sugarcanes (*Saccharum* spp.), sunflower (*Helianthus annus*), sweet potato (*Ipomoea batatas*), tangerine (*Citrus tangerina*), tea (*Camellia sinensis*), tobacco (*Nicotiana tabacum* L.), tomato (*Lycopersicon esculentum*), tulips (Tulipa spp.), turnip (*Brassica rapa rapa*), walnuts (*Juglans* spp. L.), watermelon (*Citrulus lanatus*), wheat (*Triticum aestivum*), and yams (*Discorea* spp.).

In embodiments, the plant cell or plant protoplast is obtained from a crop plant characterized as being of or derived from "elite" germplasm or genetic background, for example, from an inbred crop plant that is an elite strain of germplasm, or from a hybrid crop plant that is the progeny of at least one elite strain of germplasm (e. g., progeny of an inbred male parent of a first elite strain and an inbred female parent of a second elite strain). As used herein, an "elite" strain or line of a crop plant is one that has resulted from usually multiple rounds of breeding and selection for superior performance, e. g., superior yield or other agronomic trait. By "line" or "strain" is meant plants that share identical parentage and are generally inbred to some degree, and which are generally homozygous at most genetic loci; plants of a given line or strain exhibit a consistent and predictable phenotype and agronomic performance. A plant is "homozygous" when it has only one type of allele at a given locus, e. g., a diploid plant with two identical copies of an allele at a given locus. The term "inbred" refers to plants that are typically developed through multiple generations of inbreeding or "selfing", or alternatively are produced by doubling haploid plants, are genetically homozygous or substantially homozygous (e. g., homozygous at at least about 95% of its genetic loci), and which thus breed "true", that is to say, reproduce their phenotypic traits and agronomic performance characteristics in subsequent inbred generations. The term "hybrid" refers to a plant that is the offspring resulting from the crossing of two different inbred lines (i. e., crossing an inbred male parent with an inbred female parent); the first generation of such a cross is the "F1" generation, and subsequent generations are referred to as the "F2", "F3", "F4", etc. generations. F1 hybrid seeds germinate and grow into F1 hybrid plants, which because of heterosis often display superior agronomic performance when compared to either parent inbred. F1 hybrids are typically heterozygous over many or most loci in the genome.

Embodiments of the method involve various treatments employed to deliver the polynucleotide composition to the plant cell or plant protoplast. In embodiments, one or more treatments is employed to deliver the polynucleotide composition into the plant cell or plant protoplast, e. g., through barriers such as a cell wall or a plasma membrane or nuclear envelope or other lipid bilayer. In an embodiment, the polynucleotide composition is delivered directly, for example by direct contact of the polynucleotide composition with the plant cell or plant protoplast. Polynucleotide compositions in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a plant cell or plant protoplast (e. g., through abrasion or puncture or otherwise disruption of the cell wall or cell membrane, by spraying or dipping or soaking or otherwise directly contacting, by microinjection). For example, a plant cell or plant protoplast is soaked in a liquid polynucleotide composition, whereby the gRNA is delivered to the plant cell or plant protoplast. In embodiments, the polynucleotide composition is delivered using negative or positive pressure, for example, using vacuum infiltration or application of hydrodynamic or fluid pressure. In embodiments, the polynucleotide composition is introduced into the plant cell or plant protoplast, e. g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e. g., delivery of materials to cells employing microfluidic flow through a cell-deforming constriction as described in US Published Patent Application 2014/0287509, incorporated by reference in its entirety herein. Other techniques useful for delivering the polynucleotide composition to a plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e. g., abrasion with carborundum or other particulate abrasive or scarification with a file or sandpaper) or chemical scarification (e. g., treatment with an acid or caustic agent); and electroporation. In embodiments, the polynucleotide composition is provided by bacterially mediated (e. g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the plant cell or plant protoplast with a polynucleotide encoding the gRNA; see, e. g., Broothaerts et al. (2005) Nature, 433:629-633. Any of these techniques or a combination thereof are alternatively employed on the plant part or tissue or intact plant (or seed) from which the plant cell or plant protoplast is subsequently obtained or isolated; in embodiments, the polynucleotide composition is delivered in a separate step after the plant cell or plant protoplast has been obtained or isolated.

In embodiments, a treatment employed in delivery of the polynucleotide composition to the plant cell or plant protoplast is carried out under a specific thermal regime, which can involve one or more appropriate temperatures, e. g., chilling or cold stress (exposure to temperatures below that at which normal plant growth occurs), or heating or heat stress (exposure to temperatures above that at which normal plant growth occurs), or treating at a combination of different temperatures. In embodiments, a specific thermal regime is carried out on the plant cell or plant protoplast, or on the plant or plant part from which the plant cell or plant protoplast is subsequently obtained or isolated, in one or more steps separate from the polynucleotide composition delivery.

Delivery Agents: Embodiments of the method include treatment of the plant cell or plant protoplast, or the plant or plant part from which the plant cell or plant protoplast is obtained or isolated, with one or more delivery agents which can include at least one chemical, enzymatic, or physical agent, or a combination thereof. In embodiments, the polynucleotide composition further includes one or more one chemical, enzymatic, or physical agent for delivery. In embodiments of the method that further include the step of providing to the plant cell or plant protoplast an RNA-guided nuclease or a polynucleotide that encodes the RNA-guided nuclease, a composition including the RNA-guided nuclease or polynucleotide that encodes the RNA-guided nuclease further includes one or more one chemical, enzymatic, or physical agent for delivery. Treatment with the chemical, enzymatic or physical agent can be carried out simultaneously with the polynucleotide composition delivery, with the RNA-guided nuclease delivery, or in one or more separate steps that precede or follow the polynucleotide composition delivery or the RNA-guided nuclease delivery. In embodiments, a chemical, enzymatic, or physical agent, or a combination of these, is associated or complexed with the polynucleotide composition, with the gRNA or polynucleotide that encodes or is processed to the gRNA, or with the RNA-guided nuclease or polynucleotide that encodes the RNA-guided nuclease; examples of such associations or complexes include those involving non-covalent interactions (e. g., ionic or electrostatic interactions, hydrophobic or hydrophilic interactions, formation of liposomes, micelles, or other heterogeneous composition) and covalent interactions (e. g., peptide bonds, bonds formed using cross-linking agents). In non-limiting examples, a gRNA or polynucleotide that encodes or is processed to the gRNA is provided as a liposomal complex with a cationic lipid; a gRNA or polynucleotide that encodes or is processed to the gRNA is provided as a complex with a carbon nanotube; and an RNA-guided nuclease is provided as a fusion protein between the nuclease and a cell-penetrating peptide. Examples of agents useful for delivering a gRNA or polynucleotide that encodes or is processed to the gRNA or a nuclease or polynucleotide that encodes the nuclease include the various cationic liposomes and polymer nanoparticles reviewed by Zhang et al. (2007) *J. Controlled Release,* 123:1-10, and the cross-linked multilamellar liposomes described in US Patent Application Publication 2014/0356414 A1, incorporated by reference in its entirety herein.

In embodiments, the chemical agent is at least one selected from the group consisting of:

(a) solvents (e. g., water, dimethylsulfoxide, dimethylformamide, acetonitrile, N-pyrrolidine, pyridine, hexamethylphosphoramide, alcohols, alkanes, alkenes, dioxanes, polyethylene glycol, and other solvents miscible or emulsifiable with water or that will dissolve phosphonucleotides in non-aqueous systems);

(b) fluorocarbons (e. g., perfluorodecalin, perfluoromethyldecalin);

(c) glycols or polyols (e. g., propylene glycol, polyethylene glycol);

(d) surfactants, including cationic surfactants, anionic surfactants, non-ionic surfactants, and amphiphilic surfactants, e. g., alkyl or aryl sulfates, phosphates, sulfonates, or carboxylates; primary, secondary, or tertiary amines; quaternary ammonium salts; sultaines, betaines; cationic lipids; phospholipids; tallowamine; bile acids such as cholic acid; long chain alcohols; organosilicone surfactants including nonionic organosilicone surfactants such as trisiloxane ethoxylate surfactants or a silicone polyether copolymer such as a copolymer of polyalkylene oxide modified heptamethyl trisiloxane and allyloxypolypropylene glycol methylether (commercially available as SILWET L-77™ brand surfactant having CAS Number 27306-78-1 and EPA Number CAL. REG. NO. 5905-50073-AA, Momentive Performance Materials, Inc., Albany, N.Y.); specific examples of useful surfactants include sodium lauryl sulfate, the Tween series of surfactants, Triton-X100, Triton-X114, CHAPS and CHAPSO, Tergitol-type NP-40, Nonidet P-40;

(e) lipids, lipoproteins, lipopolysaccharides;

(f) acids, bases, caustic agents;

(g) peptides, proteins, or enzymes (e. g., cellulase, pectolyase, maceroenzyme, pectinase), including cell-penetrating or pore-forming peptides (e. g., (B0100)2K8, Genscript; poly-lysine, poly-arginine, or poly-homoarginine peptides; gamma zein, see US Patent Application publication 2011/0247100, incorporated herein by reference in its entirety; transcription activator of human immunodeficiency virus type 1 ("HIV-1 Tat") and other Tat proteins, see, e. g., www[dot]lifetein[dot]com/Cell_Penetrating_Peptides[dot]html and Järver (2012) *Mol. Therapy-Nucleic Acids,* 1:e27, 1-17); octa-arginine or nona-arginine; poly-homoarginine (see Unnamalai et al. (2004) FEBS Letters, 566: 307-310); see also the database of cell-penetrating peptides CPPsite 2.0 publicly available at crdd[dot] osdd[dot]net/raghava/cppsite/

(h) RNase inhibitors;

(i) cationic branched or linear polymers such as chitosan, poly-lysine, DEAE-dextran, polyvinylpyrrolidone ("PVP"), or polyethylenimine ("PEI", e. g., PEI, branched, MW 25,000, CAS #9002-98-6; PEI, linear, MW 5000, CAS #9002-98-6; PEI linear, MW 2500, CAS #9002-98-6);

(j) dendrimers (see, e. g., US Patent Application Publication 2011/0093982, incorporated herein by reference in its entirety);

(k) counter-ions, amines or polyamines (e. g., spermine, spermidine, putrescine), osmolytes, buffers, and salts (e. g., calcium phosphate, ammonium phosphate);

(l) polynucleotides (e. g., non-specific double-stranded DNA, salmon sperm DNA);

(m) transfection agents (e. g., Lipofectin®, Lipofectamine®, and Oligofectamine®, and Invivofectamine® (all from Thermo Fisher Scientific, Waltham, MA), PepFect (see Ezzat et al. (2011) *Nucleic Acids Res.,* 39:5284-5298), TransIt® transfection reagents (Mirus Bio, LLC, Madison, WI), and poly-lysine, poly-homoarginine, and poly-arginine molecules including octo-arginine and nono-arginine as described in Lu et al. (2010) *J. Agric. Food Chem.,* 58:2288-2294);

(n) antibiotics, including non-specific DNA double-strand-break-inducing agents (e. g., phleomycin, bleomycin, talisomycin);

(o) chelating agents such as ammonium oxalate, EDTA, EGTA, or cyclohexane diamine tetraacetate; and (p) antioxidants (e. g., glutathione, dithiothreitol, ascorbate).

In embodiments, the chemical agent is provided simultaneously with the gRNA (or polynucleotide encoding the gRNA or that is processed to the gRNA), for example, the polynucleotide composition including the gRNA further includes one or more chemical agent. In embodiments, the gRNA or polynucleotide encoding the gRNA or that is processed to the gRNA is covalently or non-covalently linked or complexed with one or more chemical agent; for example, the gRNA or polynucleotide encoding the gRNA or that is processed to the gRNA can be covalently linked to a peptide or protein (e. g., a cell-penetrating peptide or a pore-forming peptide) or non-covalently complexed with cationic lipids, polycations (e. g., polyamines), or cationic polymers (e. g., PEI). In embodiments, the gRNA or polynucleotide encoding the gRNA or that is processed to the gRNA is complexed with one or more chemical agents to form, e. g., a solution, liposome, micelle, emulsion, reverse emulsion, suspension, colloid, or gel.

In embodiments, the physical agent is at least one selected from the group consisting of particles or nanoparticles (e. g., particles or nanoparticles made of materials such as carbon, silicon, silicon carbide, gold, tungsten, polymers, or ceramics) in various size ranges and shapes, magnetic particles or nanoparticles (e. g., silenceMag Magnetotransfection™ agent, OZ Biosciences, San Diego, CA), abrasive or scarifying agents, needles or microneedles, matrices, and grids. In embodiments, particulates and nanoparticulates are useful in delivery of the polynucleotide composition or the nuclease or both. Useful particulates and nanoparticles include those made of metals (e. g., gold, silver, tungsten, iron, cerium), ceramics (e. g., aluminum oxide, silicon carbide, silicon nitride, tungsten carbide), polymers (e. g., polystyrene, polydiacetylene, and poly(3,4-ethylenedioxythiophene) hydrate), semiconductors (e. g., quantum dots), silicon (e. g., silicon carbide), carbon (e. g., graphite, graphene, graphene oxide, or carbon nanosheets, nanocomplexes, or nanotubes), and composites (e. g., polyvinylcarbazole/graphene, polystyrene/graphene, platinum/graphene, palladium/graphene nanocomposites). In embodiments, such particulates and nanoparticulates are further covalently or non-covalently functionalized, or further include modifiers or cross-linked materials such as polymers (e. g., linear or branched polyethylenimine, poly-lysine), polynucleotides (e. g., DNA or RNA), polysaccharides, lipids, polyglycols (e. g., polyethylene glycol, thiolated polyethylene glycol), polypeptides or proteins, and detectable labels (e. g., a fluorophore, an antigen, an antibody, or a quantum dot). In various embodiments, such particulates and nanoparticles are neutral, or carry a positive charge, or carry a negative charge. Embodiments of compositions including particulates include those formulated, e. g., as liquids, colloids, dispersions, suspensions, aerosols, gels, and solids. Embodiments include nanoparticles affixed to a surface or support, e. g., an array of carbon nanotubes vertically aligned on a silicon or copper wafer substrate. Embodiments include polynucleotide compositions including particulates (e. g., gold or tungsten or magnetic particles) delivered by a Biolistic-type technique or with magnetic force. The size of the particles used in Biolistics is generally in the "microparticle" range, for example, gold microcarriers in the 0.6, 1.0, and 1.6 micrometer size ranges (see, e. g., instruction manual for the Helios@ Gene Gun System, Bio-Rad, Hercules, CA; Randolph-Anderson et al. (2015) "Sub-micron gold particles are superior to larger particles for efficient Biolistic® transformation of organelles and some cell types", Bio-Rad US/EG Bulletin 2015), but successful Biolistics delivery using larger (40 nanometer) nanoparticles has been reported in cultured animal cells; see O'Brian and Lummis (2011) *BMC Biotechnol.,* 11:66-71. Other embodiments of useful particulates are nanoparticles, which are generally in the nanometer (nm) size range or less than 1 micrometer, e. g., with a diameter of less than about 1 nm, less than about 3 nm, less than about 5 nm, less than about 10 nm, less than about 20 nm, less than about 40 nm, less than about 60 nm, less than about 80 nm, and less than about 100 nm. Specific, non-limiting embodiments of nanoparticles commercially available (all from Sigma-Aldrich Corp., St. Louis, MO) include gold nanoparticles with diameters of 5, 10, or 15 nm; silver nanoparticles with particle sizes of 10, 20, 40, 60, or 100 nm; palladium "nanopowder" of less than 25 nm particle size; single-, double-, and multi-walled carbon nanotubes, e. g., with diameters of 0.7-1.1, 1.3-2.3, 0.7-0.9, or 0.7-1.3 nm, or with nanotube bundle dimensions of 2-10 nm by 1-5 micrometers, 6-9 nm by 5 micrometers, 7-15 nm by 0.5-10 micrometers, 7-12 nm by 0.5-10 micrometers, 110-170 nm by 5-9 micrometers, 6-13 nm by 2.5-20 micrometers. Embodiments include polynucleotide compositions including materials such as gold, silicon, cerium, or carbon, e. g., gold or gold-coated nanoparticles, silicon carbide whiskers, carborundum, porous silica nanoparticles, gelatin/silica nanoparticles, nanoceria or cerium oxide nanoparticles (CNPs), carbon nanotubes (CNTs) such as single-, double-, or multi-walled carbon nanotubes and their chemically functionalized versions (e. g., carbon nanotubes functionalized with amide, amino, carboxylic acid, sulfonic acid, or polyethylene glycol moeities), and graphene or graphene oxide or graphene complexes; see, for example, Wong et al. (2016) *Nano Lett.,* 16:1161-1172; Giraldo et al. (2014) *Nature Materials,* 13:400-409; Shen et al. (2012) *Theranostics,* 2:283-294; Kim et al. (2011) *Bioconjugate Chem.,* 22:2558-

2567; Wang et al. (2010) *J. Am. Chem. Soc. Comm.,* 132: 9274-9276; Zhao et al. (2016) *Nanoscale Res. Lett.,* 11:195-203; and Choi et al. (2016) *J. Controlled Release,* 235:222-235. See also, for example, the various types of particles and nanoparticles, their preparation, and methods for their use, e. g., in delivering polynucleotides and polypeptides to cells, disclosed in US Patent Application Publications 2010/0311168, 2012/0023619, 2012/0244569, 2013/0145488, 2013/0185823, 2014/0096284, 2015/0040268, 2015/0047074, and 2015/0208663, all of which are incorporated herein by reference in their entirety.

In embodiments wherein the polynucleotide composition includes an RNA-guided nuclease, or a polynucleotide that encodes the RNA-guided nuclease, or wherein the method further includes the step of providing to the plant cell or plant protoplast an RNA-guided nuclease or a polynucleotide that encodes the RNA-guided nuclease, one or more one chemical, enzymatic, or physical agent can similarly be employed. In embodiments, the RNA-guided nuclease (or polynucleotide encoding the RNA-guided nuclease) is provided separately, e. g., in a separate composition including the RNA-guided nuclease or polynucleotide encoding the RNA-guided nuclease. Such compositions can include other chemical or physical agents (e. g., solvents, surfactants, proteins or enzymes, transfection agents, particulates or nanoparticulates), such as those described above as useful in the polynucleotide composition used to provide the gRNA. For example, porous silica nanoparticles are useful for delivering a DNA recombinase into maize cells; see, e. g., Martin-Ortigosa et al. (2015) *Plant Physiol.,* 164:537-547. In an embodiment, the polynucleotide composition includes a gRNA and Cas9 nuclease, and further includes a surfactant and a cell-penetrating peptide. In an embodiment, the polynucleotide composition includes a plasmid that encodes both an RNA-guided nuclease and at least on gRNA, and further includes a surfactant and carbon nanotubes. In an embodiment, the polynucleotide composition includes multiple gRNAs and an mRNA encoding the RNA-guided nuclease, and further includes gold particles, and the polynucleotide composition is delivered to the plant cell or plant protoplast by Biolistics.

In related embodiments, one or more one chemical, enzymatic, or physical agent can be used in one or more steps separate from (preceding or following) that in which the polynucleotide composition is provided to the plant cell or plant protoplast. In an embodiment, the plant or plant part from which the plant cell or plant protoplast is obtained or isolated is treated with one or more one chemical, enzymatic, or physical agent in the process of obtaining or isolating the plant cell or plant protoplast. In embodiments, the plant or plant part is treated with an abrasive, a caustic agent, a surfactant such as Silwet L-77 or a cationic lipid, or an enzyme such as cellulase.

In embodiments, the plant cell or plant protoplast is prepared from plant cells obtained from a plant, plant part, or plant tissue that has been treated with the polynucleotide compositions (and optionally the nuclease). In embodiments, one or more one chemical, enzymatic, or physical agent, separately or in combination with the polynucleotide composition, is provided/applied at a location in the plant or plant part other than the plant location, part, or tissue from which the plant cell or plant protoplast is obtained or isolated. In embodiments, the polynucleotide composition is applied to adjacent or distal cells or tissues and is transported (e. g., through the vascular system or by cell-to-cell movement) to the meristem from which plant cells or plant protoplasts are subsequently isolated. In embodiments, the polynucleotide composition is applied by soaking a seed or seed fragment or embryo in the polynucleotide composition, whereby the gRNA is delivered to the seed or seed fragment or embryo from which plant cells or plant protoplasts are subsequently isolated. In embodiments, a flower bud or shoot tip is contacted with the polynucleotide composition, whereby the gRNA is delivered to cells in the flower bud or shoot tip from which plant cells or plant protoplasts are subsequently isolated. In embodiments, the polynucleotide composition is applied to the surface of a plant or of a part of a plant (e. g., a leaf surface), whereby the gRNA is delivered to tissues of the plant from which plant cells or plant protoplasts are subsequently isolated. In embodiments a whole plant or plant tissue is subjected to particle- or nanoparticle-mediated delivery (e. g., Biolistics or carbon nanotube or nanoparticle delivery) of the polynucleotide composition, whereby the gRNA is delivered to cells or tissues from which plant cells or plant protoplasts are subsequently isolated.

Delivery of a gRNA by the method of the invention results in alteration of the target nucleotide sequence in the plant cell or plant protoplast. In embodiments, the altered target nucleotide sequence includes at least one sequence modification selected from the group consisting of insertion of a nucleotide, deletion of a nucleotide, and replacement of a nucleotide. In embodiments, insertion of a nucleotide includes insertion of one or more nucleotides resulting in a heterologous sequence (that is to say, insertion of one or more nucleotides resulting in a sequence that does not normally occur at the locus of insertion). In embodiments, alteration of the target nucleotide sequence results in a change in expression (e. g., increase or decrease of expression or change in temporal or spatial specificity) of the target nucleotide sequence, methylation or demethylation of the target nucleotide sequence (e. g., resulting in an epigenetic change), a phenotype that is detectable in the plant cell or plant protoplast, or a combination of these. In embodiments, alteration of the target nucleotide sequence results in a phenotype or trait of interest observable in a seedling or plant grown or regenerated from the plant cell or plant protoplast; in some embodiments the phenotype or trait is heritable to succeeding generations of plants. Thus, related embodiments include such succeeding generations of plants or their seeds having inherited the altered target nucleotide sequence.

A related aspect of the invention is directed to the plant cell or plant protoplast including an altered target nucleotide sequence, provided by the method. Embodiments of the method further include one or more steps of growing or regenerating a plant from the plant cell or plant protoplast including an altered target nucleotide sequence, wherein the grown or regenerated plant contains at least some cells or tissues having the altered target nucleotide sequence. In embodiments, callus is produced from the plant cell or plant protoplast, and plantlets and plants produced from such callus. In other embodiments, whole seedlings or plants are grown directly from the plant cell or plant protoplast without a callus stage. Thus, additional related aspects are directed to whole seedlings and plants grown or regenerated from the plant cell or plant protoplast including an altered target nucleotide sequence, as well as the seeds of such plants. In embodiments, the grown or regenerated plant exhibits a phenotype associated with the altered target nucleotide sequence. In embodiments, the grown or regenerated plant includes in its genome two or more genetic modifications that in combination provide at least one phenotype of interest, wherein at least one genetic modification includes the altered target nucleotide sequence in the plant cell or plant protoplast. In embodiments, a heterogeneous population of plant cells or plant protoplasts, at least some of which include one or more altered target nucleotide sequences, is provided by the method; related aspects include a plant having a phenotype of interest associated with the altered target nucleotide sequence, provided by either regeneration of a plant having the phenotype of interest from a plant cell or plant protoplast selected from the heterogeneous population of plant cells or plant protoplasts, or by selection of a plant having the phenotype of interest from a heterogeneous population of plants grown or regenerated from the population of plant cells or plant protoplasts. Examples of phenotypes of interest include herbicide resistance, improved tolerance of abiotic stress (e. g., tolerance of temperature extremes, drought, or salt) or biotic stress (e. g., resistance to bacterial or fungal pathogens), improved utilization of nutrients or water, modified lipid, carbohydrate, or protein composition, improved flavour or appearance, improved storage characteristics (e. g., resistance to bruising, browning, or softening), increased yield, altered morphology (e. g., floral architecture or colour, plant height, branching, root structure). In an embodiment, a heterogeneous population of plant cells or plant protoplasts (or seedlings or plants grown or regenerated therefrom) is exposed to conditions permitting expression of the phenotype of interest; e. g., selection for herbicide resistance can include exposing the population of plant cells or plant protoplasts (or seedlings or plants) to an amount of herbicide or other substance that inhibits growth or is toxic, allowing identification and selection of those resistant plant cells or plant protoplasts (or seedlings or plants) that survive treatment. Also contemplated are heterogeneous populations, arrays, or libraries of such plants, succeeding generations or seeds of such plants grown or regenerated from the plant cells or plant protoplasts, parts of the plants (including plant parts used in grafting as scions or rootstocks), or products (e. g., fruits or other edible plant parts, cleaned grains or seeds, edible oils, flours or starches, proteins, and other processed products) made from the plants or their seeds. Embodiments include plants grown or regenerated from the plant cells or plant protoplasts, wherein the plants contain cells or tissues that do not have the altered nucleotide sequence, e. g., grafted plants in which the scion or rootstock contains the altered nucleotide sequence, or chimeric plants in which some but not all cells or tissues contain the altered nucleotide sequence. Plants in which grafting is commonly useful include many fruit trees and plants such as many citrus trees, apples, stone fruit (e. g., peaches, apricots, cherries, and plums), avocados, tomatoes, eggplant, cucumber, melons, watermelons, and grapes as well as various ornamental plants such as roses. Grafted plants can be grafts between the same or different (generally related) species. Additional related aspects include a hybrid plant provided by crossing a first plant grown or regenerated from a plant cell or plant protoplast with an altered target nucleotide sequence, with a second plant, wherein the hybrid plant contains the altered target nucleotide sequence; also contemplated is seed produced by the hybrid plant.

Delivery of Effector Molecules to a Plant Cell or Plant Protoplast

In related aspects, the delivery techniques, delivery agents, and compositions disclosed above under the heading "Methods of altering a target nucleotide sequence in a plant cell or plant protoplast" are useful in general for delivering other molecules to effect an alteration in a nucleotide sequence in a plant cell or plant protoplast. Such "effector molecules" include other nucleases or polynucleotides encoding a nuclease capable of effecting site-specific alteration of a target nucleotide sequence, and guide polynucleotides that guide nucleases in a sequence-specific manner to a target nucleotide sequence.

Thus, a related aspect of the invention is a method of providing a plant cell or plant protoplast having a genetic alteration, including: (a) delivery of at least one effector molecule to a plant cell or plant protoplast, resulting in a genetic alteration of the plant cell or plant protoplast, wherein the plant cell is obtained from a monocot or a dicot; wherein the effector molecule is at least one selected from the group consisting of: (i) a polynucleotide selected from the group consisting of an RNA guide for an RNA-guided nuclease, a DNA encoding an RNA guide for an RNA-guided nuclease; (ii) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), Argonaute, a meganuclease or engineered meganuclease; or (iii) a polynucleotide encoding one or more nucleases capable of effecting site-specific alteration of a target nucleotide sequence; wherein delivery comprises at least one treatment selected from the group consisting of at least one treatment selected from the group consisting of: direct application; soaking or imbibition; vacuum infiltration; application of negative or positive pressure; introduction into the vascular system; microinjection; application of ultrasound or vibration; application of hydrodynamic pressure, friction, cavitation or shear stress; vortexing; centrifugation; mechanical cell wall or cell membrane deformation or breakage; enzymatic cell wall or cell membrane breakage or permeabilization; abrasion; electroporation; and treatment with at least one chemical, enzymatic, or physical agent; thereby resulting in a genetic alteration in the plant cell or plant protoplast.

In embodiments, the plant cell or plant protoplast in which the genetic alteration is desired is a plant cell or a plant protoplast obtained or isolated from a plant or part of a plant selected from the group consisting of a whole plant, a plant tissue, leaf, root, stem, flower, an intact nodal bud, a shoot apex or shoot apical meristem, a root apex or root apical meristem, lateral meristem, intercalary meristem, a seedling (e. g., a germinating seed or small seedling or a larger seedling with one or more true leaves), a whole seed (e. g., an intact seed, or a seed with part or all of its seed coat removed or treated to make permeable), a halved seed or other seed fragment, an embryo (e. g., a mature dissected zygotic embryo, a developing embryo, a dry or rehydrated or freshly excised embryo), and callus.

In embodiments, delivery of the at least one effector molecule alters a target nucleotide sequence in the plant cell or plant protoplast, resulting in a genetic alteration such as insertion of a nucleotide, deletion of a nucleotide, or replacement of a nucleotide. In embodiments, insertion of a nucleotide includes insertion of one or more nucleotides resulting in a heterologous sequence (that is to say, insertion of one or more nucleotides resulting in a sequence that does not normally occur at the locus of insertion). In embodiments, alteration of the target nucleotide sequence results in a change in expression (e. g., increase or decrease of expression or change in temporal or spatial specificity) of the target nucleotide sequence, methylation or demethylation of the target nucleotide sequence (e. g., resulting in an epigenetic change), a phenotype that is detectable in the plant cell or plant protoplast, or a combination of these. In embodiments, alteration of the target nucleotide sequence results in a phenotype or trait of interest observable in a seedling or plant grown or regenerated from the plant cell or plant protoplast; in some embodiments the phenotype or trait is heritable to succeeding generations of plants. Thus, related embodiments include such succeeding generations of plants or their seeds having inherited the altered target nucleotide sequence.

The target nucleotide sequence is one or more nucleotide sequences, including protein-coding sequence or non-coding sequence or a combination thereof. Embodiments include a plant nuclear sequence, a plant plastid sequence, a plant mitochondrial sequence, a sequence of a symbiont, pest, or pathogen of a plant, and combinations thereof. In embodiments, multiple target nucleotide sequences are altered, for example, by delivery of multiple effector molecules to the plant cell; the multiple target nucleotide sequences can be part of the same gene (e. g., different locations in a single coding region or in different exons of a protein-coding gene) or different genes.

Embodiments of effector molecules include: (a) a polynucleotide selected from the group consisting of an RNA guide for an RNA-guided nuclease, a DNA encoding an RNA guide for an RNA-guided nuclease; (b) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), Argonaute, a meganuclease or engineered meganuclease; or (c) a polynucleotide encoding one or more nucleases capable of effecting site-specific alteration of a target nucleotide sequence. Any of these nucleases can be codon-optimized, e. g., plant-codon-optimized to function optimally in a plant cell. In embodiments, one or multiple effector molecules are delivered individually (e. g., in separate compositions) or in combinations (e. g., in a ribonucleoprotein), and in a single step or multiple steps.

Zinc finger nucleases (ZFNs) are engineered proteins comprising a zinc finger DNA-binding domain fused to a nucleic acid cleavage domain, e. g., a nuclease. The zinc finger binding domains provide specificity and can be engineered to specifically recognize any desired target DNA sequence. For a review of the construction and use of ZFNs in plants and other organisms, see, e. g., Urnov et al. (2010) *Nature Rev. Genet.,* 11:636-646. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotides bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e. g., U.S. Pat. Nos. 6,453,242 and 6,534,261, both incorporated herein by reference in their entirety. Exemplary selection methods (e. g., phage display and yeast two-hybrid systems) are well known and described in the literature. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e. g., see U.S. Pat. Nos. 6,479,626; 6,903,185; and 7,153,949, incorporated herein by reference in their entirety. The nucleic acid cleavage domain is non-specific and is typically a restriction endonuclease, such as Fokl. This endonuclease must dimerize to cleave DNA. Thus, cleavage by Fokl as part of a ZFN requires two adjacent and independent binding events, which must occur in both the correct orientation and with appropriate spacing to permit dimer formation. The requirement for two DNA binding events enables more specific targeting of long and potentially unique recognition sites. Fokl variants with enhanced activities have been described; see, e. g., Guo et al. (2010) *J. Mol. Biol.,* 400:96-107.

Transcription activator like effectors (TALEs) are proteins secreted by certain *Xanthomonas* species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as Fokl, can be conveniently used. For a description of the use of TALENs in plants, see Mahfouz et al. (2011) *Proc. Natl. Acad. Sci. USA,* 108:2623-2628 and Mahfouz (2011) *GM Crops,* 2:99-103.

Argonautes are proteins that can function as sequence-specific endonucleases by binding a polynucleotide (e. g., a single-stranded DNA or single-stranded RNA) that includes sequence complementary to a target nucleotide sequence) that guides the Argonaut to the target nucleotide sequence and effects site-specific alteration of the target nucleotide sequence; see, e. g., US Patent Application Publication 2015/0089681, incorporated herein by reference in its entirety.

In related embodiments, zinc finger nucleases, TALENs, and Argonautes are used in conjunction with other functional domains. For example, the nuclease activity of these nucleic acid targeting systems can be altered so that the enzyme binds to but does not cleave the DNA. Examples of functional domains include transposase domains, integrase domains, recombinase domains, resolvase domains, invertase domains, protease domains, DNA methyltransferase domains, DNA hydroxylmethylase domains, DNA demethylase domains, histone acetylase domains, histone deacetylase domains, nuclease domains, repressor domains, activator domains, nuclear-localization signal domains, transcription-regulatory protein (or transcription complex recruiting) domains, cellular uptake activity associated domains, nucleic acid binding domains, antibody presentation domains, histone modifying enzymes, recruiter of histone modifying enzymes; inhibitor of histone modifying enzymes, histone methyltransferases, histone demethylases, histone kinases, histone phosphatases, histone ribosylases, histone deribosylases, histone ubiquitinases, histone deubiquitinases, histone biotinases and histone tail proteases. Non-limiting examples of functional domains include a transcriptional activation domain, a transcription repression domain, and an SHH1, SUVH2, or SUVH9 polypeptide capable of reducing expression of a target nucleotide sequence via epigenetic modification; see, e. g., US Patent Application Publication 2016/0017348, incorporated herein by reference in its entirety. Genomic DNA may also be modified via base editing using a fusion between a catalytically inactive Cas9 (dCas9) is fused to a cytidine deaminase which convert cytosine (C) to uridine (U), thereby effecting a C to T substitution; see Komor et al. (2016) *Nature,* 533:420-424.

In embodiments, the plant cell or plant protoplast is capable of division and differentiation. In embodiments, the plant cell or plant protoplast is diploid or polyploid. In embodiments, the plant cell or plant protoplast is haploid or can be induced to become haploid; examples include but are not limited to a plant cell or plant protoplast obtained or isolated from haploid plants or from reproductive tissues, e. g., flowers, developing flowers or flower buds, ovaries, ovules, megaspores, anthers, pollen, and microspores. In embodiments where the plant cell or plant protoplast is haploid, the method can further include the step of chromosome doubling (e. g., by using a chromosome doubling agent such as colchicine) in the plant cell or plant protoplast including the genetic alteration to produce a doubled haploid plant cell or plant protoplast that is homozygous for the genetic alteration; yet other embodiments include regeneration of a doubled haploid plant from the doubled haploid plant cell or plant protoplast, wherein the regenerated doubled haploid plant is homozygous for the genetic alteration. Thus, aspects of the invention are related to the haploid plant cell or plant protoplast having the genetic alteration as well as a doubled haploid plant cell or plant protoplast or a doubled haploid plant that is homozygous for the genetic alteration. Another aspect of the invention is related to a hybrid plant having at least one parent plant that is a doubled haploid plant provided by the method.

A related aspect of the invention is directed to the plant having a genetic alteration and grown or regenerated from the plant cell or plant protoplast having a genetic alteration provided by the method. In embodiments, the plant is a monocot or a dicot, or is haploid, diploid, polyploid, or doubled haploid. Embodiments include plants that contain cells or tissues that do not have the genetic alteration, e. g., grafted plants in which the scion or rootstock contains the genetic alteration, or chimeric plants in which some but not all cells or tissues contain the genetic alteration. In embodiments, the genetic alteration is heritable to succeeding generations; further aspects thus include seed and progeny plants of the plant having a genetic alteration, wherein the seed or progeny plants contain the genetic alteration, as well as parts of such seed or progeny plants (including plant parts used in grafting as scions or rootstocks), or products (e. g., fruits or other edible plant parts, cleaned grains or seeds, edible oils, flours or starches, proteins, and other processed products) made from the seed or progeny plants. In embodiments, callus is produced from the plant cell or plant protoplast having the genetic alteration, and plantlets and plants produced from such callus. In other embodiments, whole seedlings or plants are grown directly from the plant cell or plant protoplast having the genetic alteration without a callus stage. Thus, additional related aspects are directed to whole seedlings and plants grown or regenerated from the plant cell or plant protoplast having the genetic alteration, as well as the seeds of such plants. In embodiments, the grown or regenerated plant exhibits a phenotype associated with the genetic alteration. Examples of phenotypes of interest include herbicide resistance, improved tolerance of abiotic stress (e. g., tolerance of temperature extremes, drought, or salt) or biotic stress (e. g., resistance to bacterial or fungal pathogens), improved utilization of nutrients or water, modified lipid, carbohydrate, or protein composition, improved flavour or appearance, increased yield, altered morphology (e. g., floral architecture, plant height, branching, root structure). In embodiments, the grown or regenerated plant includes in its genome two or more genetic modifications that in combination provide at least one phenotype of interest, wherein at least one genetic modification includes the genetic alteration in the plant cell or plant protoplast provided by the method.

Methods for Investigating Reverse Genetics

Another aspect of the invention is related to methods for investigating reverse genetics, for example, a method of identifying a nucleotide sequence (or alteration of a nucleotide sequence, such as a native nucleotide sequence) that is associated with a phenotype of interest. In an embodiment, the method includes the steps of altering the genome of a population of plant cells (or plant protoplasts), optionally growing or regenerating a population of calli, seedlings, plantlets, or plants from the population of plant cells, and selecting the plant cells (or grown or regenerated calli, seedlings, plantlets, or plants) exhibiting the phenotype of interest and identifying the nucleotide sequence associated with the phenotype. Embodiments of the method include culturing or growing the plant cells or protoplasts (or calli, seedlings, plantlets, or plants) under conditions that permit expression of the phenotype of interest.

In an embodiment, the method includes the steps of: (a) contacting a population of plant cells (or protoplasts) with a library of gRNAs and optionally with an RNA-guided DNA nuclease, whereby the genome of the plant cells is altered, culturing the population of plant cells under conditions that permit expression of the phenotype of interest, selecting the plant cells that exhibit the phenotype of interest, and identifying the nucleotide sequence or alteration of a nucleotide sequence, wherein the nucleotide sequence thus identified is associated with the phenotype; or (b) contacting a population of plant cells (or protoplasts) with a library of gRNAs and optionally with an RNA-guided DNA nuclease, whereby the genome of the cells is altered, regenerating a population of plants from the population of plant cells, growing the population of plants under conditions that permit expression of the phenotype of interest, selecting the plants that exhibit the phenotype of interest, and identifying the nucleotide sequence or alteration of a nucleotide sequence, wherein the nucleotide sequence thus identified is associated with the phenotype. In embodiments, the plant cells or protoplasts in which the genome is altered are haploid cells (e. g., microspore or other gametophytic cells, or cells of a haploid plant) and the plants regenerated from these cells are haploid plants; in embodiments the method further includes the step of generating doubled-haploid cells or doubled-haploid plants from the haploid cells or plants.

In embodiments, the gRNA is provided as a polynucleotide composition comprising: (i) a CRISPR RNA (crRNA) that includes the gRNA, or a polynucleotide that encodes a crRNA, or a polynucleotide that is processed into a crRNA; or (ii) a single guide RNA (sgRNA) that includes the gRNA, or a polynucleotide that encodes a sgRNA, or a polynucleotide that is processed into a sgRNA. In embodiments, the plant cells or protoplasts contain or express the appropriate RNA-guided DNA nuclease; in other embodiments the RNA-guided DNA nuclease, or a polynucleotide encoding the RNA-guided DNA nuclease, is provided to the plant cells. In embodiments, the nuclease is selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), Argonaute, a meganuclease or engineered meganuclease. Methods and compositions useful for delivering the library of gRNAs or the RNA-guided DNA nuclease are similar to those described under the heading "Methods of altering a target nucleotide sequence in a plant cell".

Compositions and Reaction Mixtures

Another aspect of the invention is related to compositions and reactions mixtures useful for carrying out methods such as those described herein. In one aspect, the invention is related to a composition or a reaction mixture including: (a) at least one plant cell or plant protoplast, which in embodiments is an isolated plant cell or plant protoplast (e. g., a plant cell or plant protoplast isolated from a whole plant or plant part or plant tissue, or an isolated plant cell or plant protoplast in suspension or plate culture); (b) at least one effector molecule for inducing a genetic alteration in the plant cell or plant protoplast, wherein the at least one effector molecule is selected from the group consisting of: (i) a polynucleotide selected from the group consisting of an RNA guide for an RNA-guided nuclease, a DNA encoding an RNA guide for an RNA-guided nuclease; (ii) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), Argonaute, a meganuclease or engineered meganuclease; or (iii) a polynucleotide encoding one or more nucleases capable of effecting site-specific alteration of a target nucleotide sequence; and (c) optionally, at least one delivery agent selected from the group consisting of solvents, fluorocarbons, glycols or polyols, surfactants; primary, secondary, or tertiary amines and quaternary ammonium salts; organosilicone surfactants; lipids, lipoproteins, lipopolysaccharides; acids, bases, caustic agents; peptides, proteins, or enzymes; cell-penetrating peptides; RNase inhibitors; cationic branched or linear polymers; dendrimers; counter-ions, amines or polyamines, osmolytes, buffers, and salts; polynucleotides; transfection agents; antibiotics; non-specific DNA double-strand-break-inducing agents; chelating agents; and antioxidants; particles or nanoparticles, magnetic particles or nanoparticles, abrasive or scarifying agents, needles or microneedles, matrices, and grids. In embodiments, the composition or reaction mixture is heated to a temperature above that at which the plant normally grows, e. g., in the case of a composition or reaction mixture comprising a cell or protoplast of a plant that normally grows between about 20 to about 29 degrees Celsius, heated for at least 10 minutes to between 30 to about 42 degrees Celsius, or to about 37 degrees Celsius.

In another aspect, the invention is related to a composition or a reaction mixture including: (a) at least one plant cell or plant protoplast, which in embodiments is an isolated plant cell or plant protoplast (e. g., a plant cell or plant protoplast isolated from a whole plant or plant part or plant tissue, or an isolated plant cell or plant protoplast in suspension or plate culture); (b) at least one guide RNA (gRNA) having a nucleotide sequence designed to alter a target nucleotide sequence in the plant cell or plant protoplast, wherein the gRNA is provided as a polynucleotide composition including: (i) a CRISPR RNA (crRNA) that includes the gRNA, or a polynucleotide that encodes a crRNA, or a polynucleotide that is processed into a crRNA; or (ii) a single guide RNA (sgRNA) that includes the gRNA, or a polynucleotide that encodes a sgRNA, or a polynucleotide that is processed into a sgRNA; (c) optionally, at least one nuclease, or at least one polynucleotide that encodes the nuclease, wherein the nuclease is selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), Argonaute, a meganuclease or engineered meganuclease; and (d) optionally, at least one delivery agent selected from the group consisting of solvents, fluorocarbons, glycols or polyols, surfactants; primary, secondary, or tertiary amines and quaternary ammonium salts; organosilicone surfactants; lipids, lipoproteins, lipopolysaccharides; acids, bases, caustic agents; peptides, proteins, or enzymes; cell-penetrating peptides; RNase inhibitors; cationic branched or linear polymers; dendrimers; counter-ions, amines or polyamines, osmolytes, buffers, and salts; polynucleotides; transfection agents; antibiotics; non-specific DNA double-strand-break-inducing agents; chelating agents; and antioxidants; particles or nanoparticles, magnetic particles or nanoparticles, abrasive or scarifying agents, needles or microneedles, matrices, and grids. In embodiments, the gRNA is a single guide RNA (sgRNA) that includes the gRNA, wherein the composition further includes an RNA-guided nuclease, and wherein the sgRNA and RNA guided-nuclease are provided as a ribonucleoprotein (RNP) complex. In embodiments, the at least one plant cell or plant protoplast is a population of plant cells or plant protoplasts, the at least one gRNA is two or more sgRNAs, wherein the composition further includes an RNA-guided nuclease, and wherein the two or more sgRNAs are each provided are provided as a ribonucleoprotein (RNP) complex with the RNA guided-nuclease. In embodiments, the composition or reaction mixture is heated to a temperature above that at which the plant normally grows, e. g., in the case of a composition or reaction mixture comprising a cell or protoplast of a plant that normally grows between about 20 to about 29 degrees Celsius, heated for at least 10 minutes to between 30 to about 42 degrees Celsius, or to about 37 degrees Celsius.

In embodiments of these compositions and reaction mixtures, the at least one plant cell or plant protoplast is an isolated plant cell or an isolated plant protoplast; in other embodiments, the at least one plant cell or plant protoplast is a plant cell located in plant tissue, a plant part, or an intact plant, or is a plant cell in callus. In embodiments, the at least one plant cell or plant protoplast is obtained from a monocot or a dicot. In various embodiments, the at least one plant cell or plant protoplast is haploid, diploid, or polyploid.

EXAMPLES

Example 1

This example illustrates techniques for preparing a plant cell or plant protoplast useful in compositions and methods of the invention, for example, in providing a reaction mixture including isolated plant protoplasts, at least one guide RNA (gRNA), and optionally at least one RNA-guided nuclease. More specifically this non-limiting example describes techniques for preparing isolated, viable plant protoplasts from monocot and dicot plants.

The following mesophyll protoplast preparation protocol (modified from one publicly available at molbio[dot]mgh[dot]harvard.edu/sheenweb/protocols_reg[dot]html) is generally suitable for use with monocot plants such as maize (*Zea mays*) and rice (*Oryza sativa*):

Prepare an enzyme solution containing 0.6 molar mannitol, 10 millimolar MES pH 5.7, 1.5% cellulase R10, and 0.3% macerozyme R10. Heat the enzyme solution at 50-55 degrees Celsius for 10 minutes to inactivate proteases and accelerate enzyme solution and cool it to room temperature before adding 1 millimolar $CaCl_2$, 5 millimolar P-mercaptoethanol, and 0.1% bovine serum albumin. Pass the enzyme solution through a 0.45 micrometer filter. Prepare a washing solution containing 0.6 molar mannitol, 4 millimolar MES pH 5.7, and 20 millimolar KCl.

Obtain second leaves of the monocot plant (e. g., maize or rice) and cut out the middle 6-8 centimeters. Stack ten leaf sections and cut into 0.5 millimeter-wide strips without bruising the leaves. Submerge the leaf strips completely in the enzyme solution in a petri dish, cover with aluminum foil, and apply vacuum for 30 minutes to infiltrate the leaf tissue. Transfer the dish to a platform shaker and incubate for an additional 2.5 hours' digestion with gentle shaking (40 rpm). After digestion, carefully transfer the enzyme solution (now containing protoplasts) using a serological pipette through a 35 micrometer nylon mesh into a round-bottom tube; rinse the petri with 5 milliliters of washing solution and filter this through the mesh as well. Centrifuge the protoplast suspension at 1200 rpm, 2 minutes in a swing-bucket centrifuge. Aspirate off as much of the supernatant as possible without touching the pellet; gently wash the pellet once with 20 milliliters washing buffer and remove the supernatant carefully. Gently resuspend the pellet by swirling in a small volume of washing solution, then resuspend in 10-20 milliliters of washing buffer. Place the tube upright on ice for 30 minutes-4 hours (no longer). After resting on ice, remove the supernatant by aspiration and resuspend the pellet with 2-5 milliliters of washing buffer. Measure the concentration of protoplasts using a hemocytometer and adjust the concentration to 2×10≡protoplasts/milliliter with washing buffer.

The following mesophyll protoplast preparation protocol (modified from one described by Niu and Sheen (2012) *Methods Mol. Biol.,* 876:195-206, doi: 10.1007/978-1-61779-809-2_16) is generally suitable for use with dicot plants such as *Arabidopsis thaliana* and brassicas such as kale (*Brassica oleracea*).

Prepare an enzyme solution containing 0.4 M mannitol, 20 millimolar KCl, 20 millimolar MES pH 5.7, 1.5% cellulase R10, and 0.4% macerozyme R10. Heat the enzyme solution at 50-55 degrees Celsius for 10 minutes to inactivate proteases and accelerate enzyme solution, and then cool it to room temperature before adding 10 millimolar $CaCl_2$, 5 millimolar P-mercaptoethanol, and 0.1% bovine serum albumin. Pass the enzyme solution through a 0.45 micrometer filter. Prepare a "W5" solution containing 154 millimolar NaCl, 125 millimolar $CaCl_2$, 5 millimolar KCl, and 2 millimolar MES pH 5.7. Prepare a "MMg solution" solution containing 0.4 molar mannitol, 15 millimolar $MgCl_2$, and 4 millimolar MES pH 5.7.

Obtain second or third pair true leaves of the dicot plant (e. g., a *brassica* such as kale) and cut out the middle section. Stack 4-8 leaf sections and cut into 0.5 millimeter-wide strips without bruising the leaves. Submerge the leaf strips completely in the enzyme solution in a petri dish, cover with aluminum foil, and apply vacuum for 30 minutes to infiltrate the leaf tissue. Transfer the dish to a platform shaker and incubate for an additional 2.5 hours' digestion with gentle shaking (40 rpm). After digestion, carefully transfer the enzyme solution (now containing protoplasts) using a serological pipette through a 35 micrometer nylon mesh into a round-bottom tube; rinse the petri dish with 5 milliliters of washing solution and filter this through the mesh as well. Centrifuge the protoplast suspension at 1200 rpm, 2 minutes in a swing-bucket centrifuge. Aspirate off as much of the supernatant as possible without touching the pellet; gently wash the pellet once with 20 milliliters washing buffer and remove the supernatant carefully. Gently resuspend the pellet by swirling in a small volume of washing solution, then resuspend in 10-20 milliliters of washing buffer. Place the tube upright on ice for 30 minutes-4 hours (no longer). After resting on ice, remove the supernatant by aspiration and resuspend the pellet with 2-5 milliliters of MMg solution. Measure the concentration of protoplasts using a hemocytometer and adjust the concentration to 2×10≡protoplasts/milliliter with MMg solution.

Example 2

This example illustrates a method of delivery of an effector molecule to a plant cell or plant protoplast to effect a genetic change. More specifically, this non-limiting example describes a method of delivering a guide RNA (gRNA) in the form of a ribonucleoprotein (RNP) to isolated plant protoplasts.

The following delivery protocol (modified from one publicly available at molbio[dot]mgh[dot]harvard.edu/sheenweb/protocols_reg[dot]html) is generally suitable for use with monocot plants such as maize (*Zea mays*) and rice (*Oryza sativa*):

Prepare a polyethylene glycol (PEG) solution containing 40% PEG 4000, 0.2 molar mannitol, and 0.1 molar $CaCl_2$. Prepare an incubation solution containing 170 milligram/liter $KH_2PO_4$, 440 milligram/liter $CaCl_2.2H_20$, 505 milligram/liter $KNO_3$, 160 milligram/liter $NH_4NO_3$, 370 milligram/liter $MgSO_4.7H_20$, 0.01 milligram/liter KI, 1 milligram/liter $H_3BO_3$, 0.1 milligram/liter $MnSO_4.4H_2O$, 1 milligram/liter $ZnSO_4.7H_20$, 0.03 milligram/liter $CuSO_4.5H_20$, 1 milligram/liter nicotinic acid, 1 milligram/liter thiamine HCl, 1 milligram/liter pyridoxine HCl, 0.2 milligram/liter folic acid, 0.01 milligram/liter biotin, 1 milligram/liter D-Ca-pantothenate, 100 milligram/liter myo-inositol, 40 grams/liter glucose, 60 grams/liter mannitol, 700 milligram/liter MES, 10 microliter/liter Tween 80, 1 milligram/liter 2,4-D, and 1 milligram/liter 6-benzylaminopurine (BAP); adjust pH to 5.6.

Prepare a crRNA:tracrRNA or guide RNA (gRNA) complex by mixing equal amounts of CRISPR crRNA and tracrRNA (obtainable e. g., as custom-synthesized Alt-R™ CRISPR crRNA and tracrRNA oligonucleotides from Integrated DNA Technologies, Coralville, IA): mix 6 microliters of 100 micromolar crRNA and 6 microliters of 100 micromolar tracrRNA, heat at 95 degrees Celsius for 5 minutes, and then cool the crRNA:tracrRNA complex to room temperature. To the cooled gRNA solution, add 10 micrograms Cas9 nuclease (Aldeveron, Fargo, ND) and incubate 5 minutes at room temperature to allow the ribonucleoprotein (RNP) complex to form. Add the RNP solution to 100 microliters of monocot protoplasts (prepared as described in Example 1) in a microfuge tube; add 5 micrograms salmon sperm DNA (VWR Cat. No.: 95037-160) and an equal volume of the PEG solution. Mix gently by tapping. After 5 minutes, dilute with 880 microliters of washing buffer and mix gently by inverting the tube. Centrifuge 1 minute at 1200 rpm and then remove the supernatant. Resuspend the protoplasts in 1 milliliter incubation solution and transfer to a multi-well plate for incubation. Editing efficiency is improved by incubating the ribonucleoprotein-treated protoplasts at temperatures above that at which normal plant growth occurs, prior to incubation at a temperature at which normal growth occurs. To do this, incubate the protoplasts at a temperature of between about 30 to about 45 degrees Celsius for a period of time, for example, 10, 20, 30, 40, 45, 50, 60 minutes or for even longer periods (generally for incubation at only moderate heat, such as 30, 32, or 35 degrees Celsius), e. g., 2, 3, 4, 5, 6, 8, 10, 12, 18, 24, 30, 36, 40, or 48 hours; this is followed by incubation at a temperature at which normal growth occurs (average room temperature, e. g., 25-26 degrees Celsius). A typical treatment includes incubation for 30 to 120 minutes at 37 degrees Celsius, followed by a longer incubation at 25-26 degrees Celsius. The efficiency of genome editing is assessed by any suitable method such as endonuclease cleavage analysis or sequences, as described elsewhere in this disclosure; efficiency is expressed as a percentage, obtained by dividing the number of cells in which the genome edit is successfully achieved by the total number of cells subjected to the genome editing procedure.

The following delivery protocol (modified from one described by Niu and Sheen (2012) *Methods Mol. Biol.*, 876:195-206, doi: 10.1007/978-1-61779-809-2_16) is generally suitable for use with dicot plants such as *Arabidopsis thaliana* and brassicas such as kale (*Brassica oleracea*):

Prepare a polyethylene glycol (PEG) solution containing 40% PEG 4000, 0.2 molar mannitol, and 0.1 molar $CaCl_2$. Prepare an incubation solution containing 170 milligram/liter $KH_2PO_4$, 440 milligram/liter $CaCl_2.2H_20$, 505 milligram/liter $KNO_3$, 160 milligram/liter $NH_4NO_3$, 370 milligram/liter $MgSO_4.7H_20$, 0.01 milligram/liter KI, 1 milligram/liter $H_3BO_3$, 0.1 milligram/liter $MnSO_4.4H_2O$, 1 milligram/liter $ZnSO_4.7H_20$, 0.03 milligram/liter $CuSO_4.5H_2O$, 1 milligram/liter nicotinic acid, 1 milligram/liter thiamine HCl, 1 milligram/liter pyridoxine HCl, 0.2 milligram/liter folic acid, 0.01 milligram/liter biotin, 1 milligram/liter D-Ca-pantothenate, 100 milligram/liter myo-inositol, 40 grams/liter glucose, 60 grams/liter mannitol, 700 milligram/liter MES, 10 microliter/liter Tween 80, 1 milligram/liter 2,4-D, and 1 milligram/liter 6-benzylaminopurine (BAP); adjust pH to 5.6.

Prepare a crRNA:tracrRNA or guide RNA (gRNA) complex by mixing equal amounts of CRISPR crRNA and tracrRNA (obtainable e. g., as custom-synthesized Alt-R™ CRISPR crRNA and tracrRNA oligonucleotides from Integrated DNA Technologies, Coralville, IA): mix 6 microliters of 100 micromolar crRNA and 6 microliters of 100 micromolar tracrRNA, heat at 95 degrees Celsius for 5 minutes, and then cool the crRNA:tracrRNA complex to room temperature. To the cooled gRNA solution, add 10 micrograms Cas9 nuclease (Aldeveron, Fargo, ND) and incubate 5 minutes at room temperature to allow the ribonucleoprotein (RNP) complex to form. Add the RNP solution to 100 microliters of dicot protoplasts (prepared as described in Example 1) in a microfuge tube; add 5 micrograms salmon sperm DNA (VWR Cat. No.: 95037-160) and an equal volume of the PEG solution. Mix gently by tapping. After 5 minutes, dilute with 880 microliters of washing buffer and mix gently by inverting the tube. Centrifuge 1 minute at 1200 rpm and then remove the supernatant. Resuspend the protoplasts in 1 milliliter incubation solution and transfer to a multi-well plate. Editing efficiency is improved by incubating the ribonucleoprotein-treated protoplasts at temperatures above that at which normal plant growth occurs, prior to incubation at a temperature at which normal growth occurs. To do this, incubate the protoplasts at a temperature of between about 30 to about 45 degrees Celsius for a period of time, for example, 10, 20, 30, 40, 45, 50, 60 minutes or for even longer periods (generally for incubation at only moderate heat, such as 30, 32, or 35 degrees Celsius), e. g., 2, 3, 4, 5, 6, 8, 10, 12, 18, 24, 30, 36, 40, or 48 hours; this is followed by incubation at a temperature at which normal growth occurs (average room temperature, e. g., 25-26 degrees Celsius). A typical treatment includes incubation for 30 to 120 minutes at 37 degrees Celsius, followed by a longer incubation at 25-26 degrees Celsius. The efficiency of genome editing is assessed by any suitable method such as endonuclease cleavage analysis or sequences, as described elsewhere in this disclosure; efficiency is expressed as a percentage, obtained by dividing the number of cells in which the genome edit is successfully achieved by the total number of cells subjected to the genome editing procedure.

The above protocols for delivery of gRNAs as RNPs to plant protoplasts are adapted for delivery of guide RNAs alone to monocot or dicot protoplasts that express Cas9 nuclease by transient or stable transformation; in this case, the guide RNA complex is prepared as before and added to the protoplasts, but no Cas9 nuclease and no salmon sperm DNA is added. The remainder of the procedures are identical.

Example 3

This example illustrates a method of identifying a nucleotide sequence associated with a phenotype of interest. More specifically, this non-limiting example describes delivering a guide RNA (gRNA) in the form of a ribonucleoprotein (RNP) to isolated plant protoplasts, followed by screening to identify the protoplasts in which the target nucleotide sequence has been altered.

Rice (*Oryza sativa*) protoplasts were prepared according to the protocol described in Example 1. Multiple guide RNAs are prepared as described in Example 2 using crRNAs with the sequences provided in Table 1, complexed with a tracrRNA to form the gRNA (crRNA:tracrRNA) complex; the targetted nucleotide sequences are OsADHI (alcohol dehydrogenase 1) and OsLsi2 (a silicon or arsenic efflux exporter). Both the crRNAs and tracrRNA were purchased from Integrated DNA Technologies, Coralville, IA. Ribonucleoprotein (RNP) complexes were then prepared as described in Example 2 using the gRNAs and Cas9 nuclease (Aldevron, Fargo, ND).

TABLE 1

| crRNA | crRNA sequence | SEQ ID NO. |
|---|---|---|
| OsADH1-1 | GCACUUGAUCACCUUCCCUGGUUUUAGAGCUAUGCU | 1 |
| OsADH1-2 | UCCACCUCCUCGAUCACCAGGUUUUAGAGCUAUGCU | 2 |
| OsADH1-3 | GGCCUCCCAGAAGUAGACGUGUUUUAGAGCUAUGCU | 3 |
| OsADH1-4 | GGGAAGGUGAUCAAGUGCAAGUUUUAGAGCUAUGCU | 4 |
| OsADH1-5 | GCCACCGUCGAACCCUUUGGGUUUUAGAGCUAUGCU | 5 |
| OsADH1-6 | GUAAAUGGGCUUCCCGUUGAGUUUUAGAGCUAUGCU | 6 |
| OsADH1-7 | GACAGACUCCCGUGUUCCCUGUUUUAGAGCUAUGCU | 7 |
| OsADH1-8 | GUGAAUUCAGGAGCUGGAGGGUUUUAGAGCUAUGCU | 8 |
| OsADH1-9 | GUACUUGCUGAGAUGACCAAGUUUUAGAGCUAUGCU | 9 |
| OsADH1-10 | GCAACAUGUGUGAUCUGCUCGUUUUAGAGCUAUGCU | 10 |
| OsLsi2-1 | UGGCCGGGAGGAUUCCCAUGGUUUUAGAGCUAUGCU | 11 |
| OsLsi2-2 | AUGGUUCAUGCAGUGCACGGGUUUUAGAGCUAUGCU | 12 |
| OsLsi2-3 | GCUCGAGGACGAACUCGGUGGUUUUAGAGCUAUGCU | 13 |
| OsLsi2-4 | AUGUACUGGAGGGAGCUGGGGUUUUAGAGCUAUGCU | 14 |
| OsLsi2-5 | UAGAAUGUAUAAUUACCCGUGUUUUAGAGCUAUGCU | 15 |
| OsLsi2-6 | CGGGCCUCCCGGGAGCCAUCGUUUUAGAGCUAUGCU | 16 |
| OsLsi2-7 | CAAGCACCUGGGGCGUCUGCGUUUUAGAGCUAUGCU | 17 |
| OsLsi2-8 | GAGAUCAGAUCUUGCCGAUGGUUUUAGAGCUAUGCU | 18 |
| OsLsi2-9 | GAAGGUGAUCUUGCUAUUGAGUUUUAGAGCUAUGCU | 19 |
| OsLsi2-10 | GAAGAUGAGUGAGCUUGCGUGUUUUAGAGCUAUGCU | 20 |

Arrayed screens can be conveniently carried out with protoplasts in multi-well (e. g., 24- or 96-well) plates. In this example, the protoplasts (25 microliters/well) were distributed in a 24-well plate treated with 5 microliters/well of an individual RNP complex according to the protocols described in Example 2. An HBT-sGFP plasmid was used as a transfection control (2 wells) and Cas9 protein without a guide RNA was used as a null control (2 wells); two technical replicas were performed. Efficiency of editing was estimated to be between 20%-30% by a T7E1 endonuclease as described in Example 4.

In embodiments where editing of a target nucleotide sequence is expected to provide an observable phenotype, the phenotype can be used to select the plant cells or protoplasts having the edited sequence. Optionally, the plant cells or plant protoplasts are grown or cultured under conditions that permit expression of the phenotype, allowing selection of the plant cells or plant protoplasts that exhibit the phenotype. For example, rice cells or protoplasts in which the ADH1 gene is disrupted or altered by editing can be exposed to low concentrations of allyl alcohol; cells wherein one or both copies of the ADH1 gene has been disrupted will have increased susceptibility to allyl alcohol toxicity. In another example, rice cells or protoplasts in which the Lsi gene is disrupted or altered by editing are expected to have decreased arsenic content.

Pooled screens are carried out in a similar fashion, except that editing is carried out with multiple guide RNAs (e. g., in the form of multiple RNPs) provided to a complement of plant protoplasts. For example, maize (*Zea mays*, variety B73) protoplasts are treated with a mixture of RNPs for delivering different gRNAs targeting a selection of 2630 transcription factors in 5 families identified in maize (sequences publicly available at grassius [dot]org/tf_browsefamily.html?species=Maize). Those guides that are over-represented at the read-out stage are those that target genes that are identified as candidates for controlling cell division.

Example 4

This example illustrates genome editing in monocot plants and further illustrates a method of identifying a nucleotide sequence associated with a phenotype of interest. More specifically, this non-limiting example describes delivering a guide RNA (gRNA) in the form of a ribonucleoprotein (RNP) to isolated plant protoplasts, followed by screening to identify the protoplasts in which the target nucleotide sequence has been altered.

The target gene selected for editing was the maize (*Zea mays*) alcohol dehydrogenase ADH1 (see www[dot]maizegdb[dot]org/gene_center/gene/GRMZM2G442658) with the partial genomic sequence:

(SEQ ID NO: 21)

```
GAACAGTGCCGCAGTGGCGCTGATCTTGTATGCTATCCTGCAATCGTGGT
GAACTTATTTCTTTTATATCCTTTACTCCCATGAAAAGGCTAGTAATCTT
TCTCGATGTAACATCGTCCAGCACTGCTATTACCGTGTGGTCCATCCGAC
AGTCTGGCTGAACACATCATACGATCTATGGAGCAAAAATCTATCTTCCC
TGTTCTTTAATGAAGGACGTCATTTTCATTAGTATGATCTAGGAATGTTG
CAACTTGCAAGGAGGCGTTTCTTTCTTTGAATTTAACTAACTCGTTGAGT
GGCCCTGTTTCTCGGACGTAAGGCCTTTGCTGCTCCACACATGTCCATTC
GAATTTTACCGTGTTTAGCAAGGGCGAAAAGTTTGCATCTTGATGATTTA
GCTTGACTATGCGATTGCTTTCCTGGACCCGTGCAGCTGCGGTGGCATGG
GAGGCCGGCAAGCCACTGTCGATCGAGGAGGTGGAGGTAGCGCCTCCGCA
GGCCATGGAGGTGCGCGTCAAGATCCTCTTCACCTCGCTCTGCCACACCG
ACGTCTACTTCTGGGAGGCCAAGGTATCTAATCAGCCATCCCATTTGTGA
TCTTTGTCAGTAGATATGATACAACAACTCGCGGTTGACTTGCGCCTTCT
TGGCGGCTTATCTGTCTTAGGGGCAGACTCCCGTGTTCCCTCGGATCTTT
GGCCACGAGGCTGGAGGGTA;
```

the first exon (SEQ ID NO:22), located at nucleotide positions 409-571 of SEQ ID NO:21 is indicated by bold, underlined text and guide RNA (crRNA) sequences were designed to edit this exon.

Maize protoplasts were prepared as described in Example 1. A ribonucleoprotein (RNP) was prepared with Cas9 nuclease (Aldevron, Fargo, ND) and a guide RNA complex of a crRNA (ZmADH1-B) having the sequence GGCCUCCCAGAAGUAGACGUGUUUUAGAGCUAUGCU (SEQ ID NO:23) and a tracrRNA (both purchased from Integrated DNA Technologies, Coralville, IA). This was used for editing the target gene ADH1 in the maize protoplasts following the procedures described in Example 2. Ribonucleoprotein-treated protoplasts were incubated 30 minutes at 37 degrees Celsius, then incubated overnight at 26 degrees Celsius. A T7 endonuclease (T7E1, New England Biolabs, Ipswich, MA) was used to detect on-target editing. In brief, genomic DNA from the protoplasts was amplified by PCR; the amplified products were denatured and re-annealed to allow heteroduplex formation between wild-type or unedited DNA and the edited DNA. T7E1, which recognizes and cleaves mismatched DNA, was used to digest the heteroduplexes, and the resulting cleaved and full-length PCR products are analysed by gel electrophoresis. The primers used for the T7E1 assay had the sequences GAACAGTGCCGCAGTGGCG (forward primer, SEQ ID NO:24) and TACCCTCCAGCCTCGTGGC (reverse primer, SEQ ID NO:25) for an expected amplicon size of 720 base-pairs (i. e., SEQ ID NO:21). Gel electrophoretic analysis demonstrated the presence of the expected cleaved products.

For quantitation of editing efficiency, next-generation sequencing (NGS) analysis was used. A second set of primers were used for CRISPR sequencing; these had the sequences ACTATGCGATTGCTTTCCTGGAC (forward primer, SEQ ID NO:26) and ACCGCGAGTTGTTGTATCATATCT (reverse primer, SEQ ID NO:27) for an expected amplicon size of 230 base-pairs which includes the ADH1 first exon (i. e., ACTATGCGATTGCTTTCCTGGACCCGTGCAGCTGCGGTGGCATGGGAGGC
CGGCAAGCCACTGTCGATCGAGGAGGTGGAGGTAGCGCCTCCGCAGGCCA
TGGAGGTGCGCGTCAAGATCCTCTTCACCTCGCTCTGCCACACCGACGTC
TACTTCTGGGAGGCCAAGGTATCTAATCAGCCATCCCATTTGTGATCTTT
GTCAGTAGATATGATACAACAACTCGCGGT, SEQ ID NO: 28);

the ADH1 first exon (SEQ ID NO:22) is indicated by bold, underlined text. The NGS sequencing results are provided in FIGS. 1A-1C. The editing efficiency was estimated to be 38%.

Another gene selected for editing was the maize (*Zea mays*) Babyboom gene BBM2 (see www[dot]maizegdb[dot]org/gene_center/gene/GRMZM2G141638) with the partial genomic sequence:

(SEQ ID NO: 29)
AACCGGTGTAATACATACTAAGGGCTAGTTTGGGAACCCTGGTTTTCTAA
GGAATTTTATTTTTCCAAAAAAAATAGTTTATTTTTCCTTCGGAAATTAG
GAATCTCTTATAAAATTCGAGTTCCCAAACTATTCCTAATATATATATCA
TACTCTCCATCAGTCTATATATAGATTACATATAGTAAGTATAGAGTATC
TCGCTATCACATAGTGCCACTAATCTTCTGGAGTGTACCAGTTGTATAAA
TATCTATCAGTATCAGCACTACTGTTTGCTGAATACCCCAAAACTCTCTG
CTTGACTTCTCTTCCCTAACCTTTGCACTGTCCAAAATGGCTTCCTGATC
CCCTCACTTCCTCGAATCATTCTAAGAAGAAACTCAAGCCGCTACCATTA
GGGGCAGATTAATTGCTGCACTTTCAGATAATCTACCATGGCCACTGTGA
ACAACTGGCTCGCTTTCTCCCTCTCCCCGCAGGAGCTGCCGCCCTCCCAG
ACGACGGACTCCACGCTCATCTCGGCCGCCACCGCCGACCATGTCTCCGG
CGATGTCTGCTTCAACATCCCCCAAGGTAGCATCTATCTATCTGGCGACA
TACGTG;

promoter sequence (SEQ ID NO:30), located at nucleotide positions 1-254 of SEQ ID NO:29 is indicated by bold, underlined text and guide RNA (crRNA) sequences were designed to edit this non-coding DNA.

Maize protoplasts were prepared as described in Example 1. A ribonucleoprotein (RNP) was prepared with Cas9 nuclease (Aldevron, Fargo, ND) and a guide RNA complex of a crRNA (ZmBBM2-2) having the sequence AAGAGAUUCCUAAUUUCCGAGUUUUAGAGCUAUGCU (SEQ ID NO:31) and a tracrRNA (both purchased from Integrated DNA Technologies, Coralville, IA). This was used for editing the target gene BBM2 in the maize protoplasts following the procedures described in Example 2. Ribonucleoprotein-treated protoplasts were incubated 30 minutes at 37 degrees Celsius, then incubated overnight at 26 degrees Celsius.

For quantitation of editing efficiency, next-generation sequencing (NGS) analysis was used. The primers used for CRISPR sequencing had the sequences GGGAACCCTGGTTTTCTAAG (forward primer, SEQ ID NO:32) and GCAAACAGTAGTGCTGATACTG (reverse primer, SEQ ID NO:33) for an expected amplicon size of 248 base-pairs which includes the BBM2 promoter sequence (i. e.,

GGGAACCCTGGTTTTCTAAGGAATTTTATTTTTCCAAAAAAAATAGTTTA
TTTTTCCTTCGGAAATTAGGAATCTCTTATAAAATTCGAGTTCCCAAACT
ATTCCTAATATATATATCATACTCTCCATCAGTCTATATATAGATTACAT
ATAGTAAGTATAGAGTATCTCGCTATCACATAGTGCCACTAATCTTCTGG
AGTGTACCAGTTGTATAAATATCTATCAGTATCAGCACTACTGTTTGC,
SEQ ID NO: 34);

the BBM2 promoter sequence (SEQ ID NO:30) is indicated by bold, underlined text.

Example 5

This example illustrates genome editing in dicot plants and further illustrates a method of identifying a nucleotide sequence associated with a phenotype of interest. More specifically, this non-limiting example describes delivering a guide RNA (gRNA) in the form of a ribonucleoprotein (RNP) to isolated plant protoplasts, followed by screening to identify the protoplasts in which the target nucleotide sequence has been altered.

The target gene selected for editing was the kale (*Brassica oleracea*) Myb-like transcription factor 2, BoMYBL2 (see www[dot]ocri-genomics[dot]org/cgi-bin/bolbase/gene_detail[dot]cgi?locus=Bol016164 #) with the partial genomic sequence:

(SEQ ID NO: 35)
GAAACCTACCAGTCTCTCCTTTGAAGAAGACATGAACAAAATTAGCCACG
GCGCTCTATCTCGGCCTTCCGGTAACGTTTCTTGTTCAATATTGTTGTAT
TAGCTTTCATATGACCAAATTCTTCATAATTAAAGATCGGTATAGAAGTC
ATAGATTACATATATGTACATTTGCACGGGTGAGTTTGCAACAAATGTCG
TTTTACTTTGTGAAATTTAATCCCTAATCATGTTTTAGGAATGCTGCACC
GTGCC;

the first exon (SEQ ID NO:36) and part of the second exon (SEQ ID NO:37), located respectively at nucleotide positions 32-71 and 239-255 of SEQ ID NO:35, are indicated by bold, underlined text.

Kale protoplasts were prepared as described in Example 1. A ribonucleoprotein (RNP) was prepared with Cas9 nuclease (Aldevron, Fargo, ND) and a guide RNA complex of a crRNA (BoMYBL2-2) having the sequence GAACAAGAAACGUUACCGGAGUUUUAGAGC-UAUGCU (SEQ ID NO:38) and a tracrRNA (both purchased from Integrated DNA Technologies, Coralville, IA). This was used for editing the target gene BoMYBL2 in the kale protoplasts following the procedures described in Example 2. Ribonucleoprotein-treated protoplasts were incubated 30 minutes at 37 degrees Celsius, then incubated overnight at 26 degrees Celsius.

For quantitation of editing efficiency, next-generation sequencing (NGS) analysis was used. The primers used for CRISPR sequencing had the sequences GAAACC-TACCAGTCTCTCCTTTG (forward primer, SEQ ID NO:39) and GGCACGGTGCAGCATTCCTA (reverse primer, SEQ ID NO:40) for an expected amplicon size of 255 base-pairs (i. e., SEQ ID NO:35). The NGS sequencing results are provided in FIGS. 2A-2F. The editing efficiency was estimated to be 21%.

Another gene selected for editing was the kale (*Brassica oleracea*) "*Gigantea*" gene BoGI, transgenic silencing of which has been reported to result in delaying flowering and leaf senescence in broccoli (*Brassica oleracea* L. var. *italica*); see Thiruvengadam et al. (2015) *Plant Mol. Biol. Rep*., doi 10.1007/s11105-015-0852-3). The kale BoGI gene (see www[dot]ocri-genomics[dot]org/cgi-bin/bolbase/gene_detail[dot]cgi?locus=Bol023541 #) has the partial genomic sequence:

```
                                                (SEQ ID NO: 41)
CCGATGGTCTTCAGTTCTCTTCCTTGTTATGGTCTCCCCCACGAGATCCT

CAACAACATAAGGTACTTAACAATAATAAATAAAGCCTCAGATGTCTCAT

CCATGAACCGGTGCTGATTGTCTTTCTCCTTAGGATCAAGTCGTTGCTTA

TGTCGAATACTTTGGTCGGTTCACATCAGAGCAATTCCCTGATGATATTG

CTGAGG;
```

part of the first exon (SEQ ID NO:42) and the second exon (SEQ ID NO:43), located respectively at nucleotide positions 1-60 and 132-203 of SEQ ID NO:41, are indicated by bold, underlined text.

Kale protoplasts were prepared as described in Example 1. A ribonucleoprotein (RNP) was prepared with Cas9 nuclease (Aldevron, Fargo, ND) and a guide RNA complex of a crRNA (BoGI-1) having the sequence UCGUGGGG-GAGACCAUAACAGUUUUAGAGCUAUGCU (SEQ ID NO:44) and a tracrRNA (both purchased from Integrated DNA Technologies, Coralville, IA). This was used for editing the target gene GI in the kale protoplasts following the procedures described in Example 2. Ribonucleoprotein-treated protoplasts were incubated 30 minutes at 37 degrees Celsius, then incubated overnight at 26 degrees Celsius.

For quantitation of editing efficiency, next-generation sequencing (NGS) analysis was used. The primers used for CRISPR sequencing had the sequences CCGATGGTCTTCAGTTCTCT (forward primer, SEQ ID NO:45) and CCTCAGCAATATCATCAGGG (reverse primer, SEQ ID NO:46) for an expected amplicon size of 206 base-pairs (i. e., SEQ ID NO:41). The NGS sequencing results are provided in FIGS. 3A-3C. The editing efficiency was estimated to be 76%.

Example 6

This example illustrates compositions and reaction mixtures useful for delivering at least one effector molecule for inducing a genetic alteration in a plant cell or plant protoplast.

Sequences of plasmids for delivery of Cas9 (Csn1) endonuclease from the *Streptococcus pyogenes* Type II CRISPR/Cas system (SEQ ID NO:136) and for delivery of a single guide RNA (sgRNA) are provided in Tables 2 and 3. In this non-limiting example, the sgRNA targets the endogenous phytoene desaturase (PDS) in soybean, *Glycine max*; one of skill would understand that other sgRNA sequences for alternative target genes could be substituted in the plasmid.

TABLE 2 sgRNA vector (SEQ ID NO: 136), 3079 base pairs DNA

| Nucleotide position in SEQ ID NO: 136 | Description | Comment |
|---|---|---|
| 1-3079 | Intact plasmid | SEQ ID NO: 136 |
| 379-395 | M13 forward primer for sequencing | |
| 412-717 | Glycine max U6 promoter | |
| 717-736 | Glycine max phytoene desaturase targeting sequence (gRNA) | SEQ ID NO: 137 |
| 737-812 | guide RNA scaffold sequence for *S. pyogenes* CRISPR/Cas9 system | SEQ ID NO: 138 |
| 856-874 | M13 reverse primer for sequencing | complement |
| 882-898 | lac repressor encoded by lacI | |
| 906-936 | lac promoter for the *E. coli* lac operon | complement |
| 951-972 | *E. coli* catabolite activator protein (CAP) binding site | |
| 1260-1848 | high-copy-number ColE1/pMB1/pBR322/pUC origin of replication (left direction) | complement |
| 2019-2879 | CDS for bla, beta-lactamase, AmpR | complement; ampicillin selection |
| 2880-2984 | bla promoter | complement |

The sgRNA vector having the sequence of SEQ ID NO:136 contains nucleotides at positions 717-812 encoding a single guide RNA having the sequence of SEQ ID NO:139, which includes both a targeting sequence (gRNA) (SEQ ID NO:137) and a guide RNA scaffold (SEQ ID NO:138); transcription of the sgRNA is driven by a *Glycine max* U6 promoter at nucleotide positions 412-717. The sgRNA vector also includes lac operon and ampicillin resistance sequences for convenient selection of the plasmid in bacterial cultures.

TABLE 3 endonuclease vector (SEQ ID NO: 140), 8569 base pairs DNA

| Nucleotide position in SEQ ID NO: 140 | Description | Comment |
|---|---|---|
| 1-8569 | Intact plasmid | SEQ ID NO: 140 |
| 379-395 | M13 forward primer for sequencing | |
| 419-1908 | Glycine max UbiL promoter | |
| 1917-6020 | Cas9 (Csn1) endonuclease from the *Streptococcus pyogenes* type II CRISPR/Cas system | SEQ ID NO: 141 (encodes protein with sequence of SEQ ID NO: 142) |

TABLE 3-continued

| endonuclease vector (SEQ ID NO: 140), 8569 base pairs DNA | | |
|---|---|---|
| Nucleotide position in SEQ ID NO: 140 | Description | Comment |
| 6033-6053 | nuclear localization signal of SV40 large T antigen | SEQ ID NO: 143 (encodes peptide with sequence of SEQ ID NO: 144 |
| 6065-6317 | nopaline synthase (NOS) terminator and poly(A)signal | |
| 6348-6364 | M13 reverse primer for sequencing | complement |
| 6372-6388 | lac repressor encoded by lacI | |
| 6396-6426 | lac promoter for the *E. coli* lac operon | complement |
| 6441-6462 | *E. coli* catabolite activator protein (CAP) binding site | |
| 6750-7338 | high-copy-number ColE1/pMB1/pBR322/pUC origin of replication (left direction) | complement |
| 7509-8369 | CDS for bla, beta-lactamase, AmpR | complement; ampicillin selection |
| 8370-8474 | bla promoter | complement |

The endonuclease vector having the sequence of SEQ ID NO: 140 contains nucleotides at positions 1917-6020 having the sequence of SEQ ID NO: 141 and encoding the Cas9 nuclease from *Streptococcus pyogenes* that has the amino acid sequence of SEQ ID NO: 142, and nucleotides at positions 6033-6053 having the sequence of SEQ ID NO:143 and encoding the nuclear localization signal (NLS) of simian virus 40 (SV40) large T antigen that has the amino acid sequence of SEQ ID NO:144. Transcription of the Cas9 nuclease and adjacent SV40 nuclear localization signal is driven by a *Glycine max* UbiL promoter at nucleotide positions 419-1908; the resulting transcript including nucleotides at positions 1917-6053 having the sequence of SEQ ID NO:145 encodes a fusion protein having the sequence of SEQ ID NO:146 wherein the Cas9 nuclease is linked through a 4-residue peptide linker to the SV40 nuclear localization signal. The endonuclease vector also includes lac operon and ampicillin resistance sequences for convenient selection of the plasmid in bacterial cultures.

Similar vectors for expression of nucleases and sgRNAs are also described, e. g., in Fauser et al. (2014) *Plant J.,* 79:348-359; and described at www[dot]addgene[dot[org/crispr. It will be apparent to one skilled in the art that analogous plasmids are easily designed to encode other guide polynucleotide or nuclease sequences, optionally including different elements (e. g., different promoters, terminators, selectable or detectable markers, a cell-penetrating peptide, a nuclear localization signal, a chloroplast transit peptide, or a mitochondrial targeting peptide, etc.), and used in a similar manner. Embodiments of nuclease fusion proteins include fusions (with or without an optional peptide linking sequence) between the Cas9 nuclease from *Streptococcus pyogenes* that has the amino acid sequence of SEQ ID NO:142 and at least one of the following peptide sequences: (a) GRKKRRQRRRPPQ ("HIV-1 Tat (48-60)", SEQ ID NO:147), (b) GRKKRRQRRRPQ ("TAT", SEQ ID NO:148), (c) YGRKKRRQRRR ("TAT (47-57)", SEQ ID NO:149), (d) KLALKLALKALKAALKLA ("MAP (KLAL)", SEQ ID NO:150), (e) RQIRIWFQNRRMRWRR ("Penetratin-Arg", SEQ ID NO:151), (f) CSIPPEVKFNKPFVYLI ("antitrypsin (358-374)", SEQ ID NO:152), (g) RRRQRRKKRGGDIMGEWGNEIFGAIAGFLG ("TAT-HA2 Fusion Peptide", SEQ ID NO:153), (h) FVQWFSKFLGRIL-NH2 ("Temporin L, amide", SEQ ID NO:154), (i) LLIILRRRIRKQAHAHSK ("pVEC (Cadherin-5)", SEQ ID NO:155), (j) LGTYTQDFNKFHTFPQTAIGVGAP ("Calcitonin", SEQ ID NO:156), (k) GAAEAAARVYDLGLRRLRQRRRLRRERVRA ("Neurturin", SEQ ID NO:157), (1) MGLGLHLLVLAAALQGAWSQPKKKRKV ("Human P1", SEQ ID NO:158), (m) RQIKIWFQNRRMKWKKGG ("Penetratin", SEQ ID NO:159), poly-arginine peptides including (n) RRRRRRRR ("octo-arginine", SEQ ID NO:160) and (o) RRRRRRRRR ("nono-arginine", SEQ ID NO:161), and (p) KKLFKKILKYLKKLFKKILKYLKKKKKKKK ("(BP100×2)-K8", SEQ ID NO:162); these nuclease fusion proteins are specifically claimed herein, as are analogous fusion proteins including a nuclease selected from Cpf1, CasY, CasX, C2c1, or C2c3 and at least one of the peptides having a sequence selected from SEQ ID NOs:147-162. In other embodiments, such vectors are used to produce a guide RNA (such as one or more crRNAs or sgRNAs) or the nuclease protein; guide RNAs and nucleases can be combined to produce a specific ribonucleoprotein complex for delivery to the plant cell; in an example, a ribonucleoprotein including the sgRNA having the sequence of SEQ ID NO:139 and the Cas9-NLS fusion protein having the sequence of SEQ ID NO:146 is produced for delivery to the plant cell. Related aspects of the invention thus encompass ribonucleoprotein compositions containing the ribonucleoprotein including the sgRNA having the sequence of SEQ ID NO:139 and a Cas9 fusion protein such as the Cas9-NLS fusion protein having the sequence of SEQ ID NO:146, and polynucleotide compositions containing one or more polynucleotides including the sequences of SEQ ID NOs:139 or 145. The above sgRNA and nuclease vectors are delivered to plant cells or plant protoplasts using compositions and methods described in the specification.

A plasmid ("pCas9TPC-GmPDS") having the nucleotide sequence of SEQ ID NO:163 was designed for simultaneous delivery of Cas9 (Csn1) endonuclease from the Streptococcuspyogenes Type II CRISPR/Cas system and a single guide RNA (sgRNA) targeting the endogenous phytoene desaturase (PDS) in soybean, *Glycine max*. In this non-limiting example, the sgRNA targets the endogenous phytoene desaturase (PDS) in soybean, *Glycine max*; one of skill would understand that other sgRNA sequences for alternative target genes could be substituted in the plasmid. The sequences of this plasmid and specific elements contained therein are described in Table 4 below.

TABLE 4

| pCas9TPC-GmPDS vector (SEQ ID NO: 163), 14548 base pairs DNA | | |
|---|---|---|
| Nucleotide position in SEQ ID NO: 163 | Description | Comment |
| 1-14548 | Intact plasmid | SEQ ID NO: 163 |
| 1187-1816 | pVS1 StaA | stability protein from the *Pseudomonas* plasmid pVS1 |
| 2250-3317 | pVS1 RepA | replication protein from the *Pseudomonas* plasmid pVS1 |
| 3383-3577 | pVS1 oriV | origin of replication for the *Pseudomonas* plasmid pVS1 |

TABLE 4-continued

| pCas9TPC-GmPDS vector (SEQ ID NO: 163), 14548 base pairs DNA | | |
|---|---|---|
| Nucleotide position in SEQ ID NO: 163 | Description | Comment |
| 3921-4061 | basis of mobility region from pBR322 | |
| 4247-4835 | high-copy-number ColE1/pMB1/pBR322/pUC origin of replication (left direction) | complement |
| 5079-5870 | aminoglycoside adenylyltransferase (aadA), confers resistance to spectinomycin and streptomycin | complement |
| 6398-6422 | left border repeat from nopaline C58 T-DNA | |
| 6599-6620 | *E. coli* catabolite activator protein (CAP) binding site | |
| 6635-6665 | lac promoter for the *E. coli* lac operon | |
| 6673-6689 | lac repressor encoded by lacI | |
| 6697-6713 | M13 reverse primer for sequencing | |
| 6728-7699 | PcUbi4-2 promoter | |
| 7714-11817 | Cas9 (Csn1) endonuclease from the *Streptococcus pyogenes* type II CRISPR/Cas system | SEQ ID NO: 141 (encodes protein with sequence of SEQ ID NO: 142) |
| 11830-11850 | nuclear localization signal of SV40 large T antigen | SEQ ID NO: 143 (encodes peptide with sequence of SEQ ID NO: 144 |
| 11868-12336 | Pea3A terminator | |
| 12349-12736 | AtU6-26 promoter | |
| 12737-12756 | Glycine max phytoene desaturase targeting sequence (gRNA) | SEQ ID NO: 137 |
| 12757-12832 | guide RNA scaffold sequence for *S. pyogenes* CRISPR/Cas9 system | SEQ ID NO: 138 |
| 12844-12868 | attB2; recombination site for Gateway ® BP reaction | complement |
| 13549-14100 | *Streptomyces hygroscopicus* bar or pat, encodes phosphinothricin acetyltransferase, confers resistance to bialophos or phosphinothricin | |
| 14199-14215 | M13 forward primer, for sequencing | complement |
| 14411-14435 | right border repeat from nopaline C58 T-DNA | |

The pCas9TPC-GmPDS vector having the sequence of SEQ ID NO:163 contains nucleotides at positions 12737-12832 encoding a single guide RNA having the sequence of SEQ ID NO:139, which includes both a targeting sequence (gRNA) (SEQ ID NO:137) and a guide RNA scaffold (SEQ ID NO:138); transcription of the single guide RNA is driven by a AtU6-26 promoter at nucleotide positions 12349-12736. This vector further contains nucleotides at positions 7714-11817 having the sequence of SEQ ID NO:141 and encoding the Cas9 nuclease from *Streptococcus pyogenes* that has the amino acid sequence of SEQ ID NO:142, and nucleotides at positions 11830-11850 having the sequence of SEQ ID NO:143 and encoding the nuclear localization signal (NLS) of simian virus 40 (SV40) large T antigen that has the amino acid sequence of SEQ ID NO:144. Transcription of the Cas9 nuclease and adjacent SV40 nuclear localization signal is driven by a PcUbi4-2 promoter at nucleotide positions 6728-7699; the resulting transcript including nucleotides at positions 7714-11850 having the sequence of SEQ ID NO:145 encodes a fusion protein having the sequence of SEQ ID NO:146 wherein the Cas9 nuclease is linked through a 4-residue peptide linker to the SV40 nuclear localization signal. The pCas9TPC-GmPDS vector also includes lac operon, aminoglycoside adenylyltransferase, and phosphinothricin acetyltransferase sequences for convenient selection of the plasmid in bacterial or plant cultures.

A plasmid ("pCas9TPC-NbPDS") having the nucleotide sequence of SEQ ID NO:164 was designed for simultaneous delivery of Cas9 (Csn1) endonuclease from the *Streptococcus pyogenes* Type II CRISPR/Cas system and a single guide RNA (sgRNA) targeting the endogenous phytoene desaturase (PDS) in *Nicotiana benthamiana*; see Nekrasov et al. (2013) *Nature Biotechnol.*, 31:691-693. In this non-limiting example, the sgRNA targets the endogenous phytoene desaturase (PDS) in *Nicotiana benthamiana*; one of skill would understand that other sgRNA sequences for alternative target genes could be substituted in the plasmid. The sequences of this plasmid and specific elements contained therein are described in Table 5 below.

TABLE 5

| pCas9TPC-NbPDS vector (SEQ ID NO: 164), 14548 base pairs DNA | | |
|---|---|---|
| Nucleotide position in SEQ ID NO: 164 | Description | Comment |
| 1-14548 | Intact plasmid | SEQ ID NO: 164 |
| 1187-1816 | pVS1 StaA | stability protein from the *Pseudomonas* plasmid pVS1 |
| 2250-3317 | pVS1 RepA | replication protein from the *Pseudomonas* plasmid pVS1 |
| 3383-3577 | pVS1 oriV | origin of replication for the *Pseudomonas* plasmid pVS1 |
| 3921-4061 | basis of mobility region from pBR322 | |
| 4247-4835 | high-copy-number ColE1/pMB1/pBR322/pUC origin of replication (left direction) | Complement |
| 5079-5870 | aminoglycoside adenylyltransferase (aadA), confers resistance to spectinomycin and streptomycin | Complement |
| 6398-6422 | left border repeat from nopaline C58 T-DNA | |
| 6599-6620 | *E. coli* catabolite activator protein (CAP) binding site | |
| 6635-6665 | lac promoter for the *E. coli* lac operon | |
| 6673-6689 | lac repressor encoded by lacI | |
| 6697-6713 | M13 reverse primer for sequencing | |
| 6728-7699 | PcUbi4-2 promoter | |
| 7714-11817 | Cas9 (Csn1) endonuclease from the *Streptococcus pyogenes* type II CRISPR/Cas system | SEQ ID NO: 141 (encodes protein with sequence of SEQ ID NO: 142) |
| 11830-11850 | nuclear localization signal of SV40 large T antigen | SEQ ID NO: 143 (encodes peptide with sequence of SEQ ID NO: 144 |
| 11868-12336 | Pea3A terminator | |
| 12349-12736 | AtU6-26 promoter | |
| 12737-12756 | Nicotiana benthamiana phytoene desaturase targeting sequence | SEQ ID NO: 165 |
| 12757-12832 | guide RNA scaffold sequence for *S. pyogenes* CRISPR/Cas9 system | SEQ ID NO: 138 |
| 12844-12868 | attB2; recombination site for Gateway ® BP reaction | Complement |
| 13549-14100 | *Streptomyces hygroscopicus* bar or pat, encodes phosphinothricin acetyltransferase, confers resistance to bialophos or phosphinothricin | |
| 14199-14215 | M13 forward primer, for sequencing | Complement |
| 14411-14435 | right border repeat from nopaline C58 T-DNA | |

The pCas9TPC-NbPDS vector having the sequence of SEQ ID NO: 164 contains nucleotides at positions 12737-

12832 encoding a single guide RNA having the sequence of SEQ ID NO:166, which includes both a targeting sequence (gRNA) (SEQ ID NO: 165) and a guide RNA scaffold (SEQ ID NO:138); transcription of the single guide RNA is driven by a AtU6-26 promoter at nucleotide positions 12349-12736. This vector further contains nucleotides at positions 7714-11817 having the sequence of SEQ ID NO:141 and encoding the Cas9 nuclease from *Streptococcus pyogenes* that has the amino acid sequence of SEQ ID NO:142, and nucleotides at positions 11830-11850 having the sequence of SEQ ID NO:143 and encoding the nuclear localization signal (NLS) of simian virus 40 (SV40) large T antigen that has the amino acid sequence of SEQ ID NO:144. Transcription of the Cas9 nuclease and adjacent SV40 nuclear localization signal is driven by a PcUbi4-2 promoter at nucleotide positions 6728-7699; the resulting transcript including nucleotides at positions 7714-11850 having the sequence of SEQ ID NO:145 encodes a fusion protein having the sequence of SEQ ID NO:146 wherein the Cas9 nuclease is linked through a 4-residue peptide linker to the SV40 nuclear localization signal. The pCas9TPC-NbPDS vector also includes lac operon, aminoglycoside adenylyltransferase, and phosphinothricin acetyltransferase sequences for convenient selection of the plasmid in bacterial or plant cultures.

Example 7

This example illustrates compositions and methods useful for delivering at least one effector molecule for inducing a genetic alteration in a plant cell or plant protoplast. More specifically, this example illustrates use of a ribonucleoprotein composition including an RNA-guided nuclease modified to include peptides on one or both termini; in non-limiting embodiments, the modified RNA-guided nuclease is demonstrated to be delivered directly into plant protoplasts without use of packaging or transfection reagents such as PEG.

In this example, a Cas9 variant “4×NLS-Cas9-2×NLS” is modified to have four tandem copies of a nuclear localization signal (4×NLS) at the N-terminus, and two tandem copies of a nuclear localization signal (2×NLS) as well as a polyhistidine (His) tag at the C terminus. This protein is expressed in a pET15b backbone vector, purified, and stored as a concentrated stock solution.

Three experiments are carried out using protoplasts from etiolated 15-day-old B73 maize plantlets to minimize background autofluorescence. Protoplasts treatments include (1) modified 4×NLS-Cas9-2×NLS nuclease provided as a ribonucleoprotein complex with a fluorescently labelled ATTO 550 tracrRNA/ADH1 crRNA duplex, delivered with PEG as a transfection reagent; (2) modified 4×NLS-Cas9-2×NLS nuclease provided as a ribonucleoprotein complex with a fluorescently labelled ATTO 550 tracrRNA/ADH1 crRNA duplex, delivered with no transfection reagent; (3) unmodified Cas9 nuclease (Aldevron) provided as a ribonucleoprotein complex with a fluorescently labelled ATTO 550 tracrRNA/ADH1 crRNA duplex, delivered with PEG as a transfection reagent; and (4) a nuclease-free control, consisting of only the fluorescently labelled ATTO 550 tracrRNA/ADH1 crRNA duplex, delivered with PEG as a transfection reagent.

The general procedure is as follows: To a 2 milliliter microcentrifuge tube is added 12 microliters of 50 millimolar ATTO 550 tracrRNA/ADH1 crRNA duplex. The appropriate nuclease is then added (10 micrograms of the modified 4×NLS-Cas9-2×NLS nuclease, or 20 micrograms of Cas9 nuclease) and the mixtures incubated at room temperature for 5 minutes. Salmon sperm DNA (0.5 microliters per tube) is added immediately before transfection. Two hundred microliters of protoplasts are added to each tube, mixed gently, and then one volume of this reaction volume of 40% PEG is added to each tube, mixed, and incubated for 5 minutes at room temperature. Two volumes of maize washing solution (see Example 1) is added, and the tubes inverted to mix. The protoplasts are centrifuged 2 minutes at 1200 rpm, the supernatant discarded, and the protoplasts resuspended in 1 milliliter YPIM containing 50 micromolar calcium cations. Protoplasts are plated in a 6-well plate coated with 5% calf serum and the plate edges wrapped in Parafilm. The plates are incubated for 1 hour at 37 degrees Celsius, then overnight at 25 degrees Celsius, protected from light.

The following results are observed using fluorescent imaging on a Nikon microscope: Protoplasts treated with the unmodified Cas9 ribonucleoprotein show good transfection with the expected red fluorescence within the nucleus. The modified 4×NLS-Cas9-2×NLS ribonucleoprotein is also observed to transfect the cells with the expected red fluorescence observed within the nucleus, with or without PEG treatment. Similar results are observed in two additional replicated experiments, demonstrating that the modified 4×NLS-Cas9-2×NLS ribonucleoprotein is delivered to the nucleus of plant protoplasts without any additional transfection reagents.

Example 8

This example illustrates compositions and methods useful for delivering at least one effector molecule for inducing a genetic alteration in a plant cell or plant protoplast. More specifically, this example illustrates use of various delivery agents in the delivery of polynucleotides or proteins into plant cells or protoplasts.

Over fifty commercially available reagents including several different chemical classes (e. g., reagents including lipids or polymers) are evaluated for the ability to increase delivery of polynucleotide or protein effector molecules (e. g., DNA or RNA molecules or nucleases or ribonucleoproteins) for inducing a genetic alteration in a plant cell or protoplast.

The test system uses green fluorescent protein (GFP) as a report, delivered as DNA (a plasmid) encoding GFP, or as mRNA encoding GFP, or as the GFP protein itself. Maize B73 protoplasts (250 microliters/well in a 24-well plate using a protoplast suspension of 2×10/\5 viable cells/milliliter YPIM medium containing 50 micromolar calcium) are treated with the different reagents and incubated overnight. GFP expression is measured 18 hours after transfection. Wells treated with the following reagents are observed to result in observable transfection (GFP signal) when viewed under a fluorescence microscope, when compared to a null control.

| Form of GFP | Reagent |
|---|---|
| plasmid | Lipofectamine 2000 CD*, Plus reagent* (Thermo Fisher Scientific, Waltham, MA)<br>Lipofectamine LTX*, Plus reagent* (Thermo Fisher Scientific, Waltham, MA)<br>Lipofectamine LTX* (Thermo Fisher Scientific, Waltham, MA), 50 micromolar calcium<br>Lipofectamine LTX* (Thermo Fisher Scientific, Waltham, MA), 25 micromolar calcium |

-continued

| Form of GFP | Reagent |
|---|---|
| mRNA | Lipofectamine 2000*<br>DOTAP Liposomal Transfection Reagent (Sigma-Aldrich, St. Louis, MO)<br>JetMessenger ® (Polyplus-transfection ® SA, Illkirch, France)<br>Xfect RNA (Takara Bio USA, Inc., Mountain View, CA) |

Example 9

This example illustrates compositions and methods useful for delivering at least one effector molecule for inducing a genetic alteration in a plant cell. More specifically, this example illustrates cell wall treatments to effect improved delivery into intact plant cells of effector molecules (e. g., an RNA-guided nuclease or ribonucleoprotein including an RNA-guided nuclease or a crRNA or gRNA or sgRNA) designed to alter a target nucleotide sequence in the plant cell.

Intact plant cells, that is to say, plant cells that still have a fully or largely intact cell wall (in contrast to plant protoplasts), such as plant cells isolated (e. g., using mechanical treatments such as those described in Examples 1 and 2) from plant tissue or plant callus, or plant cells located within plant tissue or plant callus, benefit from one or more cell wall treatments, that is to say, a treatment to assist effector molecules to penetrate through the plant cell wall and thereby alter a target nucleotide sequence in the plant cells. Such cell wall treatments can precede, occur concurrently with, or follow application of the effector molecules, and can include use of compositions including chemical agents such as solvents, fluorocarbons, glycols or polyols, surfactants; primary, secondary, or tertiary amines and quaternary ammonium salts; organosilicone surfactants; lipids, lipoproteins, lipopolysaccharides; acids, bases, caustic agents; peptides, proteins, or enzymes; cell-penetrating peptides; RNase inhibitors; cationic branched or linear polymers; dendrimers; counter-ions, amines or polyamines, osmolytes, buffers, and salts; polynucleotides; transfection agents; antibiotics; non-specific DNA double-strand-break-inducing agents; chelating agents; and antioxidants. Non-limiting embodiments of such treatments include treatment with enzymes (e. g., a cellulase, a pectin lyase, a xylanase, or a combination thereof); or chemical agents (e. g., chelating agents such as ammonium oxalate, ethylenediaminetetraacetic acid ("EDTA"), ethylene glycol-bis(beta-aminoethyl ether)-N,N,N',N'-tetraacetic acid ("EGTA"), or cyclohexane diamine tetraacetate; polypeptides such as cell-penetrating peptides or expansions; non-specific double-stranded or single-stranded polynucleotides such as salmon sperm DNA; surfactants such as Silwet L77 and other silicone surfactants; lipids, such as cationic lipids). One non-limiting method of enzymatic treatment is to incubate about 500 milligrams wet weight fresh plant cells (mechanically dissociated from tissue or callus) in 2 milliliters 0.5 molar mannitol with the enzyme(s) or chemical agent(s) added; after 10 minutes to 4 hours incubation at room temperature, the cells are filtered through a mesh and washed repeatedly with fresh MS medium; see also Examples 1 and 2 for embodiments of enzymatic treatments. In embodiments, the plant cells in which a nucleotide sequence is targetted for alteration are made more physically accessible to such treatments, e. g., by physical removal of plant tissue by dissection to expose the targetted cells to a chemical, enzymatic, or physical treatment (such as cutting, abrasion, ultrasound, mechanical cell wall or cell membrane deformation or breakage, application of shear force, centrifugation, negative or positive pressure, or cold or heat treatment). The enzymatic or chemical agents can be delivered to the targetted cells by means of a pipette, needle, sprayer, and the like.

All cited patents and patent publications referred to in this application are incorporated herein by reference in their entirety. All of the materials and methods disclosed and claimed herein can be made and used without undue experimentation as instructed by the above disclosure and illustrated by the examples. Although the materials and methods of this invention have been described in terms of embodiments and illustrative examples, it will be apparent to those of skill in the art that substitutions and variations can be applied to the materials and methods described herein without departing from the concept, spirit, and scope of the invention. For instance, while the particular examples provided illustrate the methods and embodiments described herein using a specific plant, the principles in these examples are applicable to any plant of interest. All such similar substitutes and modifications apparent to those skilled in the art are deemed to be within the spirit, scope, and concept of the invention as encompassed by the embodiments of the inventions recited herein and the specification and appended claims.

What is claimed:

1. A method of altering a target nucleotide sequence in a population of protoplasts of a plant, comprising delivering a preassembled ribonucleoprotein composition into the population of protoplasts, wherein the preassembled ribonucleoprotein composition comprises:

(a) an RNA-guided nuclease protein, and (b) a guide RNA (gRNA) that has a nucleotide sequence designed to alter a target nucleotide sequence in the population of protoplasts, and is provided as:

(i) a CRISPR RNA (crRNA) that comprises the gRNA, or (ii) a single guide RNA (sgRNA) that comprises the gRNA;

wherein the RNA-guided nuclease protein of (a) is complexed with the gRNA of (b); and wherein the delivering comprises contacting the population of protoplasts with the preassembled ribonucleoprotein composition and concurrently incubating the population of protoplasts at 37 degrees Celsius for a period of between 10 minutes to about 2 hours, thereby altering the target nucleotide sequence.

2. The method of claim 1, wherein the incubating of the population of protoplasts at 37 degrees Celsius for a period of between 10 minutes to about 2 hours is followed by a further incubation at a temperature at which the plant normally grows.

3. The method of claim 1, wherein the RNA-guided nuclease is selected from the group consisting of an RNA-guided DNA endonuclease, a type II Cas nuclease, a Cas9, a type V Cas nuclease, a Cpf1, a CasY, a CasX, a C2c1, a C2c3, an engineered nuclease, and a codon-optimized nuclease.

4. The method of claim 1, wherein the population of protoplasts is:

obtained from a monocot or a dicot;

obtained from an inbred crop plant comprising an elite strain of germplasm, or from a hybrid crop plant that is the progeny of at least one elite strain of germplasm; or a population of isolated plant protoplasts.

5. The method of claim 1, wherein the population of protoplasts is obtained from a plant tissue, whole plant, intact nodal bud, shoot apex or shoot apical meristem, root apex or root apical meristem, lateral meristem, intercalary meristem, seedling, whole seed, halved seed or other seed fragment, embryo, ovule, anther, pollen, microspore, hypocotyl, cotyledon, leaf, petiole, stem, root, callus, or plant cell suspension.

6. The method of claim 1, wherein the contacting comprises at least one treatment selected from the group consisting of: direct application; soaking or imbibition; vacuum infiltration; application of negative or positive pressure; microinjection; application of ultrasound or vibration; application of hydrodynamic pressure, friction, cavitation or shear stress; vortexing; centrifugation; mechanical cell membrane deformation or breakage; enzymatic cell membrane breakage or permeabilization; abrasion; and electroporation.

7. The method of claim 1, wherein the preassembled ribonucleoprotein composition further comprises a chemical agent or a physical agent or a combination of both chemical and physical agents, or the method further comprises a step of treating the population of protoplasts with a chemical agent or a physical agent or a combination of both chemical and physical agents;

wherein the chemical agent is at least one selected from the group consisting of solvents, fluorocarbons, glycols or polyols, surfactants; primary, secondary, or tertiary amines and quaternary ammonium salts; organosilicone surfactants; lipids, lipoproteins, lipopolysaccharides; acids, bases, caustic agents; peptides, proteins, or enzymes; cell-penetrating peptides; RNase inhibitors; cationic branched or linear polymers; dendrimers; counter-ions, amines or polyamines, osmolytes, buffers, and salts; polynucleotides; transfection agents; antibiotics; non-specific DNA double-strand-break-inducing agents; chelating agents; and antioxidants; and wherein the physical agent is at least one selected from the group consisting of particles or nanoparticles, magnetic particles or nanoparticles, abrasive or scarifying agents, needles or microneedles, matrices, and grids.

8. The method of claim 1, wherein:

the preassembled ribonucleoprotein composition further comprises at least one peptide selected from the group consisting of a cell-penetrating peptide, viral movement protein, or transfecting peptide;

the RNA-guided nuclease is provided as a fusion protein comprising the RNA-guided nuclease and at least one peptide selected from the group consisting of a cell-penetrating peptide, viral movement protein, or transfecting peptide;

the preassembled ribonucleoprotein composition is provided on a carrier molecule or a particulate; or the preassembled ribonucleoprotein composition is provided in a liposome, micelle, protoplast or protoplast fragment.

9. The method of claim 1, wherein the preassembled ribonucleoprotein composition comprises a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof.

10. The method of claim 1, further comprising growth or regeneration of a plant from the population of protoplasts comprising the altered target nucleotide sequence, wherein the plant comprises cells having the altered target nucleotide sequence.

11. The method of claim 1, wherein the population of protoplasts are haploid, wherein the method further comprises the step of chromosome doubling in the population of protoplasts comprising the altered target nucleotide sequence to produce a population of doubled haploid cells that is homozygous for the altered target nucleotide sequence.

12. The method of claim 11, further comprising regenerating a doubled haploid plant from the population of doubled haploid cells, wherein the doubled haploid plant comprises cells that are homozygous for the altered target nucleotide sequence.

13. The method of claim 1, wherein the gRNA has a nucleotide sequence designed to alter an alcohol dehydrogenase 1 (ADH1), low silicon rice 2 (Lsi2), babyboom 2 (BBM2), *Brassica oleracea* Myb-like transcription factor 2 (BoMYBL2), or *Brassica oleracea gigantea* 1 (BoGI-1) gene.

14. The method of claim 1, further comprising detecting the altered target nucleotide sequence in at least 20% of the population of protoplasts after the incubating.

15. The method of claim 14, wherein the gRNA comprises one or more of:

(a) SEQ ID NOs: 1 to 20, (b) SEQ ID NO: 23, and (c) SEQ ID NO: 38 and SEQ ID NO: 44.

16. The method of claim 15, wherein the gRNA comprises one or more of SEQ ID NOs: 1 to 20 and the population of protoplasts is a population of *Oryza sativa* protoplasts.

17. The method of claim 15, wherein the gRNA comprises SEQ ID NO: 23 and the population of protoplasts is a population of *Zea mays* protoplasts.

18. The method of claim 15, wherein the gRNA comprises one or more of SEQ ID NO: 38 or SEQ ID NO: 44 and the population of protoplasts is a population of *Brassica oleracea* protoplasts.

19. The method of claim 1, wherein the gRNA comprises SEQ ID NO: 31.

* * * * *

SEQUENCE LISTING

```
<160> NUMBER OF SEQ ID NOS: 166

<210> SEQ ID NO 1
<211> LENGTH: 36
<212> TYPE: RNA
<213> ORGANISM: artificial sequence
<220> FEATURE:
<223> OTHER INFORMATION: synthetic construct

<400> SEQUENCE: 1

gcacuugauc accuucccug guuuuagagc uaugcu                                36


<210> SEQ ID NO 2
<211> LENGTH: 36
<212> TYPE: RNA
```

```
<213> ORGANISM: artificial sequence
<220> FEATURE:
<223> OTHER INFORMATION: synthetic construct

<400> SEQUENCE: 2

uccaccuccu cgaucaccag guuuuagagc uaugcu                              36


<210> SEQ ID NO 3
<211> LENGTH: 36
<212> TYPE: RNA
<213> ORGANISM: artificial sequence
<220> FEATURE:
<223> OTHER INFORMATION: synthetic construct

<400> SEQUENCE: 3

ggccucccag aaguagacgu guuuuagagc uaugcu                              36


<210> SEQ ID NO 4
<211> LENGTH: 36
<212> TYPE: RNA
<213> ORGANISM: artificial sequence
<220> FEATURE:
<223> OTHER INFORMATION: synthetic construct

<400> SEQUENCE: 4

gggaagguga ucaagugcaa guuuuagagc uaugcu                              36


<210> SEQ ID NO 5
<211> LENGTH: 36
<212> TYPE: RNA
<213> ORGANISM: artificial sequence
<220> FEATURE:
<223> OTHER INFORMATION: synthetic construct

<400> SEQUENCE: 5

gccaccgucg aacccuuugg guuuuagagc uaugcu                              36


<210> SEQ ID NO 6
<211> LENGTH: 36
<212> TYPE: RNA
<213> ORGANISM: artificial sequence
<220> FEATURE:
<223> OTHER INFORMATION: synthetic construct

<400> SEQUENCE: 6

guaaaugggc uucccguuga guuuuagagc uaugcu                              36


<210> SEQ ID NO 7
<211> LENGTH: 36
<212> TYPE: RNA
<213> ORGANISM: artificial sequence
<220> FEATURE:
<223> OTHER INFORMATION: synthetic construct

<400> SEQUENCE: 7

gacagacucc cguguucccu guuuuagagc uaugcu                              36


<210> SEQ ID NO 8
<211> LENGTH: 36
<212> TYPE: RNA
<213> ORGANISM: artificial sequence
<220> FEATURE:
<223> OTHER INFORMATION: synthetic construct

<400> SEQUENCE: 8

gugaauucag gagcuggagg guuuuagagc uaugcu                              36
```

<210> SEQ ID NO 9
<211> LENGTH: 36
<212> TYPE: RNA
<213> ORGANISM: artificial sequence
<220> FEATURE:
<223> OTHER INFORMATION: synthetic construct

<400> SEQUENCE: 9
guacuugcug agaugaccaa guuuuagagc uaugcu 36

<210> SEQ ID NO 10
<211> LENGTH: 36
<212> TYPE: RNA
<213> ORGANISM: artificial sequence
<220> FEATURE:
<223> OTHER INFORMATION: synthetic construct

<400> SEQUENCE: 10
gcaacaugug ugaucugcuc guuuuagagc uaugcu 36

<210> SEQ ID NO 11
<211> LENGTH: 36
<212> TYPE: RNA
<213> ORGANISM: artificial sequence
<220> FEATURE:
<223> OTHER INFORMATION: synthetic construct

<400> SEQUENCE: 11
uggccgggag gauucccaug guuuuagagc uaugcu 36

<210> SEQ ID NO 12
<211> LENGTH: 36
<212> TYPE: RNA
<213> ORGANISM: artificial sequence
<220> FEATURE:
<223> OTHER INFORMATION: synthetic construct

<400> SEQUENCE: 12
augguucaug cagugcacgg guuuuagagc uaugcu 36

<210> SEQ ID NO 13
<211> LENGTH: 36
<212> TYPE: RNA
<213> ORGANISM: artificial sequence
<220> FEATURE:
<223> OTHER INFORMATION: synthetic construct

<400> SEQUENCE: 13
gcucgaggac gaacucggug guuuuagagc uaugcu 36

<210> SEQ ID NO 14
<211> LENGTH: 36
<212> TYPE: RNA
<213> ORGANISM: artificial sequence
<220> FEATURE:
<223> OTHER INFORMATION: synthetic construct

<400> SEQUENCE: 14
auguacugga gggagcuggg guuuuagagc uaugcu 36

<210> SEQ ID NO 15
<211> LENGTH: 36
<212> TYPE: RNA
<213> ORGANISM: artificial sequence
<220> FEATURE:

-continued

<223> OTHER INFORMATION: synthetic construct

<400> SEQUENCE: 15
uagaauguau aauuacccgu guuuuagagc uaugcu 36

<210> SEQ ID NO 16
<211> LENGTH: 36
<212> TYPE: RNA
<213> ORGANISM: artificial sequence
<220> FEATURE:
<223> OTHER INFORMATION: synthetic construct

<400> SEQUENCE: 16
cgggccuccc gggagccauc guuuuagagc uaugcu 36

<210> SEQ ID NO 17
<211> LENGTH: 36
<212> TYPE: RNA
<213> ORGANISM: artificial sequence
<220> FEATURE:
<223> OTHER INFORMATION: synthetic construct

<400> SEQUENCE: 17
caagcaccug gggcgucugc guuuuagagc uaugcu 36

<210> SEQ ID NO 18
<211> LENGTH: 36
<212> TYPE: RNA
<213> ORGANISM: artificial sequence
<220> FEATURE:
<223> OTHER INFORMATION: synthetic construct

<400> SEQUENCE: 18
gagaucagau cuugccgaug guuuuagagc uaugcu 36

<210> SEQ ID NO 19
<211> LENGTH: 36
<212> TYPE: RNA
<213> ORGANISM: artificial sequence
<220> FEATURE:
<223> OTHER INFORMATION: synthetic construct

<400> SEQUENCE: 19
gaaggugauc uugcuauuga guuuuagagc uaugcu 36

<210> SEQ ID NO 20
<211> LENGTH: 36
<212> TYPE: RNA
<213> ORGANISM: artificial sequence
<220> FEATURE:
<223> OTHER INFORMATION: synthetic construct

<400> SEQUENCE: 20
gaagaugagu gagcuugcgu guuuuagagc uaugcu 36

<210> SEQ ID NO 21
<211> LENGTH: 720
<212> TYPE: DNA
<213> ORGANISM: Zea mays

<400> SEQUENCE: 21
gaacagtgcc gcagtggcgc tgatcttgta tgctatcctg caatcgtggt gaacttattt 60
cttttatatc ctttactccc atgaaaaggc tagtaatctt tctcgatgta acatcgtcca 120
gcactgctat taccgtgtgg tccatccgac agtctggctg aacacatcat acgatctatg 180

-continued

```
gagcaaaaat ctatcttccc tgttctttaa tgaaggacgt cattttcatt agtatgatct    240

aggaatgttg caacttgcaa ggaggcgttt ctttctttga atttaactaa ctcgttgagt    300

ggccctgttt ctcggacgta aggcctttgc tgctccacac atgtccattc gaattttacc    360

gtgtttagca agggcgaaaa gtttgcatct tgatgattta gcttgactat gcgattgctt    420

tcctggaccc gtgcagctgc ggtggcatgg gaggccggca agccactgtc gatcgaggag    480

gtggaggtag cgcctccgca ggccatggag gtgcgcgtca agatcctctt cacctcgctc    540

tgccacaccg acgtctactt ctgggaggcc aaggtatcta atcagccatc ccatttgtga    600

tctttgtcag tagatatgat acaacaactc gcggttgact tgcgccttct tggcggctta    660

tctgtcttag gggcagactc ccgtgttccc tcggatcttt ggccacgagg ctggagggta    720


<210> SEQ ID NO 22
<211> LENGTH: 163
<212> TYPE: DNA
<213> ORGANISM: Zea mays

<400> SEQUENCE: 22

atgcgattgc tttcctggac ccgtgcagct gcggtggcat gggaggccgg caagccactg     60

tcgatcgagg aggtggaggt agcgcctccg caggccatgg aggtgcgcgt caagatcctc    120

ttcacctcgc tctgccacac cgacgtctac ttctgggagg cca                      163


<210> SEQ ID NO 23
<211> LENGTH: 36
<212> TYPE: RNA
<213> ORGANISM: artificial sequence
<220> FEATURE:
<223> OTHER INFORMATION: synthetic construct

<400> SEQUENCE: 23

ggccucccag aaguagacgu guuuuagagc uaugcu                               36


<210> SEQ ID NO 24
<211> LENGTH: 19
<212> TYPE: DNA
<213> ORGANISM: artificial sequence
<220> FEATURE:
<223> OTHER INFORMATION: synthetic construct

<400> SEQUENCE: 24

gaacagtgcc gcagtggcg                                                  19


<210> SEQ ID NO 25
<211> LENGTH: 19
<212> TYPE: DNA
<213> ORGANISM: artificial sequence
<220> FEATURE:
<223> OTHER INFORMATION: synthetic construct

<400> SEQUENCE: 25

taccctccag cctcgtggc                                                  19


<210> SEQ ID NO 26
<211> LENGTH: 23
<212> TYPE: DNA
<213> ORGANISM: artificial sequence
<220> FEATURE:
<223> OTHER INFORMATION: synthetic construct

<400> SEQUENCE: 26
```

-continued

```
actatgcgat tgctttcctg gac                                            23


<210> SEQ ID NO 27
<211> LENGTH: 24
<212> TYPE: DNA
<213> ORGANISM: artificial sequence
<220> FEATURE:
<223> OTHER INFORMATION: synthetic construct

<400> SEQUENCE: 27

accgcgagtt gttgtatcat atct                                           24


<210> SEQ ID NO 28
<211> LENGTH: 230
<212> TYPE: DNA
<213> ORGANISM: artificial sequence
<220> FEATURE:
<223> OTHER INFORMATION: synthetic construct

<400> SEQUENCE: 28

actatgcgat tgctttcctg gacccgtgca gctgcggtgg catgggaggc cggcaagcca     60

ctgtcgatcg aggaggtgga ggtagcgcct ccgcaggcca tggaggtgcg cgtcaagatc    120

ctcttcacct cgctctgcca caccgacgtc tacttctggg aggccaaggt atctaatcag    180

ccatcccatt tgtgatcttt gtcagtagat atgatacaac aactcgcggt               230


<210> SEQ ID NO 29
<211> LENGTH: 606
<212> TYPE: DNA
<213> ORGANISM: Zea mays

<400> SEQUENCE: 29

aaccggtgta atacatacta agggctagtt tgggaaccct ggttttctaa ggaattttat     60

ttttccaaaa aaaatagttt atttttcctt cggaaattag gaatctctta taaaattcga    120

gttcccaaac tattcctaat atatatatca tactctccat cagtctatat atagattaca    180

tatagtaagt atagagtatc tcgctatcac atagtgccac taatcttctg gagtgtacca    240

gttgtataaa tatctatcag tatcagcact actgtttgct gaataccccca aaactctctg   300

cttgacttct cttccctaac ctttgcactg tccaaaatgg cttcctgatc ccctcacttc    360

ctcgaatcat tctaagaaga aactcaagcc gctaccatta ggggcagatt aattgctgca    420

ctttcagata atctaccatg gccactgtga acaactggct cgctttctcc ctctccccgc    480

aggagctgcc gccctcccag acgacggact ccacgctcat ctcggccgcc accgccgacc    540

atgtctccgg cgatgtctgc ttcaacatcc cccaaggtag catctatcta tctggcgaca    600

tacgtg                                                               606


<210> SEQ ID NO 30
<211> LENGTH: 254
<212> TYPE: DNA
<213> ORGANISM: Zea mays

<400> SEQUENCE: 30

aaccggtgta atacatacta agggctagtt tgggaaccct ggttttctaa ggaattttat     60

ttttccaaaa aaaatagttt atttttcctt cggaaattag gaatctctta taaaattcga    120

gttcccaaac tattcctaat atatatatca tactctccat cagtctatat atagattaca    180

tatagtaagt atagagtatc tcgctatcac atagtgccac taatcttctg gagtgtacca    240

gttgtataaa tatc                                                      254
```

<210> SEQ ID NO 31
<211> LENGTH: 36
<212> TYPE: RNA
<213> ORGANISM: artificial sequence
<220> FEATURE:
<223> OTHER INFORMATION: synthetic construct

<400> SEQUENCE: 31
aagagauucc uaauuuccga guuuuagagc uaugcu 36

<210> SEQ ID NO 32
<211> LENGTH: 20
<212> TYPE: DNA
<213> ORGANISM: artificial sequence
<220> FEATURE:
<223> OTHER INFORMATION: synthetic construct

<400> SEQUENCE: 32
gggaaccctg gttttctaag 20

<210> SEQ ID NO 33
<211> LENGTH: 22
<212> TYPE: DNA
<213> ORGANISM: artificial sequence
<220> FEATURE:
<223> OTHER INFORMATION: synthetic construct

<400> SEQUENCE: 33
gcaaacagta gtgctgatac tg 22

<210> SEQ ID NO 34
<211> LENGTH: 248
<212> TYPE: DNA
<213> ORGANISM: artificial sequence
<220> FEATURE:
<223> OTHER INFORMATION: synthetic construct

<400> SEQUENCE: 34
gggaaccctg gttttctaag gaattttatt tttccaaaaa aaatagttta tttttccttc 60
ggaaattagg aatctcttat aaaattcgag ttcccaaact attcctaata tatatatcat 120
actctccatc agtctatata tagattacat atagtaagta tagagtatct cgctatcaca 180
tagtgccact aatcttctgg agtgtaccag ttgtataaat atctatcagt atcagcacta 240
ctgtttgc 248

<210> SEQ ID NO 35
<211> LENGTH: 255
<212> TYPE: DNA
<213> ORGANISM: Brassica oleracea

<400> SEQUENCE: 35
gaaacctacc agtctctcct ttgaagaaga catgaacaaa attagccacg gcgctctatc 60
tcggccttcc ggtaacgttt cttgttcaat attgttgtat tagctttcat atgaccaaat 120
tcttcataat taaagatcgg tatagaagtc atagattaca tatatgtaca tttgcacggg 180
tgagtttgca acaaatgtcg ttttactttg tgaaatttaa tccctaatca tgttttagga 240
atgctgcacc gtgcc 255

<210> SEQ ID NO 36
<211> LENGTH: 40
<212> TYPE: DNA

<213> ORGANISM: Brassica oleracea

<400> SEQUENCE: 36
atgaacaaaa ttagccacgg cgctctatct cggccttccg 40

<210> SEQ ID NO 37
<211> LENGTH: 17
<212> TYPE: DNA
<213> ORGANISM: Brassica oleracea

<400> SEQUENCE: 37
gaatgctgca ccgtgcc 17

<210> SEQ ID NO 38
<211> LENGTH: 36
<212> TYPE: RNA
<213> ORGANISM: artificial sequence
<220> FEATURE:
<223> OTHER INFORMATION: synthetic construct

<400> SEQUENCE: 38
gaacaagaaa cguuaccgga guuuuagagc uaugcu 36

<210> SEQ ID NO 39
<211> LENGTH: 23
<212> TYPE: DNA
<213> ORGANISM: artificial sequence
<220> FEATURE:
<223> OTHER INFORMATION: synthetic construct

<400> SEQUENCE: 39
gaaacctacc agtctctcct ttg 23

<210> SEQ ID NO 40
<211> LENGTH: 20
<212> TYPE: DNA
<213> ORGANISM: artificial sequence
<220> FEATURE:
<223> OTHER INFORMATION: synthetic construct

<400> SEQUENCE: 40
ggcacggtgc agcattccta 20

<210> SEQ ID NO 41
<211> LENGTH: 206
<212> TYPE: DNA
<213> ORGANISM: Brassica oleracea

<400> SEQUENCE: 41
ccgatggtct tcagttctct tccttgttat ggtctccccc acgagatcct caacaacata 60
aggtacttaa caataataaa taaagcctca gatgtctcat ccatgaaccg gtgctgattg 120
tctttctcct taggatcaag tcgttgctta tgtcgaatac tttggtcggt tcacatcaga 180
gcaattccct gatgatattg ctgagg 206

<210> SEQ ID NO 42
<211> LENGTH: 60
<212> TYPE: DNA
<213> ORGANISM: Brassica oleracea

<400> SEQUENCE: 42
ccgatggtct tcagttctct tccttgttat ggtctccccc acgagatcct caacaacata 60

-continued

<210> SEQ ID NO 43
<211> LENGTH: 72
<212> TYPE: DNA
<213> ORGANISM: Brassica oleracea

<400> SEQUENCE: 43
aggatcaagt cgttgcttat gtcgaatact ttggtcggtt cacatcagag caattccctg 60
atgatattgc tg 72

<210> SEQ ID NO 44
<211> LENGTH: 36
<212> TYPE: RNA
<213> ORGANISM: artificial sequence
<220> FEATURE:
<223> OTHER INFORMATION: synthetic construct

<400> SEQUENCE: 44
ucguggggga gaccauaaca guuuuagagc uaugcu 36

<210> SEQ ID NO 45
<211> LENGTH: 20
<212> TYPE: DNA
<213> ORGANISM: artificial sequence
<220> FEATURE:
<223> OTHER INFORMATION: synthetic construct

<400> SEQUENCE: 45
ccgatggtct tcagttctct 20

<210> SEQ ID NO 46
<211> LENGTH: 20
<212> TYPE: DNA
<213> ORGANISM: artificial sequence
<220> FEATURE:
<223> OTHER INFORMATION: synthetic construct

<400> SEQUENCE: 46
cctcagcaat atcatcaggg 20

<210> SEQ ID NO 47
<211> LENGTH: 230
<212> TYPE: DNA
<213> ORGANISM: artificial sequence
<220> FEATURE:
<223> OTHER INFORMATION: synthetic construct

<400> SEQUENCE: 47
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 48
<211> LENGTH: 230
<212> TYPE: DNA
<213> ORGANISM: artificial sequence
<220> FEATURE:
<223> OTHER INFORMATION: synthetic construct

<400> SEQUENCE: 48
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120

```
ctcttcacct cgctctgcca caccgacgtc tacttctggg aggccaaggt atctaatcag    180

ccatcccatt tgtgatcttt gtcagtagat atgatacaac aactcgcggt               230


<210> SEQ ID NO 49
<211> LENGTH: 230
<212> TYPE: DNA
<213> ORGANISM: artificial sequence
<220> FEATURE:
<223> OTHER INFORMATION: synthetic construct

<400> SEQUENCE: 49

actatgcgat tgctttcctg gacccgtgca gctgcggtgg catgggaggc cggcaagcca     60

ctgtcgatcg aggaggtgga ggtagcgcct ccgcaggcca tggaggtgcg cgtcaagatc    120

ctcttcacct cgctctgcca caccgacgtc tacttctggg aggccaaggt atctaatcag    180

ccatcccatt tgtgatcttt gtcagtagat atgatacaac aactcgcggt               230


<210> SEQ ID NO 50
<211> LENGTH: 230
<212> TYPE: DNA
<213> ORGANISM: artificial sequence
<220> FEATURE:
<223> OTHER INFORMATION: synthetic construct

<400> SEQUENCE: 50

actatgcgat tgctttcctg gacccgtgca gctgcggtgg catgggaggc cggcaagcca     60

ctgtcgatcg aggaggtgga ggtagcgcct ccgcaggcca tggaggtgcg cgtcaagatc    120

ctcttcacct cgctctgcca caccgacgtc tacttctggg aggccaaggt atctaatcag    180

ccatcccatt tgtgatcttt gtcagtagat atgatacaac aactcgcggt               230


<210> SEQ ID NO 51
<211> LENGTH: 230
<212> TYPE: DNA
<213> ORGANISM: artificial sequence
<220> FEATURE:
<223> OTHER INFORMATION: synthetic construct

<400> SEQUENCE: 51

actatgcgat tgctttcctg gacccgtgca gctgcggtgg catgggaggc cggcaagcca     60

ctgtcgatcg aggaggtgga ggtagcgcct ccgcaggcca tggaggtgcg cgtcaagatc    120

ctcttcacct cgctctgcca caccgacgtc tacttctggg aggccaaggt atctaatcag    180

ccatcccatt tgtgatcttt gtcagtagat atgatacaac aactcgcggt               230


<210> SEQ ID NO 52
<211> LENGTH: 230
<212> TYPE: DNA
<213> ORGANISM: artificial sequence
<220> FEATURE:
<223> OTHER INFORMATION: synthetic construct

<400> SEQUENCE: 52

actatgcgat tgctttcctg gacccgtgca gctgcggtgg catgggaggc cggcaagcca     60

ctgtcgatcg aggaggtgga ggtagcgcct ccgcaggcca tggaggtgcg cgtcaagatc    120

ctcttcacct cgctctgcca caccgacgtc tacttctggg aggccaaggt atctaatcag    180

ccatcccatt tgtgatcttt gtcagtagat atgatacaac aactcgcggt               230


<210> SEQ ID NO 53
<211> LENGTH: 230
```

-continued

<212> TYPE: DNA
<213> ORGANISM: artificial sequence
<220> FEATURE:
<223> OTHER INFORMATION: synthetic construct

<400> SEQUENCE: 53
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 54
<211> LENGTH: 230
<212> TYPE: DNA
<213> ORGANISM: artificial sequence
<220> FEATURE:
<223> OTHER INFORMATION: synthetic construct

<400> SEQUENCE: 54
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 55
<211> LENGTH: 230
<212> TYPE: DNA
<213> ORGANISM: artificial sequence
<220> FEATURE:
<223> OTHER INFORMATION: synthetic construct

<400> SEQUENCE: 55
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 56
<211> LENGTH: 230
<212> TYPE: DNA
<213> ORGANISM: artificial sequence
<220> FEATURE:
<223> OTHER INFORMATION: synthetic construct

<400> SEQUENCE: 56
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 57
<211> LENGTH: 230
<212> TYPE: DNA
<213> ORGANISM: artificial sequence
<220> FEATURE:
<223> OTHER INFORMATION: synthetic construct

<400> SEQUENCE: 57

-continued

```
actatgcgat tgctttcctg gacccgtgca gctgcggtgg catgggaggc cggcaagcca     60

ctgtcgatcg aggaggtgga ggtagcgcct ccgcaggcca tggaggtgcg cgtcaagatc    120

ctcttcacct cgctctgcca caccgacgtc tacttctggg aggccaaggt atctaatcag    180

ccatcccatt tgtgatcttt gtcagtagat atgatacaac aactcgcggt               230
```

```
<210> SEQ ID NO 58
<211> LENGTH: 230
<212> TYPE: DNA
<213> ORGANISM: artificial sequence
<220> FEATURE:
<223> OTHER INFORMATION: synthetic construct

<400> SEQUENCE: 58

actatgcgat tgctttcctg gacccgtgca gctgcggtgg catgggaggc cggcaagcca     60

ctgtcgatcg aggaggtgga ggtagcgcct ccgcaggcca tggaggtgcg cgtcaagatc    120

ctcttcacct cgctctgcca caccgacgtc tacttctggg aggccaaggt atctaatcag    180

ccatcccatt tgtgatcttt gtcagtagat atgatacaac aactcgcggt               230
```

```
<210> SEQ ID NO 59
<211> LENGTH: 230
<212> TYPE: DNA
<213> ORGANISM: artificial sequence
<220> FEATURE:
<223> OTHER INFORMATION: synthetic construct

<400> SEQUENCE: 59

actatgcgat tgctttcctg gacccgtgca gctgcggtgg catgggaggc cggcaagcca     60

ctgtcgatcg aggaggtgga ggtagcgcct ccgcaggcca tggaggtgcg cgtcaagatc    120

ctcttcacct cgctctgcca caccgacgtc tacttctggg aggccaaggt atctaatcag    180

ccatcccatt tgtgatcttt gtcagtagat atgatacaac aactcgcggt               230
```

```
<210> SEQ ID NO 60
<211> LENGTH: 230
<212> TYPE: DNA
<213> ORGANISM: artificial sequence
<220> FEATURE:
<223> OTHER INFORMATION: synthetic construct

<400> SEQUENCE: 60

actatgcgat tgctttcctg gacccgtgca gctgcggtgg catgggaggc cggcaagcca     60

ctgtcgatcg aggaggtgga ggtagcgcct ccgcaggcca tggaggtgcg cgtcaagatc    120

ctcttcacct cgctctgcca caccgacgtc tacttctggg aggccaaggt atctaatcag    180

ccatcccatt tgtgatcttt gtcagtagat atgatacaac aactcgcggt               230
```

```
<210> SEQ ID NO 61
<211> LENGTH: 230
<212> TYPE: DNA
<213> ORGANISM: artificial sequence
<220> FEATURE:
<223> OTHER INFORMATION: synthetic construct

<400> SEQUENCE: 61

actatgcgat tgctttcctg gacccgtgca gctgcggtgg catgggaggc cggcaagcca     60

ctgtcgatcg aggaggtgga ggtagcgcct ccgcaggcca tggaggtgcg cgtcaagatc    120

ctcttcacct cgctctgcca caccgacgtc tacttctggg aggccaaggt atctaatcag    180

ccatcccatt tgtgatcttt gtcagtagat atgatacaac aactcgcggt               230
```

-continued

<210> SEQ ID NO 62
<211> LENGTH: 230
<212> TYPE: DNA
<213> ORGANISM: artificial sequence
<220> FEATURE:
<223> OTHER INFORMATION: synthetic construct

<400> SEQUENCE: 62
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 63
<211> LENGTH: 230
<212> TYPE: DNA
<213> ORGANISM: artificial sequence
<220> FEATURE:
<223> OTHER INFORMATION: synthetic construct

<400> SEQUENCE: 63
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 64
<211> LENGTH: 230
<212> TYPE: DNA
<213> ORGANISM: artificial sequence
<220> FEATURE:
<223> OTHER INFORMATION: synthetic construct

<400> SEQUENCE: 64
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 65
<211> LENGTH: 230
<212> TYPE: DNA
<213> ORGANISM: artificial sequence
<220> FEATURE:
<223> OTHER INFORMATION: synthetic construct

<400> SEQUENCE: 65
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 66
<211> LENGTH: 230
<212> TYPE: DNA
<213> ORGANISM: artificial sequence
<220> FEATURE:

<223> OTHER INFORMATION: synthetic construct

<400> SEQUENCE: 66
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 67
<211> LENGTH: 230
<212> TYPE: DNA
<213> ORGANISM: artificial sequence
<220> FEATURE:
<223> OTHER INFORMATION: synthetic construct

<400> SEQUENCE: 67
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 68
<211> LENGTH: 230
<212> TYPE: DNA
<213> ORGANISM: artificial sequence
<220> FEATURE:
<223> OTHER INFORMATION: synthetic construct

<400> SEQUENCE: 68
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 69
<211> LENGTH: 230
<212> TYPE: DNA
<213> ORGANISM: artificial sequence
<220> FEATURE:
<223> OTHER INFORMATION: synthetic construct

<400> SEQUENCE: 69
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 70
<211> LENGTH: 230
<212> TYPE: DNA
<213> ORGANISM: artificial sequence
<220> FEATURE:
<223> OTHER INFORMATION: synthetic construct

<400> SEQUENCE: 70
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 71
<211> LENGTH: 230
<212> TYPE: DNA
<213> ORGANISM: artificial sequence
<220> FEATURE:
<223> OTHER INFORMATION: synthetic construct

<400> SEQUENCE: 71
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 72
<211> LENGTH: 230
<212> TYPE: DNA
<213> ORGANISM: artificial sequence
<220> FEATURE:
<223> OTHER INFORMATION: synthetic construct

<400> SEQUENCE: 72
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 73
<211> LENGTH: 230
<212> TYPE: DNA
<213> ORGANISM: artificial sequence
<220> FEATURE:
<223> OTHER INFORMATION: synthetic construct

<400> SEQUENCE: 73
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 74
<211> LENGTH: 230
<212> TYPE: DNA
<213> ORGANISM: artificial sequence
<220> FEATURE:
<223> OTHER INFORMATION: synthetic construct

<400> SEQUENCE: 74
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 75

<211> LENGTH: 230
<212> TYPE: DNA
<213> ORGANISM: artificial sequence
<220> FEATURE:
<223> OTHER INFORMATION: synthetic construct

<400> SEQUENCE: 75
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 76
<211> LENGTH: 230
<212> TYPE: DNA
<213> ORGANISM: artificial sequence
<220> FEATURE:
<223> OTHER INFORMATION: synthetic construct

<400> SEQUENCE: 76
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 77
<211> LENGTH: 230
<212> TYPE: DNA
<213> ORGANISM: artificial sequence
<220> FEATURE:
<223> OTHER INFORMATION: synthetic construct

<400> SEQUENCE: 77
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 78
<211> LENGTH: 230
<212> TYPE: DNA
<213> ORGANISM: artificial sequence
<220> FEATURE:
<223> OTHER INFORMATION: synthetic construct

<400> SEQUENCE: 78
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 79
<211> LENGTH: 230
<212> TYPE: DNA
<213> ORGANISM: artificial sequence
<220> FEATURE:
<223> OTHER INFORMATION: synthetic construct

<400> SEQUENCE: 79
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 80
<211> LENGTH: 230
<212> TYPE: DNA
<213> ORGANISM: artificial sequence
<220> FEATURE:
<223> OTHER INFORMATION: synthetic construct

<400> SEQUENCE: 80
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 81
<211> LENGTH: 230
<212> TYPE: DNA
<213> ORGANISM: artificial sequence
<220> FEATURE:
<223> OTHER INFORMATION: synthetic construct

<400> SEQUENCE: 81
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 82
<211> LENGTH: 230
<212> TYPE: DNA
<213> ORGANISM: artificial sequence
<220> FEATURE:
<223> OTHER INFORMATION: synthetic construct

<400> SEQUENCE: 82
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 83
<211> LENGTH: 230
<212> TYPE: DNA
<213> ORGANISM: artificial sequence
<220> FEATURE:
<223> OTHER INFORMATION: synthetic construct

<400> SEQUENCE: 83
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 84
<211> LENGTH: 230
<212> TYPE: DNA
<213> ORGANISM: artificial sequence
<220> FEATURE:
<223> OTHER INFORMATION: synthetic construct

<400> SEQUENCE: 84
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 85
<211> LENGTH: 230
<212> TYPE: DNA
<213> ORGANISM: artificial sequence
<220> FEATURE:
<223> OTHER INFORMATION: synthetic construct

<400> SEQUENCE: 85
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 86
<211> LENGTH: 230
<212> TYPE: DNA
<213> ORGANISM: artificial sequence
<220> FEATURE:
<223> OTHER INFORMATION: synthetic construct

<400> SEQUENCE: 86
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 87
<211> LENGTH: 230
<212> TYPE: DNA
<213> ORGANISM: artificial sequence
<220> FEATURE:
<223> OTHER INFORMATION: synthetic construct

<400> SEQUENCE: 87
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 88
<211> LENGTH: 230
<212> TYPE: DNA
<213> ORGANISM: artificial sequence
<220> FEATURE:
<223> OTHER INFORMATION: synthetic construct

<400> SEQUENCE: 88
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 89
<211> LENGTH: 230
<212> TYPE: DNA
<213> ORGANISM: artificial sequence
<220> FEATURE:
<223> OTHER INFORMATION: synthetic construct

<400> SEQUENCE: 89
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 90
<211> LENGTH: 230
<212> TYPE: DNA
<213> ORGANISM: artificial sequence
<220> FEATURE:
<223> OTHER INFORMATION: synthetic construct

<400> SEQUENCE: 90
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 91
<211> LENGTH: 230
<212> TYPE: DNA
<213> ORGANISM: artificial sequence
<220> FEATURE:
<223> OTHER INFORMATION: synthetic construct

<400> SEQUENCE: 91
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 92
<211> LENGTH: 230
<212> TYPE: DNA
<213> ORGANISM: artificial sequence
<220> FEATURE:
<223> OTHER INFORMATION: synthetic construct

<400> SEQUENCE: 92
actatgcgat tgctttcctg gacccgtgca gctgcggtgg catgggaggc cggcaagcca 60

-continued ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 93
<211> LENGTH: 230
<212> TYPE: DNA
<213> ORGANISM: artificial sequence
<220> FEATURE:
<223> OTHER INFORMATION: synthetic construct

<400> SEQUENCE: 93
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 94
<211> LENGTH: 230
<212> TYPE: DNA
<213> ORGANISM: artificial sequence
<220> FEATURE:
<223> OTHER INFORMATION: synthetic construct

<400> SEQUENCE: 94
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 95
<211> LENGTH: 230
<212> TYPE: DNA
<213> ORGANISM: artificial sequence
<220> FEATURE:
<223> OTHER INFORMATION: synthetic construct

<400> SEQUENCE: 95
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 96
<211> LENGTH: 230
<212> TYPE: DNA
<213> ORGANISM: artificial sequence
<220> FEATURE:
<223> OTHER INFORMATION: synthetic construct

<400> SEQUENCE: 96
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

```
<210> SEQ ID NO 97
<211> LENGTH: 230
<212> TYPE: DNA
<213> ORGANISM: artificial sequence
<220> FEATURE:
<223> OTHER INFORMATION: synthetic construct

<400> SEQUENCE: 97

actatgcgat tgctttcctg gacccgtgca gctgcggtgg catgggaggc cggcaagcca      60

ctgtcgatcg aggaggtgga ggtagcgcct ccgcaggcca tggaggtgcg cgtcaagatc     120

ctcttcacct cgctctgcca caccgacgtc tacttctggg aggccaaggt atctaatcag     180

ccatcccatt tgtgatcttt gtcagtagat atgatacaac aactcgcggt                230


<210> SEQ ID NO 98
<211> LENGTH: 230
<212> TYPE: DNA
<213> ORGANISM: artificial sequence
<220> FEATURE:
<223> OTHER INFORMATION: synthetic construct

<400> SEQUENCE: 98

actatgcgat tgctttcctg gacccgtgca gctgcggtgg catgggaggc cggcaagcca      60

ctgtcgatcg aggaggtgga ggtagcgcct ccgcaggcca tggaggtgcg cgtcaagatc     120

ctcttcacct cgctctgcca caccgacgtc tacttctggg aggccaaggt atctaatcag     180

ccatcccatt tgtgatcttt gtcagtagat atgatacaac aactcgcggt                230


<210> SEQ ID NO 99
<211> LENGTH: 230
<212> TYPE: DNA
<213> ORGANISM: artificial sequence
<220> FEATURE:
<223> OTHER INFORMATION: synthetic construct

<400> SEQUENCE: 99

actatgcgat tgctttcctg gacccgtgca gctgcggtgg catgggaggc cggcaagcca      60

ctgtcgatcg aggaggtgga ggtagcgcct ccgcaggcca tggaggtgcg cgtcaagatc     120

ctcttcacct cgctctgcca caccgacgtc tacttctggg aggccaaggt atctaatcag     180

ccatcccatt tgtgatcttt gtcagtagat atgatacaac aactcgcggt                230


<210> SEQ ID NO 100
<211> LENGTH: 230
<212> TYPE: DNA
<213> ORGANISM: artificial sequence
<220> FEATURE:
<223> OTHER INFORMATION: synthetic construct

<400> SEQUENCE: 100

actatgcgat tgctttcctg gacccgtgca gctgcggtgg catgggaggc cggcaagcca      60

ctgtcgatcg aggaggtgga ggtagcgcct ccgcaggcca tggaggtgcg cgtcaagatc     120

ctcttcacct cgctctgcca caccgacgtc tacttctggg aggccaaggt atctaatcag     180

ccatcccatt tgtgatcttt gtcagtagat atgatacaac aactcgcggt                230


<210> SEQ ID NO 101
<211> LENGTH: 230
<212> TYPE: DNA
<213> ORGANISM: artificial sequence
<220> FEATURE:
<223> OTHER INFORMATION: synthetic construct
```

<400> SEQUENCE: 101
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 102
<211> LENGTH: 230
<212> TYPE: DNA
<213> ORGANISM: artificial sequence
<220> FEATURE:
<223> OTHER INFORMATION: synthetic construct

<400> SEQUENCE: 102
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 103
<211> LENGTH: 230
<212> TYPE: DNA
<213> ORGANISM: artificial sequence
<220> FEATURE:
<223> OTHER INFORMATION: synthetic construct

<400> SEQUENCE: 103
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 104
<211> LENGTH: 230
<212> TYPE: DNA
<213> ORGANISM: artificial sequence
<220> FEATURE:
<223> OTHER INFORMATION: synthetic construct

<400> SEQUENCE: 104
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 105
<211> LENGTH: 230
<212> TYPE: DNA
<213> ORGANISM: artificial sequence
<220> FEATURE:
<223> OTHER INFORMATION: synthetic construct

<400> SEQUENCE: 105
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 106
<211> LENGTH: 230
<212> TYPE: DNA
<213> ORGANISM: artificial sequence
<220> FEATURE:
<223> OTHER INFORMATION: synthetic construct

<400> SEQUENCE: 106
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 107
<211> LENGTH: 230
<212> TYPE: DNA
<213> ORGANISM: artificial sequence
<220> FEATURE:
<223> OTHER INFORMATION: synthetic construct

<400> SEQUENCE: 107
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 108
<211> LENGTH: 230
<212> TYPE: DNA
<213> ORGANISM: artificial sequence
<220> FEATURE:
<223> OTHER INFORMATION: synthetic construct

<400> SEQUENCE: 108
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 109
<211> LENGTH: 230
<212> TYPE: DNA
<213> ORGANISM: artificial sequence
<220> FEATURE:
<223> OTHER INFORMATION: synthetic construct

<400> SEQUENCE: 109
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 110
<211> LENGTH: 230
<212> TYPE: DNA

<213> ORGANISM: artificial sequence
<220> FEATURE:
<223> OTHER INFORMATION: synthetic construct

<400> SEQUENCE: 110
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 111
<211> LENGTH: 230
<212> TYPE: DNA
<213> ORGANISM: artificial sequence
<220> FEATURE:
<223> OTHER INFORMATION: synthetic construct

<400> SEQUENCE: 111
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 112
<211> LENGTH: 230
<212> TYPE: DNA
<213> ORGANISM: artificial sequence
<220> FEATURE:
<223> OTHER INFORMATION: synthetic construct

<400> SEQUENCE: 112
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 113
<211> LENGTH: 230
<212> TYPE: DNA
<213> ORGANISM: artificial sequence
<220> FEATURE:
<223> OTHER INFORMATION: synthetic construct

<400> SEQUENCE: 113
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 114
<211> LENGTH: 230
<212> TYPE: DNA
<213> ORGANISM: artificial sequence
<220> FEATURE:
<223> OTHER INFORMATION: synthetic construct

<400> SEQUENCE: 114
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 115
<211> LENGTH: 230
<212> TYPE: DNA
<213> ORGANISM: artificial sequence
<220> FEATURE:
<223> OTHER INFORMATION: synthetic construct

<400> SEQUENCE: 115
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 116
<211> LENGTH: 230
<212> TYPE: DNA
<213> ORGANISM: artificial sequence
<220> FEATURE:
<223> OTHER INFORMATION: synthetic construct

<400> SEQUENCE: 116
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 117
<211> LENGTH: 230
<212> TYPE: DNA
<213> ORGANISM: artificial sequence
<220> FEATURE:
<223> OTHER INFORMATION: synthetic construct

<400> SEQUENCE: 117
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 118
<211> LENGTH: 230
<212> TYPE: DNA
<213> ORGANISM: artificial sequence
<220> FEATURE:
<223> OTHER INFORMATION: synthetic construct

<400> SEQUENCE: 118
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 119
<211> LENGTH: 230
<212> TYPE: DNA
<213> ORGANISM: artificial sequence
<220> FEATURE:
<223> OTHER INFORMATION: synthetic construct

<400> SEQUENCE: 119
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 120
<211> LENGTH: 230
<212> TYPE: DNA
<213> ORGANISM: artificial sequence
<220> FEATURE:
<223> OTHER INFORMATION: synthetic construct

<400> SEQUENCE: 120
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 121
<211> LENGTH: 230
<212> TYPE: DNA
<213> ORGANISM: artificial sequence
<220> FEATURE:
<223> OTHER INFORMATION: synthetic construct

<400> SEQUENCE: 121
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 122
<211> LENGTH: 230
<212> TYPE: DNA
<213> ORGANISM: artificial sequence
<220> FEATURE:
<223> OTHER INFORMATION: synthetic construct

<400> SEQUENCE: 122
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 123
<211> LENGTH: 230
<212> TYPE: DNA
<213> ORGANISM: artificial sequence
<220> FEATURE:
<223> OTHER INFORMATION: synthetic construct

<400> SEQUENCE: 123
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 124
<211> LENGTH: 230
<212> TYPE: DNA
<213> ORGANISM: artificial sequence
<220> FEATURE:
<223> OTHER INFORMATION: synthetic construct

<400> SEQUENCE: 124
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 125
<211> LENGTH: 230
<212> TYPE: DNA
<213> ORGANISM: artificial sequence
<220> FEATURE:
<223> OTHER INFORMATION: synthetic construct

<400> SEQUENCE: 125
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 126
<211> LENGTH: 230
<212> TYPE: DNA
<213> ORGANISM: artificial sequence
<220> FEATURE:
<223> OTHER INFORMATION: synthetic construct

<400> SEQUENCE: 126
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 127
<211> LENGTH: 230
<212> TYPE: DNA
<213> ORGANISM: artificial sequence
<220> FEATURE:
<223> OTHER INFORMATION: synthetic construct

<400> SEQUENCE: 127
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 128
<211> LENGTH: 230
<212> TYPE: DNA
<213> ORGANISM: artificial sequence
<220> FEATURE:
<223> OTHER INFORMATION: synthetic construct

<400> SEQUENCE: 128
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 129
<211> LENGTH: 230
<212> TYPE: DNA
<213> ORGANISM: artificial sequence
<220> FEATURE:
<223> OTHER INFORMATION: synthetic construct

<400> SEQUENCE: 129
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 130
<211> LENGTH: 230
<212> TYPE: DNA
<213> ORGANISM: artificial sequence
<220> FEATURE:
<223> OTHER INFORMATION: synthetic construct

<400> SEQUENCE: 130
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 131
<211> LENGTH: 230
<212> TYPE: DNA
<213> ORGANISM: artificial sequence
<220> FEATURE:
<223> OTHER INFORMATION: synthetic construct

<400> SEQUENCE: 131
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 132
<211> LENGTH: 230

<212> TYPE: DNA
<213> ORGANISM: artificial sequence
<220> FEATURE:
<223> OTHER INFORMATION: synthetic construct

<400> SEQUENCE: 132
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 133
<211> LENGTH: 230
<212> TYPE: DNA
<213> ORGANISM: artificial sequence
<220> FEATURE:
<223> OTHER INFORMATION: synthetic construct

<400> SEQUENCE: 133
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 134
<211> LENGTH: 230
<212> TYPE: DNA
<213> ORGANISM: artificial sequence
<220> FEATURE:
<223> OTHER INFORMATION: synthetic construct

<400> SEQUENCE: 134
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 135
<211> LENGTH: 230
<212> TYPE: DNA
<213> ORGANISM: artificial sequence
<220> FEATURE:
<223> OTHER INFORMATION: synthetic construct

<400> SEQUENCE: 135
actatgcgat tgctttcctg gacccgtgca gctgcggtgg catgggaggc cggcaagcca 60
ctgtcgatcg aggaggtgga ggtagcgcct ccgcaggcca tggaggtgcg cgtcaagatc 120
ctcttcacct cgctctgcca caccgacgtc tacttctggg aggccaaggt atctaatcag 180
ccatcccatt tgtgatcttt gtcagtagat atgatacaac aactcgcggt 230

<210> SEQ ID NO 136
<211> LENGTH: 3079
<212> TYPE: DNA
<213> ORGANISM: artificial sequence
<220> FEATURE:
<223> OTHER INFORMATION: synthetic construct

<400> SEQUENCE: 136

-continued

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtggaat tctaaagatc taaaataaat    420
ggtaaaatgt caaatcaaaa ctaggctgca gtatgcagag cagagtcatg atgatactac    480
ttactacacc gattcttgtg tgcagaaaaa tatgttaaaa taattgaatc tttctctagc    540
caaatttgac aacaatgtac accgttcata ttgagagacg atgcttcttg tttgctttcg    600
gtggaagctg catatactca acattactcc ttcagcgagt tttccaactg agtcccacat    660
tgcccagacc taacacggta ttcttgttta taatgaaatg tgccaccaca tggattgaag    720
caagagacgt tctagggttt tagagctaga aatagcaagt taaaataagg ctagtccgtt    780
atcaacttga aaaagtggca ccgagtcggt gctttttttg gatccggcgc gccgcatgca    840
agcttggcgt aatcatggtc atagctgttt cctgtgtgaa attgttatcc gctcacaatt    900
ccacacaaca tacgagccgg aagcataaag tgtaaagcct ggggtgccta atgagtgagc    960
taactcacat taattgcgtt gcgctcactg cccgctttcc agtcgggaaa cctgtcgtgc   1020
cagctgcatt aatgaatcgg ccaacgcgcg gggagaggcg gtttgcgtat tgggcgctct   1080
tccgcttcct cgctcactga ctcgctgcgc tcggtcgttc ggctgcggcg agcggtatca   1140
gctcactcaa aggcggtaat acggttatcc acagaatcag gggataacgc aggaaagaac   1200
atgtgagcaa aaggccagca aaaggccagg aaccgtaaaa aggccgcgtt gctggcgttt   1260
ttccataggc tccgcccccc tgacgagcat cacaaaaatc gacgctcaag tcagaggtgg   1320
cgaaacccga caggactata aagataccag gcgtttcccc ctggaagctc cctcgtgcgc   1380
tctcctgttc cgaccctgcc gcttaccgga tacctgtccg cctttctccc ttcgggaagc   1440
gtggcgcttt ctcatagctc acgctgtagg tatctcagtt cggtgtaggt cgttcgctcc   1500
aagctgggct gtgtgcacga accccccgtt cagcccgacc gctgcgcctt atccggtaac   1560
tatcgtcttg agtccaaccc ggtaagacac gacttatcgc cactggcagc agccactggt   1620
aacaggatta gcagagcgag gtatgtaggc ggtgctacag agttcttgaa gtggtggcct   1680
aactacggct acactagaag aacagtattt ggtatctgcg ctctgctgaa gccagttacc   1740
ttcggaaaaa gagttggtag ctcttgatcc ggcaaacaaa ccaccgctgg tagcggtggt   1800
tttttgtttg caagcagcag attacgcgcag agaaaaaaag gatctcaaga agatcctttg   1860
atcttttcta cggggtctga cgctcagtgg aacgaaaact cacgttaagg gattttggtc   1920
atgagattat caaaaaggat cttcacctag atccttttaa attaaaaatg aagttttaaa   1980
tcaatctaaa gtatatatga gtaaacttgg tctgacagtt accaatgctt aatcagtgag   2040
gcacctatct cagcgatctg tctatttcgt tcatccatag ttgcctgact ccccgtcgtg   2100
tagataacta cgatacggga gggcttacca tctggcccca gtgctgcaat gataccgcga   2160
gacccacgct caccggctcc agatttatca gcaataaacc agccagccgg aagggccgag   2220
cgcagaagtg gtcctgcaac tttatccgcc tccatccagt ctattaattg ttgccgggaa   2280
gctagagtaa gtagttcgcc agttaatagt ttgcgcaacg ttgttgccat tgctacaggc   2340
atcgtggtgt cacgctcgtc gtttggtatg gcttcattca gctccggttc ccaacgatca   2400
```

aggcgagtta catgatcccc catgttgtgc aaaaaagcgg ttagctcctt cggtcctccg 2460
atcgttgtca gaagtaagtt ggccgcagtg ttatcactca tggttatggc agcactgcat 2520
aattctctta ctgtcatgcc atccgtaaga tgcttttctg tgactggtga gtactcaacc 2580
aagtcattct gagaatagtg tatgcggcga ccgagttgct cttgcccggc gtcaatacgg 2640
gataataccg cgccacatag cagaacttta aaagtgctca tcattggaaa acgttcttcg 2700
gggcgaaaac tctcaaggat cttaccgctg ttgagatcca gttcgatgta acccactcgt 2760
gcacccaact gatcttcagc atcttttact ttcaccagcg tttctgggtg agcaaaaaca 2820
ggaaggcaaa atgccgcaaa aaagggaata agggcgacac ggaaatgttg aatactcata 2880
ctcttccttt ttcaatatta ttgaagcatt tatcagggtt attgtctcat gagcggatac 2940
atatttgaat gtatttagaa aaataaacaa ataggggttc cgcgcacatt tccccgaaaa 3000
gtgccacctg acgtctaaga aaccattatt atcatgacat taacctataa aaataggcgt 3060
atcacgaggc cctttcgtc 3079

<210> SEQ ID NO 137
<211> LENGTH: 20
<212> TYPE: DNA
<213> ORGANISM: artificial sequence
<220> FEATURE:
<223> OTHER INFORMATION: synthetic construct

<400> SEQUENCE: 137
gaagcaagag acgttctagg 20

<210> SEQ ID NO 138
<211> LENGTH: 76
<212> TYPE: DNA
<213> ORGANISM: artificial sequence
<220> FEATURE:
<223> OTHER INFORMATION: synthetic construct

<400> SEQUENCE: 138
gttttagagc tagaaatagc aagttaaaat aaggctagtc cgttatcaac ttgaaaaagt 60
ggcaccgagt cggtgc 76

<210> SEQ ID NO 139
<211> LENGTH: 96
<212> TYPE: DNA
<213> ORGANISM: artificial sequence
<220> FEATURE:
<223> OTHER INFORMATION: synthetic construct

<400> SEQUENCE: 139
gaagcaagag acgttctagg gttttagagc tagaaatagc aagttaaaat aaggctagtc 60
cgttatcaac ttgaaaaagt ggcaccgagt cggtgc 96

<210> SEQ ID NO 140
<211> LENGTH: 8569
<212> TYPE: DNA
<213> ORGANISM: artificial sequence
<220> FEATURE:
<223> OTHER INFORMATION: synthetic construct

<400> SEQUENCE: 140
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120

-continued

```
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt ctaaagatct ggcgcgccgg    420
cccgggctgg ttattgtttt tgtcaatgag ctatctttta gtcttatgtt attggtgaat    480
ctgtccttaa gttgcatcat ttaacacatc tcctcattag agaaaaaaat tcttccctaa    540
acgattggta gtaaaaacat ctaataagaa ataagaaaga aaaattagga aaaaggaaag    600
ttcattaaaa aaaatatttt gaattatttt ttaaaaaata tctaaatatt ttttaaatga    660
ataattttat ataaactgta actaaatgta tacaagtaat gtatgttaaa aaaatacttg    720
aaaaatctac tgaaaatata tcttacaagg tgaaattaaa taagaaagaa tttagtggaa    780
taattatgat tttatttaaa aaataattat taaagatttt tttgctccat aataagaaaa    840
cttttcaatt attcttttct ggtccataat aaaaaaaatc tagcatgaca gcttttccat    900
agatttttaa taatgtaaaa gcagccgact tcaggcaatg gatagtgggg cccgtatcaa    960
cttcggacgc tccacttgca acggggtggg cccaatataa caacgacgtc gtaacagata   1020
aagcgaagat tgaaggtgca tgtgactccg tcaagattac gaaaccgcca actaccacgc   1080
aaattgcaat tctcaatttc ctagaaggac tctccgaaaa tgcatccaat accaaatatt   1140
acccgtgtca taggcaccaa gtgacaccat acatgaacac gcgtcacaat atgactggag   1200
aagggttcca caccttatgc tataaaacgc cccacacccc tcctccttcc ttcgcagttc   1260
aattccaata tattccattc tctctgtgta tttccctacc tctcccttca aggttagtcg   1320
atttcttctg tttttcttct tcgttctttc catgaattgt gtatgttctt tgatcaatac   1380
gatgttgatt tgattgtgtt ttgtttggtt tcatcgatct tcaattttca taatcagatt   1440
cagcttttat tatctttaca acaacgtcct taatttgatg attctttaat cgtagatttg   1500
ctctaattag agctttttca tgtcagatcc ctttacaaca agccttaatt gttgattcat   1560
taatcgtaga ttagggcttt tttcattgat tacttcagat ccgttaaacg taaccataga   1620
tcagggcttt ttcatgaatt acttcagatc cgttaaacaa cagccttatt ttttatactt   1680
ctgtggtttt tcaagaaatt gttcagatcc gttgacaaaa agccttattc gttgattcta   1740
tatcgttttt cgagagatat tgctcagatg tgttagcaac tgccttgttt gttgattcta   1800
ttgccgtgga ttagggtttt ttttcacgag attgcttcag atccgtactt aagattacgt   1860
aatggatttt gattctgatt tatctgtgat tgttgactcg acaggatcgg taccccatgg   1920
ataagaagta ctctatcgga ctcgatatcg gaactaactc tgtgggatgg gctgtgatca   1980
ccgatgagta caaggtgcca tctaagaagt tcaaggttct cggaaacacc gataggcact   2040
ctatcaagaa aaaccttatc ggtgctctcc tcttcgattc tggtgaaact gctgaggcta   2100
ccagactcaa gagaaccgct agaagaaggt acaccagaag aaagaacagg atctgctacc   2160
tccaagagat cttctctaac gagatggcta aagtggatga ttcattcttc cacaggctcg   2220
aagagtcatt cctcgtggaa gaagataaga agcacgagag gcaccctatc ttcggaaaca   2280
tcgttgatga ggtggcatac cacgagaagt accctactat ctaccacctc agaaagaagc   2340
tcgttgattc tactgataag gctgatctca ggctcatcta cctcgctctc gctcacatga   2400
tcaagttcag aggacacttc ctcatcgagg gtgatctcaa ccctgataac tctgatgtgg   2460
ataagttgtt catccagctc gtgcagacct acaaccagct tttcgaagag aaccctatca   2520
```

acgcttcagg tgtggatgct aaggctatcc tctctgctag gctctctaag tcaagaaggc 2580
ttgagaacct cattgctcag ctccctggtg agaagaagaa cggacttttc ggaaacttga 2640
tcgctctctc tctcggactc acccctaact tcaagtctaa cttcgatctc gctgaggatg 2700
caaagctcca gctctcaaag gatacctacg atgatgatct cgataacctc ctcgctcaga 2760
tcggagatca gtacgctgat ttgttcctcg ctgctaagaa cctctctgat gctatcctcc 2820
tcagtgatat cctcagagtg aacaccgaga tcaccaaggc tccactctca gcttctatga 2880
tcaagagata cgatgagcac caccaggatc tcacacttct caaggctctt gttagacagc 2940
agctcccaga gaagtacaaa gagattttct tcgatcagtc taagaacgga tacgctggtt 3000
acatcgatgg tggtgcatct caagaagagt tctacaagtt catcaagcct atcctcgaga 3060
agatggatgg aaccgaggaa ctcctcgtga agctcaatag agaggatctt ctcagaaagc 3120
agaggacctt cgataacgga tctatccctc atcagatcca cctcggagag ttgcacgcta 3180
tccttagaag gcaagaggat ttctacccat tcctcaagga taacagggaa aagattgaga 3240
agattctcac cttcagaatc ccttactacg tgggacctct cgctagagga aactcaagat 3300
tcgcttggat gaccagaaag tctgaggaaa ccatcacccc ttggaacttc gaagaggtgg 3360
tggataaggg tgctagtgct cagtctttca tcgagaggat gaccaacttc gataagaacc 3420
ttccaaacga gaaggtgctc cctaagcact ctttgctcta cgagtacttc accgtgtaca 3480
acgagttgac caaggttaag tacgtgaccg agggaatgag gaagcctgct tttttgtcag 3540
gtgagcaaaa gaaggctatc gttgatctct tgttcaagac caacagaaag gtgaccgtga 3600
agcagctcaa agaggattac ttcaagaaaa tcgagtgctt cgattcagtt gagatttctg 3660
gtgttgagga taggttcaac gcatctctcg gaacctacca cgatctcctc aagatcatta 3720
aggataagga tttcttggat aacgaggaaa acgaggatat cttggaggat atcgttctta 3780
ccctcaccct ctttgaagat agagagatga ttgaagaaag gctcaagacc tacgctcatc 3840
tcttcgatga taaggtgatg aagcagttga agagaagaag atacactggt tggggaaggc 3900
tctcaagaaa gctcattaac ggaatcaggg ataagcagtc tggaaagaca atccttgatt 3960
tcctcaagtc tgatggattc gctaacagaa acttcatgca gctcatccac gatgattctc 4020
tcacctttaa agaggatatc cagaaggctc aggtttcagg acagggtgat agtctccatg 4080
agcatatcgc taacctcgct ggatctcctg caatcaagaa gggaatcctc cagactgtga 4140
aggttgtgga tgagttggtg aaggtgatgg gaaggcataa gcctgagaac atcgtgatcg 4200
aaatggctag agagaaccag accactcaga agggacagaa gaactctagg gaaaggatga 4260
agaggatcga ggaaggtatc aaagagcttg gatctcagat cctcaaagag caccctgttg 4320
agaacactca gctccagaat gagaagctct acctctacta cctccagaac ggaagggata 4380
tgtatgtgga tcaagagttg gatatcaaca ggctctctga ttacgatgtt gatcatatcg 4440
tgccacagtc attcttgaag gatgattcta tcgataacaa ggtgctcacc aggtctgata 4500
agaacagggg taagagtgat aacgtgccaa gtgaagaggt tgtgaagaaa atgaagaact 4560
attggaggca gctcctcaac gctaagctca tcactcagag aaagttcgat aacttgacta 4620
aggctgagag gggaggactc tctgaattgg ataaggcagg attcatcaag aggcagcttg 4680
tggaaaccag gcagatcact aagcacgttg cacagatcct cgattctagg atgaacacca 4740
agtacgatga gaacgataag ttgatcaggg aagtgaaggt tatcaccctc aagtcaaagc 4800
tcgtgtctga tttcagaaag gatttccaat tctacaaggt gagggaaatc aacaactacc 4860

```
accacgctca cgatgcttac cttaacgctg ttgttggaac cgctctcatc aagaagtatc   4920
ctaagctcga gtcagagttc gtgtacggtg attacaaggt gtacgatgtg aggaagatga   4980
tcgctaagtc tgagcaagag atcggaaagg ctaccgctaa gtatttcttc tactctaaca   5040
tcatgaattt cttcaagacc gagattaccc tcgctaacgg tgagatcaga aagaggccac   5100
tcatcgagac aaacggtgaa acaggtgaga tcgtgtggga taagggaagg gatttcgcta   5160
ccgttagaaa ggtgctctct atgccacagg tgaacatcgt taagaaaacc gaggtgcaga   5220
ccggtggatt ctctaaagag tctatcctcc ctaagaggaa ctctgataag ctcattgcta   5280
ggaagaagga ttgggaccct aagaaatacg gtggtttcga ttctcctacc gtggcttact   5340
ctgttctcgt tgtggctaag gttgagaagg gaaagagtaa gaagctcaag tctgttaagg   5400
aacttctcgg aatcactatc atggaaaggt catctttcga gaagaaccca atcgatttcc   5460
tcgaggctaa gggatacaaa gaggttaaga aggatctcat catcaagctc ccaaagtact   5520
cactcttcga actcgagaac ggtagaaaga ggatgctcgc ttctgctggt gagcttcaaa   5580
agggaaacga gcttgctctc ccatctaagt acgttaactt tctttacctc gcttctcact   5640
acgagaagtt gaagggatct ccagaagata acgagcagaa gcaacttttc gttgagcagc   5700
acaagcacta cttggatgag atcatcgagc agatctctga gttctctaaa agggtgatcc   5760
tcgctgatgc aaacctcgat aaggtgttgt ctgcttacaa caagcacaga gataagccta   5820
tcagggaaca ggcagagaac atcatccatc tcttcaccct taccaacctc ggtgctcctg   5880
ctgctttcaa gtacttcgat acaaccatcg ataggaagag atacacctct accaaagaag   5940
tgctcgatgc taccctcatc catcagtcta tcactggact ctacgagact aggatcgatc   6000
tctcacagct cggtggtgat tcaagggctg atcctaagaa gaagaggaag gtttgagcgg   6060
ccgcgatcgt tcaaacattt ggcaataaag tttcttaaga ttgaatcctg ttgccggtct   6120
tgcgatgatt atcatataat ttctgttgaa ttacgttaag catgtaataa ttaacatgta   6180
atgcatgacg ttatttatga gatgggtttt tatgattaga gtcccgcaat tatacattta   6240
atacgcgata gaaaacaaaa tatagcgcgc aaactaggat aaattatcgc gcgcggtgtc   6300
atctatgtta ctagatcgga tccgcatgca agcttggcgt aatcatggtc atagctgttt   6360
cctgtgtgaa attgttatcc gctcacaatt ccacacaaca tacgagccgg aagcataaag   6420
tgtaaagcct ggggtgccta atgagtgagc taactcacat taattgcgtt gcgctcactg   6480
cccgctttcc agtcgggaaa cctgtcgtgc cagctgcatt aatgaatcgg ccaacgcgcg   6540
gggagaggcg gtttgcgtat tgggcgctct tccgcttcct cgctcactga ctcgctgcgc   6600
tcggtcgttc ggctgcggcg agcggtatca gctcactcaa aggcggtaat acggttatcc   6660
acagaatcag gggataacgc aggaaagaac atgtgagcaa aaggccagca aaaggccagg   6720
aaccgtaaaa aggccgcgtt gctggcgttt ttccataggc tccgcccccc tgacgagcat   6780
cacaaaaatc gacgctcaag tcagaggtgg cgaaacccga caggactata aagataccag   6840
gcgtttcccc ctggaagctc cctcgtgcgc tctcctgttc cgaccctgcc gcttaccgga   6900
tacctgtccg cctttctccc ttcgggaagc gtggcgcttt ctcatagctc acgctgtagg   6960
tatctcagtt cggtgtaggt cgttcgctcc aagctgggct gtgtgcacga accccccgtt   7020
cagcccgacc gctgcgcctt atccggtaac tatcgtcttg agtccaaccc ggtaagacac   7080
gacttatcgc cactggcagc agccactggt aacaggatta gcagagcgag gtatgtaggc   7140
ggtgctacag agttcttgaa gtggtggcct aactacggct acactagaag aacagtattt   7200
ggtatctgcg ctctgctgaa gccagttacc ttcggaaaaa gagttggtag ctcttgatcc   7260
```

```
ggcaaacaaa ccaccgctgg tagcggtggt ttttttgttt gcaagcagca gattacgcgc   7320

agaaaaaaag gatctcaaga agatcctttg atcttttcta cggggtctga cgctcagtgg   7380

aacgaaaact cacgttaagg gattttggtc atgagattat caaaaaggat cttcacctag   7440

atccttttaa attaaaaatg aagttttaaa tcaatctaaa gtatatatga gtaaacttgg   7500

tctgacagtt accaatgctt aatcagtgag gcacctatct cagcgatctg tctatttcgt   7560

tcatccatag ttgcctgact ccccgtcgtg tagataacta cgatacggga gggcttacca   7620

tctggcccca gtgctgcaat gataccgcga gacccacgct caccggctcc agatttatca   7680

gcaataaacc agccagccgg aagggccgag cgcagaagtg gtcctgcaac tttatccgcc   7740

tccatccagt ctattaattg ttgccgggaa gctagagtaa gtagttcgcc agttaatagt   7800

ttgcgcaacg ttgttgccat tgctacaggc atcgtggtgt cacgctcgtc gtttggtatg   7860

gcttcattca gctccggttc ccaacgatca aggcgagtta catgatcccc catgttgtgc   7920

aaaaaagcgg ttagctcctt cggtcctccg atcgttgtca gaagtaagtt ggccgcagtg   7980

ttatcactca tggttatggc agcactgcat aattctctta ctgtcatgcc atccgtaaga   8040

tgcttttctg tgactggtga gtactcaacc aagtcattct gagaatagtg tatgcggcga   8100

ccgagttgct cttgcccggc gtcaatacgg gataataccg cgccacatag cagaacttta   8160

aaagtgctca tcattggaaa acgttcttcg gggcgaaaac tctcaaggat cttaccgctg   8220

ttgagatcca gttcgatgta acccactcgt gcacccaact gatcttcagc atcttttact   8280

ttcaccagcg tttctgggtg agcaaaaaca ggaaggcaaa atgccgcaaa aaagggaata   8340

agggcgacac ggaaatgttg aatactcata ctcttccttt ttcaatatta ttgaagcatt   8400

tatcagggtt attgtctcat gagcggatac atatttgaat gtatttagaa aaataaacaa   8460

ataggggttc cgcgcacatt tccccgaaaa gtgccacctg acgtctaaga aaccattatt   8520

atcatgacat taacctataa aaataggcgt atcacgaggc cctttcgtc              8569
```

<210> SEQ ID NO 141
<211> LENGTH: 4104
<212> TYPE: DNA
<213> ORGANISM: artificial sequence
<220> FEATURE:
<223> OTHER INFORMATION: synthetic construct

<400> SEQUENCE: 141

```
atggataaga agtactctat cggactcgat atcggaacta actctgtggg atgggctgtg     60

atcaccgatg agtacaaggt gccatctaag aagttcaagg ttctcggaaa caccgatagg    120

cactctatca agaaaaacct tatcggtgct ctcctcttcg attctggtga aactgctgag    180

gctaccagac tcaagagaac cgctagaaga aggtacacca gaagaaagaa caggatctgc    240

tacctccaag agatcttctc taacgagatg gctaaagtgg atgattcatt cttccacagg    300

ctcgaagagt cattcctcgt ggaagaagat aagaagcacg agaggcaccc tatcttcgga    360

aacatcgttg atgaggtggc ataccacgag aagtacccta ctatctacca cctcagaaag    420

aagctcgttg attctactga taaggctgat ctcaggctca tctacctcgc tctcgctcac    480

atgatcaagt tcagaggaca cttcctcatc gagggtgatc tcaaccctga taactctgat    540

gtggataagt tgttcatcca gctcgtgcag acctacaacc agcttttcga agagaaccct    600

atcaacgctt caggtgtgga tgctaaggct atcctctctg ctaggctctc taagtcaaga    660

aggcttgaga acctcattgc tcagctccct ggtgagaaga agaacggact tttcggaaac    720
```

```
ttgatcgctc tctctctcgg actcacccct aacttcaagt ctaacttcga tctcgctgag    780
gatgcaaagc tccagctctc aaaggatacc tacgatgatg atctcgataa cctcctcgct    840
cagatcggag atcagtacgc tgatttgttc ctcgctgcta agaacctctc tgatgctatc    900
ctcctcagtg atatcctcag agtgaacacc gagatcacca aggctccact ctcagcttct    960
atgatcaaga gatacgatga gcaccaccag gatctcacac ttctcaaggc tcttgttaga   1020
cagcagctcc cagagaagta caaagagatt ttcttcgatc agtctaagaa cggatacgct   1080
ggttacatcg atggtggtgc atctcaagaa gagttctaca agttcatcaa gcctatcctc   1140
gagaagatgg atggaaccga ggaactcctc gtgaagctca atagagagga tcttctcaga   1200
aagcagagga ccttcgataa cggatctatc cctcatcaga tccacctcgg agagttgcac   1260
gctatcctta gaaggcaaga ggatttctac ccattcctca aggataacag ggaaaagatt   1320
gagaagattc tcaccttcag aatcccttac tacgtgggac ctctcgctag aggaaactca   1380
agattcgctt ggatgaccag aaagtctgag gaaaccatca ccccttggaa cttcgaagag   1440
gtggtggata agggtgctag tgctcagtct ttcatcgaga ggatgaccaa cttcgataag   1500
aaccttccaa acgagaaggt gctccctaag cactctttgc tctacgagta cttcaccgtg   1560
tacaacgagt tgaccaaggt taagtacgtg accgagggaa tgaggaagcc tgctttttg    1620
tcaggtgagc aaaagaaggc tatcgttgat ctcttgttca agaccaacag aaaggtgacc   1680
gtgaagcagc tcaaagagga ttacttcaag aaaatcgagt gcttcgattc agttgagatt   1740
tctggtgttg aggataggtt caacgcatct ctcggaacct accacgatct cctcaagatc   1800
attaaggata aggatttctt ggataacgag gaaaacgagg atatcttgga ggatatcgtt   1860
cttaccctca ccctctttga agatagagag atgattgaag aaaggctcaa gacctacgct   1920
catctcttcg atgataaggt gatgaagcag ttgaagagaa gaagatacac tggttgggga   1980
aggctctcaa gaaagctcat taacggaatc agggataagc agtctggaaa gacaatcctt   2040
gatttcctca agtctgatgg attcgctaac agaaacttca tgcagctcat ccacgatgat   2100
tctctcacct ttaaagagga tatccagaag gctcaggttt caggacaggg tgatagtctc   2160
catgagcata tcgctaacct cgctggatct cctgcaatca agaagggaat cctccagact   2220
gtgaaggttg tggatgagtt ggtgaaggtg atgggaaggc ataagcctga gaacatcgtg   2280
atcgaaatgg ctagagagaa ccagaccact cagaagggac agaagaactc tagggaaagg   2340
atgaagagga tcgaggaagg tatcaaagag cttggatctc agatcctcaa agagcaccct   2400
gttgagaaca ctcagctcca gaatgagaag ctctacctct actacctcca gaacggaagg   2460
gatatgtatg tggatcaaga gttggatatc aacaggctct ctgattacga tgttgatcat   2520
atcgtgccac agtcattctt gaaggatgat tctatcgata acaaggtgct caccaggtct   2580
gataagaaca ggggtaagag tgataacgtg ccaagtgaag aggttgtgaa gaaaatgaag   2640
aactattgga ggcagctcct caacgctaag ctcatcactc agagaaagtt cgataacttg   2700
actaaggctg agaggggagg actctctgaa ttggataagg caggattcat caagaggcag   2760
cttgtggaaa ccaggcagat cactaagcac gttgcacaga tcctcgattc taggatgaac   2820
accaagtacg atgagaacga taagttgatc agggaagtga aggttatcac cctcaagtca   2880
aagctcgtgt ctgatttcag aaaggatttc caattctaca aggtgaggga aatcaacaac   2940
taccaccacg ctcacgatgc ttaccttaac gctgttgttg gaaccgctct catcaagaag   3000
tatcctaagc tcgagtcaga gttcgtgtac ggtgattaca aggtgtacga tgtgaggaag   3060
atgatcgcta agtctgagca agagatcgga aaggctaccg ctaagtattt cttctactct   3120
```

```
aacatcatga atttcttcaa gaccgagatt accctcgcta acggtgagat cagaaagagg   3180

ccactcatcg agacaaacgg tgaaacaggt gagatcgtgt gggataaggg aagggatttc   3240

gctaccgtta gaaaggtgct ctctatgcca caggtgaaca tcgttaagaa aaccgaggtg   3300

cagaccggtg gattctctaa agagtctatc ctccctaaga ggaactctga taagctcatt   3360

gctaggaaga aggattggga ccctaagaaa tacggtggtt tcgattctcc taccgtggct   3420

tactctgttc tcgttgtggc taaggttgag aagggaaaga gtaagaagct caagtctgtt   3480

aaggaacttc tcggaatcac tatcatggaa aggtcatctt tcgagaagaa cccaatcgat   3540

ttcctcgagg ctaagggata caaagaggtt aagaaggatc tcatcatcaa gctcccaaag   3600

tactcactct tcgaactcga gaacggtaga aagaggatgc tcgcttctgc tggtgagctt   3660

caaaagggaa acgagcttgc tctcccatct aagtacgtta actttcttta cctcgcttct   3720

cactacgaga agttgaaggg atctccagaa gataacgagc agaagcaact tttcgttgag   3780

cagcacaagc actacttgga tgagatcatc gagcagatct ctgagttctc taaaagggtg   3840

atcctcgctg atgcaaacct cgataaggtg ttgtctgctt acaacaagca cagagataag   3900

cctatcaggg aacaggcaga gaacatcatc catctcttca cccttaccaa cctcggtgct   3960

cctgctgctt tcaagtactt cgatacaacc atcgatagga agagatacac ctctaccaaa   4020

gaagtgctcg atgctaccct catccatcag tctatcactg gactctacga gactaggatc   4080

gatctctcac agctcggtgg tgat                                          4104
```

<210> SEQ ID NO 142
<211> LENGTH: 1368
<212> TYPE: PRT
<213> ORGANISM: Streptococcus pyogenes

<400> SEQUENCE: 142

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190
```

```
Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
```

```
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035
```

```
Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 143
<211> LENGTH: 21
<212> TYPE: DNA
<213> ORGANISM: artificial sequence
<220> FEATURE:
<223> OTHER INFORMATION: synthetic construct

<400> SEQUENCE: 143
cctaagaaga agaggaaggt t                                              21

<210> SEQ ID NO 144
<211> LENGTH: 7
<212> TYPE: PRT
<213> ORGANISM: artificial sequence
<220> FEATURE:
<223> OTHER INFORMATION: synthetic construct

<400> SEQUENCE: 144

Pro Lys Lys Lys Arg Lys Val
1               5

<210> SEQ ID NO 145
<211> LENGTH: 4137
<212> TYPE: DNA
<213> ORGANISM: artificial sequence
<220> FEATURE:
<223> OTHER INFORMATION: synthetic construct

<400> SEQUENCE: 145
atggataaga agtactctat cggactcgat atcggaacta actctgtggg atgggctgtg 60
atcaccgatg agtacaaggt gccatctaag aagttcaagg ttctcggaaa caccgatagg 120
cactctatca agaaaaacct tatcggtgct ctcctcttcg attctggtga aactgctgag 180
gctaccagac tcaagagaac cgctagaaga aggtacacca gaagaaagaa caggatctgc 240
tacctccaag agatcttctc taacgagatg gctaaagtgg atgattcatt cttccacagg 300
ctcgaagagt cattcctcgt ggaagaagat aagaagcacg agaggcaccc tatcttcgga 360
aacatcgttg atgaggtggc ataccacgag aagtacccta ctatctacca cctcagaaag 420
aagctcgttg attctactga taaggctgat ctcaggctca tctacctcgc tctcgctcac 480
atgatcaagt tcagaggaca cttcctcatc gagggtgatc tcaaccctga taactctgat 540
gtggataagt tgttcatcca gctcgtgcag acctacaacc agcttttcga agagaaccct 600
atcaacgctt caggtgtgga tgctaaggct atcctctctg ctaggctctc taagtcaaga 660
aggcttgaga acctcattgc tcagctccct ggtgagaaga agaacggact tttcggaaac 720
ttgatcgctc tctctctcgg actcacccct aacttcaagt ctaacttcga tctcgctgag 780
gatgcaaagc tccagctctc aaaggatacc tacgatgatg atctcgataa cctcctcgct 840
cagatcggag atcagtacgc tgatttgttc ctcgctgcta agaacctctc tgatgctatc 900
ctcctcagtg atatcctcag agtgaacacc gagatcacca aggctccact ctcagcttct 960
atgatcaaga gatacgatga gcaccaccag gatctcacac ttctcaaggc tcttgttaga 1020
cagcagctcc cagagaagta caaagagatt ttcttcgatc agtctaagaa cggatacgct 1080
ggttacatcg atggtggtgc atctcaagaa gagttctaca agttcatcaa gcctatcctc 1140
gagaagatgg atggaaccga ggaactcctc gtgaagctca atagagagga tcttctcaga 1200
aagcagagga ccttcgataa cggatctatc cctcatcaga tccacctcgg agagttgcac 1260
gctatcctta gaaggcaaga ggatttctac ccattcctca aggataacag ggaaaagatt 1320
gagaagattc tcaccttcag aatcccttac tacgtgggac ctctcgctag aggaaactca 1380
agattcgctt ggatgaccag aaagtctgag gaaaccatca ccccttggaa cttcgaagag 1440
gtggtggata agggtgctag tgctcagtct ttcatcgaga ggatgaccaa cttcgataag 1500
aaccttccaa acgagaaggt gctccctaag cactctttgc tctacgagta cttcaccgtg 1560
tacaacgagt tgaccaaggt taagtacgtg accgagggaa tgaggaagcc tgctttttttg 1620
tcaggtgagc aaaagaaggc tatcgttgat ctcttgttca agaccaacag aaaggtgacc 1680

-continued

```
gtgaagcagc tcaaagagga ttacttcaag aaaatcgagt gcttcgattc agttgagatt   1740
tctggtgttg aggataggtt caacgcatct ctcggaacct accacgatct cctcaagatc   1800
attaaggata aggatttctt ggataacgag gaaaacgagg atatcttgga ggatatcgtt   1860
cttaccctca ccctctttga agatagagag atgattgaag aaaggctcaa gacctacgct   1920
catctcttcg atgataaggt gatgaagcag ttgaagagaa gaagatacac tggttgggga   1980
aggctctcaa gaaagctcat taacggaatc agggataagc agtctggaaa gacaatcctt   2040
gatttcctca agtctgatgg attcgctaac agaaacttca tgcagctcat ccacgatgat   2100
tctctcacct ttaaagagga tatccagaag gctcaggttt caggacaggg tgatagtctc   2160
catgagcata tcgctaacct cgctggatct cctgcaatca agaagggaat cctccagact   2220
gtgaaggttg tggatgagtt ggtgaaggtg atgggaaggc ataagcctga gaacatcgtg   2280
atcgaaatgg ctagagagaa ccagaccact cagaagggac agaagaactc tagggaaagg   2340
atgaagagga tcgaggaagg tatcaaagag cttggatctc agatcctcaa agagcaccct   2400
gttgagaaca ctcagctcca gaatgagaag ctctacctct actacctcca gaacggaagg   2460
gatatgtatg tggatcaaga gttggatatc aacaggctct ctgattacga tgttgatcat   2520
atcgtgccac agtcattctt gaaggatgat tctatcgata acaaggtgct caccaggtct   2580
gataagaaca ggggtaagag tgataacgtg ccaagtgaag aggttgtgaa gaaaatgaag   2640
aactattgga ggcagctcct caacgctaag ctcatcactc agagaaagtt cgataacttg   2700
actaaggctg agaggggagg actctctgaa ttggataagg caggattcat caagaggcag   2760
cttgtggaaa ccaggcagat cactaagcac gttgcacaga tcctcgattc taggatgaac   2820
accaagtacg atgagaacga taagttgatc agggaagtga aggttatcac cctcaagtca   2880
aagctcgtgt ctgatttcag aaaggatttc caattctaca aggtgaggga aatcaacaac   2940
taccaccacg ctcacgatgc ttaccttaac gctgttgttg gaaccgctct catcaagaag   3000
tatcctaagc tcgagtcaga gttcgtgtac ggtgattaca aggtgtacga tgtgaggaag   3060
atgatcgcta agtctgagca agagatcgga aaggctaccg ctaagtattt cttctactct   3120
aacatcatga atttcttcaa gaccgagatt accctcgcta acggtgagat cagaaagagg   3180
ccactcatcg agacaaacgg tgaaacaggt gagatcgtgt gggataaggg aagggatttc   3240
gctaccgtta gaaaggtgct ctctatgcca caggtgaaca tcgttaagaa aaccgaggtg   3300
cagaccggtg gattctctaa agagtctatc ctccctaaga ggaactctga taagctcatt   3360
gctaggaaga aggattggga ccctaagaaa tacggtggtt tcgattctcc taccgtggct   3420
tactctgttc tcgttgtggc taaggttgag aagggaaaga gtaagaagct caagtctgtt   3480
aaggaacttc tcggaatcac tatcatggaa aggtcatctt tcgagaagaa cccaatcgat   3540
ttcctcgagg ctaagggata caaagaggtt aagaaggatc tcatcatcaa gctcccaaag   3600
tactcactct tcgaactcga gaacggtaga aagaggatgc tcgcttctgc tggtgagctt   3660
caaaagggaa acgagcttgc tctcccatct aagtacgtta actttcttta cctcgcttct   3720
cactacgaga agttgaaggg atctccagaa gataacgagc agaagcaact tttcgttgag   3780
cagcacaagc actacttgga tgagatcatc gagcagatct ctgagttctc taaaagggtg   3840
atcctcgctg atgcaaacct cgataaggtg ttgtctgctt acaacaagca cagagataag   3900
cctatcaggg aacaggcaga gaacatcatc catctcttca cccttaccaa cctcggtgct   3960
cctgctgctt tcaagtactt cgatacaacc atcgatagga agagatacac ctctaccaaa   4020
gaagtgctcg atgctaccct catccatcag tctatcactg gactctacga gactaggatc   4080
```

gatctctcac agctcggtgg tgattcaagg gctgatccta agaagaagag gaaggtt 4137

<210> SEQ ID NO 146
<211> LENGTH: 1379
<212> TYPE: PRT
<213> ORGANISM: artificial sequence
<220> FEATURE:
<223> OTHER INFORMATION: synthetic construct

<400> SEQUENCE: 146

Met Asp Lys Lys Tyr Ser Ile Gly Leu Asp Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

Met Ile Lys Phe Arg Gly His Phe Leu Ile Glu Gly Asp Leu Asn Pro
165 170 175

Asp Asn Ser Asp Val Asp Lys Leu Phe Ile Gln Leu Val Gln Thr Tyr
180 185 190

Asn Gln Leu Phe Glu Glu Asn Pro Ile Asn Ala Ser Gly Val Asp Ala
195 200 205

Lys Ala Ile Leu Ser Ala Arg Leu Ser Lys Ser Arg Arg Leu Glu Asn
210 215 220

Leu Ile Ala Gln Leu Pro Gly Glu Lys Lys Asn Gly Leu Phe Gly Asn
225 230 235 240

Leu Ile Ala Leu Ser Leu Gly Leu Thr Pro Asn Phe Lys Ser Asn Phe
245 250 255

Asp Leu Ala Glu Asp Ala Lys Leu Gln Leu Ser Lys Asp Thr Tyr Asp
260 265 270

Asp Asp Leu Asp Asn Leu Leu Ala Gln Ile Gly Asp Gln Tyr Ala Asp
275 280 285

Leu Phe Leu Ala Ala Lys Asn Leu Ser Asp Ala Ile Leu Leu Ser Asp
290 295 300

Ile Leu Arg Val Asn Thr Glu Ile Thr Lys Ala Pro Leu Ser Ala Ser
305 310 315 320

Met Ile Lys Arg Tyr Asp Glu His His Gln Asp Leu Thr Leu Leu Lys
325 330 335

Ala Leu Val Arg Gln Gln Leu Pro Glu Lys Tyr Lys Glu Ile Phe Phe
340 345 350

-continued

```
Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
```

-continued

```
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185
```

```
Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Ser Arg Ala Asp Pro Lys Lys Lys Arg Lys Val
    1370                1375
```

<210> SEQ ID NO 147
<211> LENGTH: 13
<212> TYPE: PRT
<213> ORGANISM: artificial sequence
<220> FEATURE:
<223> OTHER INFORMATION: synthetic construct

<400> SEQUENCE: 147

```
Gly Arg Lys Lys Arg Arg Gln Arg Arg Arg Pro Pro Gln
1               5                   10
```

<210> SEQ ID NO 148
<211> LENGTH: 12
<212> TYPE: PRT
<213> ORGANISM: artificial sequence
<220> FEATURE:
<223> OTHER INFORMATION: synthetic construct

<400> SEQUENCE: 148

```
Gly Arg Lys Lys Arg Arg Gln Arg Arg Arg Pro Gln
1               5                   10
```

<210> SEQ ID NO 149
<211> LENGTH: 11
<212> TYPE: PRT
<213> ORGANISM: artificial sequence
<220> FEATURE:
<223> OTHER INFORMATION: synthetic construct

<400> SEQUENCE: 149

```
Tyr Gly Arg Lys Lys Arg Arg Gln Arg Arg Arg
1               5                   10
```

<210> SEQ ID NO 150
<211> LENGTH: 18
<212> TYPE: PRT
<213> ORGANISM: artificial sequence
<220> FEATURE:
<223> OTHER INFORMATION: synthetic construct

<400> SEQUENCE: 150

```
Lys Leu Ala Leu Lys Leu Ala Leu Lys Ala Leu Lys Ala Ala Leu Lys
1               5                   10                  15

Leu Ala
```

<210> SEQ ID NO 151
<211> LENGTH: 16
<212> TYPE: PRT
<213> ORGANISM: artificial sequence
<220> FEATURE:
<223> OTHER INFORMATION: synthetic construct

<400> SEQUENCE: 151

```
Arg Gln Ile Arg Ile Trp Phe Gln Asn Arg Arg Met Arg Trp Arg Arg
1               5                   10                  15
```

<210> SEQ ID NO 152
<211> LENGTH: 17
<212> TYPE: PRT
<213> ORGANISM: artificial sequence
<220> FEATURE:
<223> OTHER INFORMATION: synthetic construct

<400> SEQUENCE: 152

```
Cys Ser Ile Pro Pro Glu Val Lys Phe Asn Lys Pro Phe Val Tyr Leu
1               5                   10                  15

Ile
```

<210> SEQ ID NO 153
<211> LENGTH: 30
<212> TYPE: PRT
<213> ORGANISM: artificial sequence
<220> FEATURE:
<223> OTHER INFORMATION: synthetic construct

<400> SEQUENCE: 153

```
Arg Arg Arg Gln Arg Arg Lys Lys Arg Gly Gly Asp Ile Met Gly Glu
1               5                   10                  15

Trp Gly Asn Glu Ile Phe Gly Ala Ile Ala Gly Phe Leu Gly
            20                  25                  30
```

<210> SEQ ID NO 154
<211> LENGTH: 13
<212> TYPE: PRT
<213> ORGANISM: artificial sequence
<220> FEATURE:
<223> OTHER INFORMATION: synthetic construct

<400> SEQUENCE: 154

```
Phe Val Gln Trp Phe Ser Lys Phe Leu Gly Arg Ile Leu
1               5                   10
```

<210> SEQ ID NO 155
<211> LENGTH: 18
<212> TYPE: PRT
<213> ORGANISM: artificial sequence
<220> FEATURE:
<223> OTHER INFORMATION: synthetic construct

<400> SEQUENCE: 155

```
Leu Leu Ile Ile Leu Arg Arg Arg Ile Arg Lys Gln Ala His Ala His
1               5                   10                  15

Ser Lys
```

<210> SEQ ID NO 156
<211> LENGTH: 24
<212> TYPE: PRT
<213> ORGANISM: artificial sequence
<220> FEATURE:
<223> OTHER INFORMATION: synthetic construct

<400> SEQUENCE: 156

```
Leu Gly Thr Tyr Thr Gln Asp Phe Asn Lys Phe His Thr Phe Pro Gln
1               5                   10                  15

Thr Ala Ile Gly Val Gly Ala Pro
            20
```

<210> SEQ ID NO 157
<211> LENGTH: 30
<212> TYPE: PRT
<213> ORGANISM: artificial sequence
<220> FEATURE:
<223> OTHER INFORMATION: synthetic construct

<400> SEQUENCE: 157

```
Gly Ala Ala Glu Ala Ala Ala Arg Val Tyr Asp Leu Gly Leu Arg Arg
1               5                   10                  15

Leu Arg Gln Arg Arg Arg Leu Arg Arg Glu Arg Val Arg Ala
            20                  25                  30
```

<210> SEQ ID NO 158
<211> LENGTH: 27
<212> TYPE: PRT
<213> ORGANISM: artificial sequence
<220> FEATURE:
<223> OTHER INFORMATION: synthetic construct

<400> SEQUENCE: 158

```
Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25
```

<210> SEQ ID NO 159
<211> LENGTH: 18
<212> TYPE: PRT
<213> ORGANISM: artificial sequence
<220> FEATURE:
<223> OTHER INFORMATION: synthetic construct

<400> SEQUENCE: 159

```
Arg Gln Ile Lys Ile Trp Phe Gln Asn Arg Arg Met Lys Trp Lys Lys
1               5                   10                  15

Gly Gly
```

<210> SEQ ID NO 160
<211> LENGTH: 8
<212> TYPE: PRT
<213> ORGANISM: artificial sequence
<220> FEATURE:
<223> OTHER INFORMATION: synthetic construct

<400> SEQUENCE: 160

Arg Arg Arg Arg Arg Arg Arg Arg
1 5

<210> SEQ ID NO 161
<211> LENGTH: 9
<212> TYPE: PRT
<213> ORGANISM: artificial sequence
<220> FEATURE:
<223> OTHER INFORMATION: synthetic construct

<400> SEQUENCE: 161

Arg Arg Arg Arg Arg Arg Arg Arg Arg
1 5

<210> SEQ ID NO 162
<211> LENGTH: 30
<212> TYPE: PRT
<213> ORGANISM: artificial sequence
<220> FEATURE:
<223> OTHER INFORMATION: synthetic construct

<400> SEQUENCE: 162

Lys Lys Leu Phe Lys Lys Ile Leu Lys Tyr Leu Lys Lys Leu Phe Lys
1 5 10 15

Lys Ile Leu Lys Tyr Leu Lys Lys Lys Lys Lys Lys Lys Lys
20 25 30

<210> SEQ ID NO 163
<211> LENGTH: 14548
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (13426)..(13426)
<223> OTHER INFORMATION: n is a, c, g, or t

<400> SEQUENCE: 163
agtactttga tccaacccct ccgctgctat agtgcagtcg gcttctgacg ttcagtgcag 60
ccgtcttctg aaaacgacat gtcgcacaag tcctaagtta cgcgacaggc tgccgccctg 120
cccttttcct ggcgttttct tgtcgcgtgt tttagtcgca taaagtagaa tacttgcgac 180
tagaaccgga gacattacgc catgaacaag agcgccgccg ctggcctgct gggctatgcc 240
cgcgtcagca ccgacgacca ggacttgacc aaccaacggg ccgaactgca cgcggccggc 300
tgcaccaagc tgttttccga gaagatcacc ggcaccaggc gcgaccgccc ggagctggcc 360
aggatgcttg accacctacg ccctggcgac gttgtgacag tgaccaggct agaccgcctg 420
gcccgcagca cccgcgacct actggacatt gccgagcgca tccaggaggc cggcgcgggc 480
ctgcgtagcc tggcagagcc gtgggccgac accaccacgc cggccggccg catggtgttg 540
accgtgttcg ccggcattgc cgagttcgag cgttccctaa tcatcgaccg cacccggagc 600
gggcgcgagg ccgccaaggc ccgaggcgtg aagtttggcc cccgccctac cctcaccccg 660
gcacagatcg cgcacgcccg cgagctgatc gaccaggaag gccgcaccgt gaaagaggcg 720
gctgcactgc ttggcgtgca tcgctcgacc ctgtaccgcg cacttgagcg cagcgaggaa 780
gtgacgccca ccgaggccag gcggcgcggt gccttccgtg aggacgcatt gaccgaggcc 840
gacgccctgg cggccgccga gaatgaacgc caagaggaac aagcatgaaa ccgcaccagg 900
acggccagga cgaaccgttt ttcattaccg aagagatcga ggcggagatg atcgcggccg 960

-continued

```
ggtacgtgtt cgagccgccc gcgcacgtct caaccgtgcg gctgcatgaa atcctggccg   1020
gtttgtctga tgccaagctg gcggcctggc cggccagctt ggccgctgaa gaaaccgagc   1080
gccgccgtct aaaaaggtga tgtgtatttg agtaaaacag cttgcgtcat gcggtcgctg   1140
cgtatatgat gcgatgagta aataaacaaa tacgcaaggg gaacgcatga aggttatcgc   1200
tgtacttaac cagaaaggcg ggtcaggcaa gacgaccatc gcaacccatc tagcccgcgc   1260
cctgcaactc gccggggccg atgttctgtt agtcgattcc gatccccagg gcagtgcccg   1320
cgattgggcg gccgtgcggg aagatcaacc gctaaccgtt gtcggcatcg accgcccgac   1380
gattgaccgc gacgtgaagg ccatcggccg gcgcgacttc gtagtgatcg acggagcgcc   1440
ccaggcggcg gacttggctg tgtccgcgat caaggcagcc gacttcgtgc tgattccggt   1500
gcagccaagc ccttacgaca tatgggccac cgccgacctg gtggagctgg ttaagcagcg   1560
cattgaggtc acggatggaa ggctacaagc ggcctttgtc gtgtcgcggg cgatcaaagg   1620
cacgcgcatc ggcggtgagg ttgccgaggc gctggccggg tacgagctgc ccattcttga   1680
gtcccgtatc acgcagcgcg tgagctaccc aggcactgcc gccgccggca caaccgttct   1740
tgaatcagaa cccgagggcg acgctgcccg cgaggtccag gcgctggccg ctgaaattaa   1800
atcaaaactc atttgagtta atgaggtaaa gagaaaatga gcaaaagcac aaacacgcta   1860
agtgccggcc gtccgagcgc acgcagcagc aaggctgcaa cgttggccag cctggcagac   1920
acgccagcca tgaagcgggt caactttcag ttgccggcgg aggatcacac caagctgaag   1980
atgtacgcgg tacgccaagg caagaccatt accgagctgc tatctgaata catcgcgcag   2040
ctaccagagt aaatgagcaa atgaataaat gagtagatga attttagcgg ctaaaggagg   2100
cggcatggaa aatcaagaac aaccaggcac cgacgccgtg gaatgcccca tgtgtggagg   2160
aacgggcggt tggccaggcg taagcggctg ggttgtctgc cggccctgca atggcactgg   2220
aacccccaag cccgaggaat cggcgtgacg gtcgcaaacc atccggcccg gtacaaatcg   2280
gcgcggcgct gggtgatgac ctggtggaga agttgaaggc cgcgcaggcc gcccagcggc   2340
aacgcatcga ggcagaagca cgccccggtg aatcgtggca agcggccgct gatcgaatcc   2400
gcaaagaatc ccggcaaccg ccggcagccg gtgcgccgtc gattaggaag ccgcccaagg   2460
gcgacgagca accagatttt ttcgttccga tgctctatga cgtgggcacc cgcgatagtc   2520
gcagcatcat ggacgtggcc gttttccgtc tgtcgaagcg tgaccgacga gctggcgagg   2580
tgatccgcta cgagcttcca gacgggcacg tagaggtttc cgcagggccg gccggcatgg   2640
ccagtgtgtg ggattacgac ctggtactga tggcggtttc ccatctaacc gaatccatga   2700
accgataccg ggaagggaag ggagacaagc ccggccgcgt gttccgtcca cacgttgcgg   2760
acgtactcaa gttctgccgg cgagccgatg gcggaaagca gaaagacgac ctggtagaaa   2820
cctgcattcg gttaaacacc acgcacgttg ccatgcagcg tacgaagaag gccaagaacg   2880
gccgcctggt gacggtatcc gagggtgaag ccttgattag ccgctacaag atcgtaaaga   2940
gcgaaaccgg gcggccggag tacatcgaga tcgagctagc tgattggatg taccgcgaga   3000
tcacagaagg caagaacccg gacgtgctga cggttcaccc cgattacttt ttgatcgatc   3060
ccggcatcgg ccgttttctc taccgcctgg cacgccgcgc cgcaggcaag gcagaagcca   3120
gatggttgtt caagacgatc tacgaacgca gtggcagcgc cggagagttc aagaagttct   3180
gtttcaccgt gcgcaagctg atcgggtcaa atgacctgcc ggagtacgat ttgaaggagg   3240
aggcggggca ggctggcccg atcctagtca tgcgctaccg caacctgatc gagggcgaag   3300
```

```
catccgccgg ttcctaatgt acggagcaga tgctagggca aattgcccta gcaggggaaa   3360
aaggtcgaaa aggtctcttt cctgtggata gcacgtacat tgggaaccca aagccgtaca   3420
ttgggaaccg gaacccgtac attgggaacc caaagccgta cattgggaac cggtcacaca   3480
tgtaagtgac tgatataaaa gagaaaaaag gcgatttttc cgcctaaaac tctttaaaac   3540
ttattaaaac tcttaaaacc cgcctggcct gtgcataact gtctggccag cgcacagccg   3600
aagagctgca aaaagcgcct acccttcggt cgctgcgctc cctacgcccc gccgcttcgc   3660
gtcggcctat cgcggccgct ggccgctcaa aaatggctgg cctacggcca ggcaatctac   3720
cagggcgcgg acaagccgcg ccgtcgccac tcgaccgccg gcgcccacat caaggcaccc   3780
tgcctcgcgc gtttcggtga tgacggtgaa aacctctgac acatgcagct cccggagacg   3840
gtcacagctt gtctgtaagc ggatgccggg agcagacaag cccgtcaggg cgcgtcagcg   3900
ggtgttggcg ggtgtcgggg cgcagccatg acccagtcac gtagcgatag cggagtgtat   3960
actggcttaa ctatgcggca tcagagcaga ttgtactgag agtgcaccat atgcggtgtg   4020
aaataccgca cagatgcgta aggagaaaat accgcatcag gcgctcttcc gcttcctcgc   4080
tcactgactc gctgcgctcg gtcgttcggc tgcggcgagc ggtatcagct cactcaaagg   4140
cggtaatacg gttatccaca gaatcagggg ataacgcagg aaagaacatg tgagcaaaag   4200
gccagcaaaa ggccaggaac cgtaaaaagg ccgcgttgct ggcgtttttc cataggctcc   4260
gcccccctga cgagcatcac aaaaatcgac gctcaagtca gaggtggcga aacccgacag   4320
gactataaag ataccaggcg tttccccctg gaagctccct cgtgcgctct cctgttccga   4380
ccctgccgct taccggatac ctgtccgcct ttctcccttc gggaagcgtg gcgctttctc   4440
atagctcacg ctgtaggtat ctcagttcgg tgtaggtcgt tcgctccaag ctgggctgtg   4500
tgcacgaacc ccccgttcag cccgaccgct gcgccttatc cggtaactat cgtcttgagt   4560
ccaacccggt aagacacgac ttatcgccac tggcagcagc cactggtaac aggattagca   4620
gagcgaggta tgtaggcggt gctacagagt tcttgaagtg gtggcctaac tacggctaca   4680
ctagaaggac agtatttggt atctgcgctc tgctgaagcc agttaccttc ggaaaaagag   4740
ttggtagctc ttgatccggc aaacaaacca ccgctggtag cggtggtttt tttgtttgca   4800
agcagcagat tacgcgcaga aaaaaaggat ctcaagaaga tcctttgatc ttttctacgg   4860
ggtctgacgc tcagtggaac gaaaactcac gttaagggat tttggtcatg catgatatat   4920
ctcccaattt gtgtagggct tattatgcac gcttaaaaat aataaaagca gacttgacct   4980
gatagtttgg ctgtgagcaa ttatgtgctt agtgcatcta atcgcttgag ttaacgccgg   5040
cgaagcggcg tcggcttgaa cgaatttcta gctagacatt atttgccgac taccttggtg   5100
atctcgcctt tcacgtagtg gacaaattct tccaactgat ctgcgcgcga ggccaagcga   5160
tcttcttctt gtccaagata agcctgtcta gcttcaagta tgacgggctg atactgggcc   5220
ggcaggcgct ccattgccca gtcggcagcg acatccttcg gcgcgatttt gccggttact   5280
gcgctgtacc aaatgcggga caacgtaagc actacatttc gctcatcgcc agcccagtcg   5340
ggcggcgagt tccatagcgt taaggtttca tttagcgcct caaatagatc ctgttcagga   5400
accggatcaa agagttcctc cgccgctgga cctaccaagg caacgctatg ttctcttgct   5460
tttgtcagca agatagccag atcaatgtcg atcgtggctg gctcgaagat acctgcaaga   5520
atgtcattgc gctgccattc tccaaattgc agttcgcgct tagctggata acgccacgga   5580
atgatgtcgt cgtgcacaac aatggtgact tctacagcgc ggagaatctc gctctctcca   5640
ggggaagccg aagtttccaa aaggtcgttg atcaaagctc gccgcgttgt ttcatcaagc   5700
```

cttacggtca ccgtaaccag caaatcaata tcactgtgtg gcttcaggcc gccatccact 5760
gcggagccgt acaaatgtac ggccagcaac gtcggttcga gatggcgctc gatgacgcca 5820
actacctctg atagttgagt cgatacttcg gcgatcaccg cttccccat gatgtttaac 5880
tttgttttag ggcgactgcc ctgctgcgta acatcgttgc tgctccataa catcaaacat 5940
cgacccacgg cgtaacgcgc ttgctgcttg gatgcccgag gcatagactg taccccaaaa 6000
aaacatgtca taacaagaag ccatgaaaac cgccactgcg ccgttaccac cgctgcgttc 6060
ggtcaaggtt ctggaccagt tgcgtgacgg cagttacgct acttgcatta cagcttacga 6120
accgaacgag gcttatgtcc actgggttcg tgcccgaatt gatcacaggc agcaacgctc 6180
tgtcatcgtt acaatcaaca tgctaccctc cgcgagatca tccgtgtttc aaacccggca 6240
gcttagttgc cgttcttccg aatagcatcg gtaacatgag caaagtctgc cgccttacaa 6300
cggctctccc gctgacgccg tcccggactg atgggctgcc tgtatcgagt ggtgattttg 6360
tgccgagctg ccggtcgggg agctgttggc tggctggtgg caggatatat tgtggtgtaa 6420
acaaattgac gcttagacaa cttaataaca cattgcggac gtttttaatg tactgaatta 6480
acgccgaatt gctctagcca atacgcaaac cgcctctccc cgcgcgttgg ccgattcatt 6540
aatgcagctg gcacgacagg tttcccgact ggaaagcggg cagtgagcgc aacgcaatta 6600
atgtgagtta gctcactcat taggcacccc aggctttaca ctttatgctt ccggctcgta 6660
tgttgtgtgg aattgtgagc ggataacaat ttcacacagg aaacagctat gacatgatta 6720
cgaattcaaa aattacggat atgaatatag gcatatccgt atccgaatta tccgtttgac 6780
agctagcaac gattgtacaa ttgcttcttt aaaaaaggaa gaaagaaaga aagaaaagaa 6840
tcaacatcag cgttaacaaa cggccccgtt acggcccaaa cggtcatata gagtaacggc 6900
gttaagcgtt gaaagactcc tatcgaaata cgtaaccgca aacgtgtcat agtcagatcc 6960
cctcttcctt caccgcctca aacacaaaaa taatcttcta cagcctatat atacaacccc 7020
cccttctatc tctcctttct cacaattcat catctttctt tctctacccc caattttaag 7080
aaatcctctc ttctcctctt cattttcaag gtaaatctct ctctctctct ctctctctgt 7140
tattccttgt tttaattagg tatgtattat tgctagtttg ttaatctgct tatcttatgt 7200
atgccttatg tgaatatctt tatcttgttc atctcatccg tttagaagct ataaatttgt 7260
tgatttgact gtgtatctac acgtggttat gtttatatct aatcagatat gaatttcttc 7320
atattgttgc gtttgtgtgt accaatccga aatcgttgat ttttttcatt taatcgtgta 7380
gctaattgta cgtatacata tggatctacg tatcaattgt tcatctgttt gtgtttgtat 7440
gtatacagat ctgaaaacat cacttctctc atctgattgt gttgttacat acatagatat 7500
agatctgtta tatcattttt tttattaatt gtgtatatat atatgtgcat agatctggat 7560
tacatgattg tgattattta catgattttg ttatttacgt atgtatatat gtagatctgg 7620
actttttgga gttgttgact tgattgtatt tgtgtgtgta tatgtgtgtt ctgatcttga 7680
tatgttatgt atgtgcagcg aattcggcgc gccatggata agaagtactc tatcggactc 7740
gatatcggaa ctaactctgt gggatgggct gtgatcaccg atgagtacaa ggtgccatct 7800
aagaagttca aggttctcgg aaacaccgat aggcactcta tcaagaaaaa ccttatcggt 7860
gctctcctct tcgattctgg tgaaactgct gaggctacca gactcaagag aaccgctaga 7920
agaaggtaca ccagaagaaa gaacaggatc tgctacctcc aagagatctt ctctaacgag 7980
atggctaaag tggatgattc attcttccac aggctcgaag agtcattcct cgtggaagaa 8040

-continued

```
gataagaagc acgagaggca ccctatcttc ggaaacatcg ttgatgaggt ggcataccac   8100
gagaagtacc ctactatcta ccacctcaga aagaagctcg ttgattctac tgataaggct   8160
gatctcaggc tcatctacct cgctctcgct cacatgatca agttcagagg acacttcctc   8220
atcgagggtg atctcaaccc tgataactct gatgtggata agttgttcat ccagctcgtg   8280
cagacctaca accagctttt cgaagagaac cctatcaacg cttcaggtgt ggatgctaag   8340
gctatcctct ctgctaggct ctctaagtca agaaggcttg agaacctcat tgctcagctc   8400
cctggtgaga agaagaacgg acttttcgga aacttgatcg ctctctctct cggactcacc   8460
cctaacttca agtctaactt cgatctcgct gaggatgcaa agctccagct ctcaaaggat   8520
acctacgatg atgatctcga taacctcctc gctcagatcg gagatcagta cgctgatttg   8580
ttcctcgctg ctaagaacct ctctgatgct atcctcctca gtgatatcct cagagtgaac   8640
accgagatca ccaaggctcc actctcagct tctatgatca agagatacga tgagcaccac   8700
caggatctca cacttctcaa ggctcttgtt agacagcagc tcccagagaa gtacaaagag   8760
atttcttcg atcagtctaa gaacggatac gctggttaca tcgatggtgg tgcatctcaa   8820
gaagagttct acaagttcat caagcctatc ctcgagaaga tggatggaac cgaggaactc   8880
ctcgtgaagc tcaatagaga ggatcttctc agaaagcaga ggaccttcga taacggatct   8940
atccctcatc agatccacct cggagagttg cacgctatcc ttagaaggca agaggatttc   9000
tacccattcc tcaaggataa cagggaaaag attgagaaga ttctcacctt cagaatccct   9060
tactacgtgg gacctctcgc tagaggaaac tcaagattcg cttggatgac cagaaagtct   9120
gaggaaacca tcaccccttg gaacttcgaa gaggtggtgg ataagggtgc tagtgctcag   9180
tctttcatcg agaggatgac caacttcgat aagaaccttc caaacgagaa ggtgctccct   9240
aagcactctt tgctctacga gtacttcacc gtgtacaacg agttgaccaa ggttaagtac   9300
gtgaccgagg gaatgaggaa gcctgctttt ttgtcaggtg agcaaaagaa ggctatcgtt   9360
gatctcttgt tcaagaccaa cagaaaggtg accgtgaagc agctcaaaga ggattacttc   9420
aagaaaatcg agtgcttcga ttcagttgag atttctggtg ttgaggatag gttcaacgca   9480
tctctcggaa cctaccacga tctcctcaag atcattaagg ataaggattt cttggataac   9540
gaggaaaacg aggatatctt ggaggatatc gttcttaccc tcaccctctt tgaagataga   9600
gagatgattg aagaaaggct caagacctac gctcatctct tcgatgataa ggtgatgaag   9660
cagttgaaga gaagaagata cactggttgg ggaaggctct caagaaagct cattaacgga   9720
atcagggata agcagtctgg aaagacaatc cttgatttcc tcaagtctga tggattcgct   9780
aacagaaact tcatgcagct catccacgat gattctctca cctttaaaga ggatatccag   9840
aaggctcagg tttcaggaca gggtgatagt ctccatgagc atatcgctaa cctcgctgga   9900
tctcctgcaa tcaagaaggg aatcctccag actgtgaagg ttgtggatga gttggtgaag   9960
gtgatgggaa ggcataagcc tgagaacatc gtgatcgaaa tggctagaga gaaccagacc  10020
actcagaagg gacagaagaa ctctagggaa aggatgaaga ggatcgagga aggtatcaaa  10080
gagcttggat ctcagatcct caaagagcac cctgttgaga acactcagct ccagaatgag  10140
aagctctacc tctactacct ccagaacgga agggatatgt atgtggatca agagttggat  10200
atcaacaggc tctctgatta cgatgttgat catatcgtgc cacagtcatt cttgaaggat  10260
gattctatcg ataacaaggt gctcaccagg tctgataaga acaggggtaa gagtgataac  10320
gtgccaagtg aagaggttgt gaagaaaatg aagaactatt ggaggcagct cctcaacgct  10380
aagctcatca ctcagagaaa gttcgataac ttgactaagg ctgagagggg aggactctct  10440
```

```
gaattggata aggcaggatt catcaagagg cagcttgtgg aaaccaggca gatcactaag  10500
cacgttgcac agatcctcga ttctaggatg aacaccaagt acgatgagaa cgataagttg  10560
atcagggaag tgaaggttat caccctcaag tcaaagctcg tgtctgattt cagaaaggat  10620
ttccaattct acaaggtgag ggaaatcaac aactaccacc acgctcacga tgcttacctt  10680
aacgctgttg ttggaaccgc tctcatcaag aagtatccta agctcgagtc agagttcgtg  10740
tacggtgatt acaaggtgta cgatgtgagg aagatgatcg ctaagtctga gcaagagatc  10800
ggaaaggcta ccgctaagta tttcttctac tctaacatca tgaatttctt caagaccgag  10860
attaccctcg ctaacggtga gatcagaaag aggccactca tcgagacaaa cggtgaaaca  10920
ggtgagatcg tgtgggataa gggaagggat ttcgctaccg ttagaaaggt gctctctatg  10980
ccacaggtga acatcgttaa gaaaaccgag gtgcagaccg gtggattctc taaagagtct  11040
atcctcccta agaggaactc tgataagctc attgctagga agaaggattg ggaccctaag  11100
aaatacggtg gtttcgattc tcctaccgtg gcttactctg ttctcgttgt ggctaaggtt  11160
gagaagggaa agagtaagaa gctcaagtct gttaaggaac ttctcggaat cactatcatg  11220
gaaaggtcat ctttcgagaa gaacccaatc gatttcctcg aggctaaggg atacaaagag  11280
gttaagaagg atctcatcat caagctccca aagtactcac tcttcgaact cgagaacggt  11340
agaaagagga tgctcgcttc tgctggtgag cttcaaaagg gaaacgagct tgctctccca  11400
tctaagtacg ttaactttct ttacctcgct tctcactacg agaagttgaa gggatctcca  11460
gaagataacg agcagaagca acttttcgtt gagcagcaca agcactactt ggatgagatc  11520
atcgagcaga tctctgagtt ctctaaaagg gtgatcctcg ctgatgcaaa cctcgataag  11580
gtgttgtctg cttacaacaa gcacagagat aagcctatca gggaacaggc agagaacatc  11640
atccatctct tcacccttac caacctcggt gctcctgctg ctttcaagta cttcgataca  11700
accatcgata ggaagagata cacctctacc aaagaagtgc tcgatgctac cctcatccat  11760
cagtctatca ctggactcta cgagactagg atcgatctct cacagctcgg tggtgattca  11820
agggctgatc ctaagaagaa gaggaaggtt tgaggcgcgc cgagctccag gcctcccagc  11880
tttcgtccgt atcatcggtt tcgacaacgt tcgtcaagtt caatgcatca gtttcattgc  11940
ccacacacca gaatcctact aagtttgagt attatggcat tggaaaagct gttttcttct  12000
atcatttgtt ctgcttgtaa tttactgtgt tctttcagtt tttgttttcg gacatcaaaa  12060
tgcaaatgga tggataagag ttaataaatg atatggtcct tttgttcatt ctcaaattat  12120
tattatctgt tgtttttact ttaatgggtt gaatttaagt aagaaaggaa ctaacagtgt  12180
gatattaagg tgcaatgtta gacatataaa acagtctttc acctctcttt ggttatgtct  12240
tgaattggtt tgtttcttca cttatctgtg taatcaagtt tactatgagt ctatgatcaa  12300
gtaattatgc aatcaagtta agtacagtat aggcttgagc tccctaggct tttttcttc  12360
ttcttcgttc atacagtttt tttttgttta tcagcttaca ttttcttgaa ccgtagcttt  12420
cgttttcttc tttttaactt tccattcgga gtttttgtat cttgtttcat agtttgtccc  12480
aggattagaa tgattaggca tcgaaccttc aagaatttga ttgaataaaa catcttcatt  12540
cttaagatat gaagataatc ttcaaaaggc ccctgggaat ctgaaagaag agaagcaggc  12600
ccatttatat gggaaagaac aatagtattt cttatatagg cccatttaag ttgaaaacaa  12660
tcttcaaaag tcccacatcg cttagataag aaaacgaagc tgagtttata tacagctaga  12720
gtcgaagtag tgattggaag caagagacgt tctagggttt tagagctaga aatagcaagt  12780
```

```
taaaataagg ctagtccgtt atcaacttga aaaagtggca ccgagtcggt gctttttttc  12840

tagacccagc tttcttgtac aaagttggca ttacctaggc ccgggcctga ggacgcgtcc  12900

atggttaatt aagacgtccg gaccgactag tggatcctct agagtcgacc tgcaggcatg  12960

caagcttctt cgtcaacatg gtggagcacg acacgcttgt ctactccaaa aatatcaaag  13020

atacagtctc agaagaccaa agggcaattg agacttttca acaaagggta atatccggaa  13080

acctcctcgg attccattgc ccagctatct gtcactttat tgtgaagata gtggaaaagg  13140

aaggtggctc ctacaaatgc catcattgcg ataaaggaaa ggccatcgtt gaagatgcct  13200

ctgccgacag tggtcccaaa gatggacccc cacccacgag gagcatcgtg gaaaaagaag  13260

acgttccaac cacgtcttca aagcaagtgg attgatgtga tatctccact gacgtaaggg  13320

atgacgcaca atcaatccca ctatccttcg caagaccctt ttaaggggga agttcatttc  13380

atttggagag gacacgctga aatcaccagt ctctctgtac aaatcnatct ctctctataa  13440

tattgtgtaa gtagttccca gataagggaa ttagggttct tatagggttt cgctcagctg  13500

ttgagcatat aagaaaccct tagtcgatag atctgttggg gatctaccat gagcccagaa  13560

cgacgcccgg ccgacatccg ccgtgccacc gaggcggaca tgccggcggt ctgcaccatc  13620

gtcaaccact acatcgagac aagcacggtc aacttccgta ccgagccgca ggaaccgcag  13680

gagtggacgg acgacctcgt ccgtctgcgg gagcgctatc cctggctcgt cgccgaggtg  13740

gacggcgagg tcgccggcat cgcctacgcg ggcccctgga aggcacgcaa cgcctacgac  13800

tggacggccg agtcgaccgt gtacgtctcc ccccgccacc agcggacggg actgggctcc  13860

acgctctaca cccacctgct gaagtccctg gaggcacagg gcttcaagag cgtggtcgct  13920

gtcatcgggc tgcccaacga cccgagcgtg cgcatgcacg aggcgctcgg atatgccccc  13980

cgcggcatgc tgcgggcggc cggcttcaag cacgggaact ggcatgacgt gggtttctgg  14040

cagctggact tcagcctgcc ggtaccgccc cgtccggtcc tgcccgtcac cgagatctga  14100

tgacccaact tagtatgtat ttgtatttgt aaaatacttc tatcaataaa atttctaatt  14160

cctaaaacca aaatccaggg gtaccgaaca agcttggcac tggccgtcgt tttacaacgt  14220

cgtgactggg aaaaccctgg cgttacccaa cttaatcgcc ttgcagcaca tccccctttc  14280

gccagctggc gtaatagcga agaggcccgc accgatcgcc cttcccaaca gttgcgcagc  14340

ctgaatggcg aatgagcttg agcttggatc agattgtcgt ttcccgcctt cagtttaaac  14400

tatcagtgtt tgacaggata tattggcggg taaacctaag agaaaagagc gtttattaga  14460

ataacggata tttaaaaggg cgtgaaaagg tttatccgtt cgtccatttg tatgtgcatg  14520

ccaaccacag ggttcccctc gggatcaa                                     14548
```

<210> SEQ ID NO 164
<211> LENGTH: 14548
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (13426)..(13426)
<223> OTHER INFORMATION: n is a, c, g, or t

<400> SEQUENCE: 164

```
agtactttga tccaacccct ccgctgctat agtgcagtcg gcttctgacg ttcagtgcag     60

ccgtcttctg aaaacgacat gtcgcacaag tcctaagtta cgcgacaggc tgccgccctg    120

cccttttcct ggcgttttct tgtcgcgtgt tttagtcgca taaagtagaa tacttgcgac    180
```

```
tagaaccgga gacattacgc catgaacaag agcgccgccg ctggcctgct gggctatgcc    240
cgcgtcagca ccgacgacca ggacttgacc aaccaacggg ccgaactgca cgcggccggc    300
tgcaccaagc tgttttccga gaagatcacc ggcaccaggc gcgaccgccc ggagctggcc    360
aggatgcttg accacctacg ccctggcgac gttgtgacag tgaccaggct agaccgcctg    420
gcccgcagca cccgcgacct actggacatt gccgagcgca tccaggaggc cggcgcgggc    480
ctgcgtagcc tggcagagcc gtgggccgac accaccacgc cggccggccg catggtgttg    540
accgtgttcg ccggcattgc cgagttcgag cgttccctaa tcatcgaccg cacccggagc    600
gggcgcgagg ccgccaaggc ccgaggcgtg aagtttggcc cccgccctac cctcaccccg    660
gcacagatcg cgcacgcccg cgagctgatc gaccaggaag gccgcaccgt gaaagaggcg    720
gctgcactgc ttggcgtgca tcgctcgacc ctgtaccgcg cacttgagcg cagcgaggaa    780
gtgacgccca ccgaggccag gcggcgcggt gccttccgtg aggacgcatt gaccgaggcc    840
gacgccctgg cggccgccga gaatgaacgc caagaggaac aagcatgaaa ccgcaccagg    900
acggccagga cgaaccgttt ttcattaccg aagagatcga ggcggagatg atcgcggccg    960
ggtacgtgtt cgagccgccc gcgcacgtct caaccgtgcg gctgcatgaa atcctggccg   1020
gtttgtctga tgccaagctg gcggcctggc cggccagctt ggccgctgaa gaaaccgagc   1080
gccgccgtct aaaaaggtga tgtgtatttg agtaaaacag cttgcgtcat gcggtcgctg   1140
cgtatatgat gcgatgagta aataaacaaa tacgcaaggg gaacgcatga aggttatcgc   1200
tgtacttaac cagaaaggcg ggtcaggcaa gacgaccatc gcaacccatc tagcccgcgc   1260
cctgcaactc gccggggccg atgttctgtt agtcgattcc gatccccagg gcagtgcccg   1320
cgattgggcg gccgtgcggg aagatcaacc gctaaccgtt gtcggcatcg accgcccgac   1380
gattgaccgc gacgtgaagg ccatcggccg gcgcgacttc gtagtgatcg acggagcgcc   1440
ccaggcggcg gacttggctg tgtccgcgat caaggcagcc gacttcgtgc tgattccggt   1500
gcagccaagc ccttacgaca tatgggccac cgccgacctg gtggagctgg ttaagcagcg   1560
cattgaggtc acggatggaa ggctacaagc ggcctttgtc gtgtcgcggg cgatcaaagg   1620
cacgcgcatc ggcggtgagg ttgccgaggc gctggccggg tacgagctgc ccattcttga   1680
gtcccgtatc acgcagcgcg tgagctaccc aggcactgcc gccgccggca caaccgttct   1740
tgaatcagaa cccgagggcg acgctgcccg cgaggtccag gcgctggccg ctgaaattaa   1800
atcaaaactc atttgagtta atgaggtaaa gagaaaatga gcaaaagcac aaacacgcta   1860
agtgccggcc gtccgagcgc acgcagcagc aaggctgcaa cgttggccag cctggcagac   1920
acgccagcca tgaagcgggt caactttcag ttgccggcgg aggatcacac caagctgaag   1980
atgtacgcgg tacgccaagg caagaccatt accgagctgc tatctgaata catcgcgcag   2040
ctaccagagt aaatgagcaa atgaataaat gagtagatga attttagcgg ctaaaggagg   2100
cggcatggaa aatcaagaac aaccaggcac cgacgccgtg gaatgcccca tgtgtggagg   2160
aacgggcggt tggccaggcg taagcggctg ggttgtctgc cggccctgca atggcactgg   2220
aacccccaag cccgaggaat cggcgtgacg gtcgcaaacc atccggcccg gtacaaatcg   2280
gcgcggcgct gggtgatgac ctggtggaga agttgaaggc cgcgcaggcc gcccagcggc   2340
aacgcatcga ggcagaagca cgccccggtg aatcgtggca agcggccgct gatcgaatcc   2400
gcaaagaatc ccggcaaccg ccggcagccg gtgcgccgtc gattaggaag ccgcccaagg   2460
gcgacgagca accagatttt ttcgttccga tgctctatga cgtgggcacc cgcgatagtc   2520
```

-continued

```
gcagcatcat ggacgtggcc gttttccgtc tgtcgaagcg tgaccgacga gctggcgagg   2580
tgatccgcta cgagcttcca gacgggcacg tagaggtttc cgcagggccg gccggcatgg   2640
ccagtgtgtg ggattacgac ctggtactga tggcggtttc ccatctaacc gaatccatga   2700
accgataccg ggaagggaag ggagacaagc ccggccgcgt gttccgtcca cacgttgcgg   2760
acgtactcaa gttctgccgg cgagccgatg gcggaaagca gaaagacgac ctggtagaaa   2820
cctgcattcg gttaaacacc acgcacgttg ccatgcagcg tacgaagaag gccaagaacg   2880
gccgcctggt gacggtatcc gagggtgaag ccttgattag ccgctacaag atcgtaaaga   2940
gcgaaaccgg gcggccggag tacatcgaga tcgagctagc tgattggatg taccgcgaga   3000
tcacagaagg caagaacccg gacgtgctga cggttcaccc cgattacttt ttgatcgatc   3060
ccggcatcgg ccgttttctc taccgcctgg cacgccgcgc cgcaggcaag gcagaagcca   3120
gatggttgtt caagacgatc tacgaacgca gtggcagcgc cggagagttc aagaagttct   3180
gtttcaccgt gcgcaagctg atcgggtcaa atgacctgcc ggagtacgat ttgaaggagg   3240
aggcggggca ggctggcccg atcctagtca tgcgctaccg caacctgatc gagggcgaag   3300
catccgccgg ttcctaatgt acggagcaga tgctagggca aattgcccta gcaggggaaa   3360
aaggtcgaaa aggtctcttt cctgtggata gcacgtacat tgggaaccca aagccgtaca   3420
ttgggaaccg gaacccgtac attgggaacc caaagccgta cattgggaac cggtcacaca   3480
tgtaagtgac tgatataaaa gagaaaaaag gcgatttttc cgcctaaaac tctttaaaac   3540
ttattaaaac tcttaaaacc cgcctggcct gtgcataact gtctggccag cgcacagccg   3600
aagagctgca aaaagcgcct acccttcggt cgctgcgctc cctacgcccc gccgcttcgc   3660
gtcggcctat cgcggccgct ggccgctcaa aaatggctgg cctacggcca ggcaatctac   3720
cagggcgcgg acaagccgcg ccgtcgccac tcgaccgccg gcgcccacat caaggcaccc   3780
tgcctcgcgc gtttcggtga tgacggtgaa aacctctgac acatgcagct cccggagacg   3840
gtcacagctt gtctgtaagc ggatgccggg agcagacaag cccgtcaggg cgcgtcagcg   3900
ggtgttggcg ggtgtcgggg cgcagccatg acccagtcac gtagcgatag cggagtgtat   3960
actggcttaa ctatgcggca tcagagcaga ttgtactgag agtgcaccat atgcggtgtg   4020
aaataccgca cagatgcgta aggagaaaat accgcatcag gcgctcttcc gcttcctcgc   4080
tcactgactc gctgcgctcg gtcgttcggc tgcggcgagc ggtatcagct cactcaaagg   4140
cggtaatacg gttatccaca gaatcagggg ataacgcagg aaagaacatg tgagcaaaag   4200
gccagcaaaa ggccaggaac cgtaaaaagg ccgcgttgct ggcgtttttc cataggctcc   4260
gcccccctga cgagcatcac aaaaatcgac gctcaagtca gaggtggcga aacccgacag   4320
gactataaag ataccaggcg tttccccctg gaagctccct cgtgcgctct cctgttccga   4380
ccctgccgct taccggatac ctgtccgcct ttctcccttc gggaagcgtg gcgctttctc   4440
atagctcacg ctgtaggtat ctcagttcgg tgtaggtcgt tcgctccaag ctgggctgtg   4500
tgcacgaacc ccccgttcag cccgaccgct gcgccttatc cggtaactat cgtcttgagt   4560
ccaacccggt aagacacgac ttatcgccac tggcagcagc cactggtaac aggattagca   4620
gagcgaggta tgtaggcggt gctacagagt tcttgaagtg gtggcctaac tacggctaca   4680
ctagaaggac agtatttggt atctgcgctc tgctgaagcc agttaccttc ggaaaaagag   4740
ttggtagctc ttgatccggc aaacaaacca ccgctggtag cggtggtttt tttgtttgca   4800
agcagcagat tacgcgcaga aaaaaaggat ctcaagaaga tcctttgatc ttttctacgg   4860
ggtctgacgc tcagtggaac gaaaactcac gttaagggat tttggtcatg catgatatat   4920
```

```
ctcccaattt gtgtagggct tattatgcac gcttaaaaat aataaaagca gacttgacct   4980
gatagtttgg ctgtgagcaa ttatgtgctt agtgcatcta atcgcttgag ttaacgccgg   5040
cgaagcggcg tcggcttgaa cgaatttcta gctagacatt atttgccgac taccttggtg   5100
atctcgcctt tcacgtagtg gacaaattct tccaactgat ctgcgcgcga ggccaagcga   5160
tcttcttctt gtccaagata agcctgtcta gcttcaagta tgacgggctg atactgggcc   5220
ggcaggcgct ccattgccca gtcggcagcg acatccttcg gcgcgatttt gccggttact   5280
gcgctgtacc aaatgcggga caacgtaagc actacatttc gctcatcgcc agcccagtcg   5340
ggcggcgagt tccatagcgt taaggtttca tttagcgcct caaatagatc ctgttcagga   5400
accggatcaa agagttcctc cgccgctgga cctaccaagg caacgctatg ttctcttgct   5460
tttgtcagca agatagccag atcaatgtcg atcgtggctg gctcgaagat acctgcaaga   5520
atgtcattgc gctgccattc tccaaattgc agttcgcgct tagctggata acgccacgga   5580
atgatgtcgt cgtgcacaac aatggtgact tctacagcgc ggagaatctc gctctctcca   5640
ggggaagccg aagtttccaa aaggtcgttg atcaaagctc gccgcgttgt ttcatcaagc   5700
cttacggtca ccgtaaccag caaatcaata tcactgtgtg gcttcaggcc gccatccact   5760
gcggagccgt acaaatgtac ggccagcaac gtcggttcga gatggcgctc gatgacgcca   5820
actacctctg atagttgagt cgatacttcg gcgatcaccg cttcccccat gatgtttaac   5880
tttgttttag ggcgactgcc ctgctgcgta acatcgttgc tgctccataa catcaaacat   5940
cgacccacgg cgtaacgcgc ttgctgcttg gatgcccgag gcatagactg taccccaaaa   6000
aaacatgtca taacaagaag ccatgaaaac cgccactgcg ccgttaccac cgctgcgttc   6060
ggtcaaggtt ctggaccagt tgcgtgacgg cagttacgct acttgcatta cagcttacga   6120
accgaacgag gcttatgtcc actgggttcg tgcccgaatt gatcacaggc agcaacgctc   6180
tgtcatcgtt acaatcaaca tgctaccctc cgcgagatca tccgtgtttc aaacccggca   6240
gcttagttgc cgttcttccg aatagcatcg gtaacatgag caaagtctgc cgccttacaa   6300
cggctctccc gctgacgccg tcccggactg atgggctgcc tgtatcgagt ggtgattttg   6360
tgccgagctg ccggtcgggg agctgttggc tggctggtgg caggatatat tgtggtgtaa   6420
acaaattgac gcttagacaa cttaataaca cattgcggac gtttttaatg tactgaatta   6480
acgccgaatt gctctagcca atacgcaaac cgcctctccc cgcgcgttgg ccgattcatt   6540
aatgcagctg gcacgacagg tttcccgact ggaaagcggg cagtgagcgc aacgcaatta   6600
atgtgagtta gctcactcat taggcacccc aggctttaca ctttatgctt ccggctcgta   6660
tgttgtgtgg aattgtgagc ggataacaat ttcacacagg aaacagctat gacatgatta   6720
cgaattcaaa aattacggat atgaatatag gcatatccgt atccgaatta tccgtttgac   6780
agctagcaac gattgtacaa ttgcttcttt aaaaaaggaa gaaagaaaga aagaaaagaa   6840
tcaacatcag cgttaacaaa cggccccgtt acggcccaaa cggtcatata gagtaacggc   6900
gttaagcgtt gaaagactcc tatcgaaata cgtaaccgca aacgtgtcat agtcagatcc   6960
cctcttcctt caccgcctca aacacaaaaa taatcttcta cagcctatat atacaacccc   7020
cccttctatc tctcctttct cacaattcat catctttctt tctctacccc caattttaag   7080
aaatcctctc ttctcctctt cattttcaag gtaaatctct ctctctctct ctctctctgt   7140
tattccttgt tttaattagg tatgtattat tgctagtttg ttaatctgct tatcttatgt   7200
atgccttatg tgaatatctt tatcttgttc atctcatccg tttagaagct ataaatttgt   7260
```

-continued

```
tgatttgact gtgtatctac acgtggttat gtttatatct aatcagatat gaatttcttc   7320
atattgttgc gtttgtgtgt accaatccga aatcgttgat ttttttcatt taatcgtgta   7380
gctaattgta cgtatacata tggatctacg tatcaattgt tcatctgttt gtgtttgtat   7440
gtatacagat ctgaaaacat cacttctctc atctgattgt gttgttacat acatagatat   7500
agatctgtta tatcattttt tttattaatt gtgtatatat atatgtgcat agatctggat   7560
tacatgattg tgattattta catgattttg ttatttacgt atgtatatat gtagatctgg   7620
actttttgga gttgttgact tgattgtatt tgtgtgtgta tatgtgtgtt ctgatcttga   7680
tatgttatgt atgtgcagcg aattcggcgc gccatggata agaagtactc tatcggactc   7740
gatatcggaa ctaactctgt gggatgggct gtgatcaccg atgagtacaa ggtgccatct   7800
aagaagttca aggttctcgg aaacaccgat aggcactcta tcaagaaaaa ccttatcggt   7860
gctctcctct tcgattctgg tgaaactgct gaggctacca gactcaagag aaccgctaga   7920
agaaggtaca ccagaagaaa gaacaggatc tgctacctcc aagagatctt ctctaacgag   7980
atggctaaag tggatgattc attcttccac aggctcgaag agtcattcct cgtggaagaa   8040
gataagaagc acgagaggca ccctatcttc ggaaacatcg ttgatgaggt ggcataccac   8100
gagaagtacc ctactatcta ccacctcaga aagaagctcg ttgattctac tgataaggct   8160
gatctcaggc tcatctacct cgctctcgct cacatgatca agttcagagg acacttcctc   8220
atcgagggtg atctcaaccc tgataactct gatgtggata agttgttcat ccagctcgtg   8280
cagacctaca accagctttt cgaagagaac cctatcaacg cttcaggtgt ggatgctaag   8340
gctatcctct ctgctaggct ctctaagtca agaaggcttg agaacctcat tgctcagctc   8400
cctggtgaga agaagaacgg acttttcgga aacttgatcg ctctctctct cggactcacc   8460
cctaacttca agtctaactt cgatctcgct gaggatgcaa agctccagct ctcaaaggat   8520
acctacgatg atgatctcga taacctcctc gctcagatcg gagatcagta cgctgatttg   8580
ttcctcgctg ctaagaacct ctctgatgct atcctcctca gtgatatcct cagagtgaac   8640
accgagatca ccaaggctcc actctcagct tctatgatca agagatacga tgagcaccac   8700
caggatctca cacttctcaa ggctcttgtt agacagcagc tcccagagaa gtacaaagag   8760
attttcttcg atcagtctaa gaacggatac gctggttaca tcgatggtgg tgcatctcaa   8820
gaagagttct acaagttcat caagcctatc ctcgagaaga tggatggaac cgaggaactc   8880
ctcgtgaagc tcaatagaga ggatcttctc agaaagcaga ggaccttcga taacggatct   8940
atccctcatc agatccacct cggagagttg cacgctatcc ttagaaggca agaggatttc   9000
tacccattcc tcaaggataa cagggaaaag attgagaaga ttctcacctt cagaatccct   9060
tactacgtgg gacctctcgc tagaggaaac tcaagattcg cttggatgac cagaaagtct   9120
gaggaaacca tcaccccttg gaacttcgaa gaggtggtgg ataagggtgc tagtgctcag   9180
tctttcatcg agaggatgac caacttcgat aagaaccttc caaacgagaa ggtgctccct   9240
aagcactctt tgctctacga gtacttcacc gtgtacaacg agttgaccaa ggttaagtac   9300
gtgaccgagg gaatgaggaa gcctgctttt ttgtcaggtg agcaaaagaa ggctatcgtt   9360
gatctcttgt tcaagaccaa cagaaaggtg accgtgaagc agctcaaaga ggattacttc   9420
aagaaaatcg agtgcttcga ttcagttgag atttctggtg ttgaggatag gttcaacgca   9480
tctctcggaa cctaccacga tctcctcaag atcattaagg ataaggattt cttggataac   9540
gaggaaaacg aggatatctt ggaggatatc gttcttaccc tcaccctctt tgaagataga   9600
gagatgattg aagaaaggct caagacctac gctcatctct tcgatgataa ggtgatgaag   9660
```

```
cagttgaaga gaagaagata cactggttgg ggaaggctct caagaaagct cattaacgga   9720
atcagggata agcagtctgg aaagacaatc cttgatttcc tcaagtctga tggattcgct   9780
aacagaaact tcatgcagct catccacgat gattctctca cctttaaaga ggatatccag   9840
aaggctcagg tttcaggaca gggtgatagt ctccatgagc atatcgctaa cctcgctgga   9900
tctcctgcaa tcaagaaggg aatcctccag actgtgaagg ttgtggatga gttggtgaag   9960
gtgatgggaa ggcataagcc tgagaacatc gtgatcgaaa tggctagaga gaaccagacc  10020
actcagaagg gacagaagaa ctctagggaa aggatgaaga ggatcgagga aggtatcaaa  10080
gagcttggat ctcagatcct caaagagcac cctgttgaga acactcagct ccagaatgag  10140
aagctctacc tctactacct ccagaacgga agggatatgt atgtggatca agagttggat  10200
atcaacaggc tctctgatta cgatgttgat catatcgtgc cacagtcatt cttgaaggat  10260
gattctatcg ataacaaggt gctcaccagg tctgataaga acaggggtaa gagtgataac  10320
gtgccaagtg aagaggttgt gaagaaaatg aagaactatt ggaggcagct cctcaacgct  10380
aagctcatca ctcagagaaa gttcgataac ttgactaagg ctgagagggg aggactctct  10440
gaattggata aggcaggatt catcaagagg cagcttgtgg aaaccaggca gatcactaag  10500
cacgttgcac agatcctcga ttctaggatg aacaccaagt acgatgagaa cgataagttg  10560
atcagggaag tgaaggttat caccctcaag tcaaagctcg tgtctgattt cagaaaggat  10620
ttccaattct acaaggtgag ggaaatcaac aactaccacc acgctcacga tgcttacctt  10680
aacgctgttg ttggaaccgc tctcatcaag aagtatccta agctcgagtc agagttcgtg  10740
tacggtgatt acaaggtgta cgatgtgagg aagatgatcg ctaagtctga gcaagagatc  10800
ggaaaggcta ccgctaagta tttcttctac tctaacatca tgaatttctt caagaccgag  10860
attaccctcg ctaacggtga gatcagaaag aggccactca tcgagacaaa cggtgaaaca  10920
ggtgagatcg tgtgggataa gggaagggat ttcgctaccg ttagaaaggt gctctctatg  10980
ccacaggtga acatcgttaa gaaaaccgag gtgcagaccg gtggattctc taaagagtct  11040
atcctcccta agaggaactc tgataagctc attgctagga agaaggattg ggaccctaag  11100
aaatacggtg gtttcgattc tcctaccgtg gcttactctg ttctcgttgt ggctaaggtt  11160
gagaagggaa agagtaagaa gctcaagtct gttaaggaac ttctcggaat cactatcatg  11220
gaaaggtcat ctttcgagaa gaacccaatc gatttcctcg aggctaaggg atacaaagag  11280
gttaagaagg atctcatcat caagctccca aagtactcac tcttcgaact cgagaacggt  11340
agaaagagga tgctcgcttc tgctggtgag cttcaaaagg gaaacgagct tgctctccca  11400
tctaagtacg ttaactttct ttacctcgct tctcactacg agaagttgaa gggatctcca  11460
gaagataacg agcagaagca acttttcgtt gagcagcaca agcactactt ggatgagatc  11520
atcgagcaga tctctgagtt ctctaaaagg gtgatcctcg ctgatgcaaa cctcgataag  11580
gtgttgtctg cttacaacaa gcacagagat aagcctatca gggaacaggc agagaacatc  11640
atccatctct tcacccttac caacctcggt gctcctgctg ctttcaagta cttcgataca  11700
accatcgata ggaagagata cacctctacc aaagaagtgc tcgatgctac cctcatccat  11760
cagtctatca ctggactcta cgagactagg atcgatctct cacagctcgg tggtgattca  11820
agggctgatc ctaagaagaa gaggaaggtt tgaggcgcgc cgagctccag gcctcccagc  11880
tttcgtccgt atcatcggtt tcgacaacgt tcgtcaagtt caatgcatca gtttcattgc  11940
ccacacacca gaatcctact aagtttgagt attatggcat tggaaaagct gttttcttct  12000
```

```
atcatttgtt ctgcttgtaa tttactgtgt tctttcagtt tttgttttcg gacatcaaaa  12060
tgcaaatgga tggataagag ttaataaatg atatggtcct tttgttcatt ctcaaattat  12120
tattatctgt tgtttttact ttaatgggtt gaatttaagt aagaaaggaa ctaacagtgt  12180
gatattaagg tgcaatgtta gacatataaa acagtctttc acctctcttt ggttatgtct  12240
tgaattggtt tgtttcttca cttatctgtg taatcaagtt tactatgagt ctatgatcaa  12300
gtaattatgc aatcaagtta agtacagtat aggcttgagc tccctaggct tttttcttc  12360
ttcttcgttc atacagtttt tttttgttta tcagcttaca ttttcttgaa ccgtagcttt  12420
cgttttcttc tttttaactt tccattcgga gtttttgtat cttgtttcat agtttgtccc  12480
aggattagaa tgattaggca tcgaaccttc aagaatttga ttgaataaaa catcttcatt  12540
cttaagatat gaagataatc ttcaaaaggc ccctgggaat ctgaaagaag agaagcaggc  12600
ccatttatat gggaaagaac aatagtattt cttatatagg cccatttaag ttgaaaacaa  12660
tcttcaaaag tcccacatcg cttagataag aaaacgaagc tgagtttata tacagctaga  12720
gtcgaagtag tgattggccg ttaatttgag agtccagttt tagagctaga aatagcaagt  12780
taaaataagg ctagtccgtt atcaacttga aaaagtggca ccgagtcggt gcttttttc  12840
tagacccagc tttcttgtac aaagttggca ttacctaggc ccgggcctga ggacgcgtcc  12900
atggttaatt aagacgtccg gaccgactag tggatcctct agagtcgacc tgcaggcatg  12960
caagcttctt cgtcaacatg gtggagcacg acacgcttgt ctactccaaa aatatcaaag  13020
atacagtctc agaagaccaa agggcaattg agacttttca acaaagggta atatccggaa  13080
acctcctcgg attccattgc ccagctatct gtcactttat tgtgaagata gtggaaaagg  13140
aaggtggctc ctacaaatgc catcattgcg ataaaggaaa ggccatcgtt gaagatgcct  13200
ctgccgacag tggtcccaaa gatggacccc cacccacgag gagcatcgtg gaaaaagaag  13260
acgttccaac cacgtcttca aagcaagtgg attgatgtga tatctccact gacgtaaggg  13320
atgacgcaca atcaatccca ctatccttcg caagaccctt ttaaggggga agttcatttc  13380
atttggagag gacacgctga aatcaccagt ctctctgtac aaatcnatct ctctctataa  13440
tattgtgtaa gtagttccca gataagggaa ttagggttct tatagggttt cgctcagctg  13500
ttgagcatat aagaaaccct tagtcgatag atctgttggg gatctaccat gagcccagaa  13560
cgacgcccgg ccgacatccg ccgtgccacc gaggcggaca tgccggcggt ctgcaccatc  13620
gtcaaccact acatcgagac aagcacggtc aacttccgta ccgagccgca ggaaccgcag  13680
gagtggacgg acgacctcgt ccgtctgcgg gagcgctatc cctggctcgt cgccgaggtg  13740
gacggcgagg tcgccggcat cgcctacgcg ggcccctgga aggcacgcaa cgcctacgac  13800
tggacggccg agtcgaccgt gtacgtctcc ccccgccacc agcggacggg actgggctcc  13860
acgctctaca cccacctgct gaagtccctg gaggcacagg gcttcaagag cgtggtcgct  13920
gtcatcgggc tgcccaacga cccgagcgtg cgcatgcacg aggcgctcgg atatgccccc  13980
cgcggcatgc tgcgggcggc cggcttcaag cacgggaact ggcatgacgt gggtttctgg  14040
cagctggact tcagcctgcc ggtaccgccc cgtccggtcc tgcccgtcac cgagatctga  14100
tgacccaact tagtatgtat ttgtatttgt aaaatacttc tatcaataaa atttctaatt  14160
cctaaaacca aaatccaggg gtaccgaaca agcttggcac tggccgtcgt tttacaacgt  14220
cgtgactggg aaaaccctgg cgttacccaa cttaatcgcc ttgcagcaca tccccctttc  14280
gccagctggc gtaatagcga agaggcccgc accgatcgcc cttcccaaca gttgcgcagc  14340
ctgaatggcg aatgagcttg agcttggatc agattgtcgt ttcccgcctt cagtttaaac  14400
```

-continued

```
tatcagtgtt tgacaggata tattggcggg taaacctaag agaaaagagc gtttattaga  14460

ataacggata tttaaaaggg cgtgaaaagg tttatccgtt cgtccatttg tatgtgcatg  14520

ccaaccacag ggttcccctc gggatcaa                                     14548


<210> SEQ ID NO 165
<211> LENGTH: 20
<212> TYPE: DNA
<213> ORGANISM: artificial sequence
<220> FEATURE:
<223> OTHER INFORMATION: synthetic construct

<400> SEQUENCE: 165

gccgttaatt tgagagtcca                                                 20


<210> SEQ ID NO 166
<211> LENGTH: 96
<212> TYPE: DNA
<213> ORGANISM: artificial sequence
<220> FEATURE:
<223> OTHER INFORMATION: synthetic construct

<400> SEQUENCE: 166

gccgttaatt tgagagtcca gttttagagc tagaaatagc aagttaaaat aaggctagtc     60

cgttatcaac ttgaaaaagt ggcaccgagt cggtgc                               96
```